United States Patent
Peto et al.

(10) Patent No.: US 10,562,886 B2
(45) Date of Patent: Feb. 18, 2020

(54) ANTI-CANCER COMPOUNDS

(71) Applicant: THE REGENTS OF THE UNIVERSITY OF CALIFORNIA, Oakland, CA (US)

(72) Inventors: Csaba J. Peto, San Francisco, CA (US); David Jablons, San Francisco, CA (US); Hassan Lemjabbar-Alaoui, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/574,101

(22) PCT Filed: May 23, 2016

(86) PCT No.: PCT/US2016/033806
§ 371 (c)(1),
(2) Date: Nov. 14, 2017

(87) PCT Pub. No.: WO2016/187620
PCT Pub. Date: Nov. 24, 2016

(65) Prior Publication Data
US 2018/0354932 A1 Dec. 13, 2018

Related U.S. Application Data

(60) Provisional application No. 62/164,745, filed on May 21, 2015.

(51) Int. Cl.
| C07D 403/04 | (2006.01) |
| C07D 403/14 | (2006.01) |
| C07D 401/14 | (2006.01) |
| A61P 35/00 | (2006.01) |

(52) U.S. Cl.
CPC ............ *C07D 403/04* (2013.01); *A61P 35/00* (2018.01); *C07D 401/14* (2013.01); *C07D 403/14* (2013.01)

(58) Field of Classification Search
CPC .. C07D 403/04; C07D 401/14; C07D 403/14; A61P 35/00; A61K 31/502
USPC .................................................. 514/210.21
See application file for complete search history.

(56) References Cited

U.S. PATENT DOCUMENTS

| 3,401,171 A | 9/1968 | Craig et al. |
| 6,677,333 B1 | 1/2004 | Seko et al. |
| 7,151,102 B2 | 12/2006 | Martin et al. |
| 2004/0235886 A1 | 11/2004 | Charifson et al. |
| 2009/0270617 A1 | 10/2009 | Menear et al. |
| 2012/0286157 A1 | 11/2012 | Fuhrmann et al. |
| 2014/0221314 A1 | 8/2014 | Shen et al. |
| 2014/0336190 A1 | 11/2014 | Aktoudianakis |

FOREIGN PATENT DOCUMENTS

| CN | 102372706 | | 3/2012 |
| SU | 1019810 A1 | * | 4/1991 |
| SU | 1019810 A1 | | 4/1991 |
| SU | 1218649 | | 4/1991 |
| WO | WO 1999/040072 | | 8/1999 |
| WO | WO 2000/050419 | | 8/2000 |
| WO | WO 2002/036576 | | 5/2002 |
| WO | WO 2004/080976 | | 9/2004 |
| WO | WO 2005/112932 | | 12/2005 |
| WO | WO 2006/124874 | | 11/2006 |
| WO | WO 2008/114023 | | 9/2008 |
| WO | WO 2012/166983 | | 12/2012 |
| WO | WO 2014/102817 | | 7/2014 |
| WO | WO 2017/223516 | | 12/2017 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Sharma et al., "Virtual screening reveals allosteric inhibitors of the Toxoplasma gondii thymidylate synthase—dihydrofolate reductase." Bioorganic & Medicinal Chemistry Letters, 24, pp. 1232-1235 (2014).
Cheong et al., European Journal of Medicinal Chemistry, vol. 144, pp. 372-385 (2018).
Dubey et al., Journal of Medicinal Chemistry, vol. 28, pp. 1748-1750 (1985).
Ferraris, D.V., Journal of Medicinal Chemistry, vol. 53, No. 12, pp. 4561-4584 (2010).
Grillot et al., Journal of Medicinal Chemistry, vol. 57, pp. 8792-8816 (2014).
Hong et al., Journal of Medicinal Chemistry, vol. 56, pp. 3531-3545 (2013).
Hughes, D., Org. Process Res. Dev., vol. 21, No. 9, 1227-1244 (2017).
Kruse et al., Journal of Medicinal Chemistry, vol. 32, pp. 409-417 (1989).
Menear et al., Journal of Medicinal Chemistry, vol. 51, pp. 6581-6591 (2008).
Papeo, G. et al., Expert Opinion on Therapeutic Patents, vol. 23, No. 4, pp. 503-514 (2013).
Park et al., Journal Am. Chem. Soc., vol. 135, pp. 8227-8237 (2013).

(Continued)

*Primary Examiner* — Kristin A Vajda
(74) *Attorney, Agent, or Firm* — Morgan, Lewis & Bockius LLP; Jeffry S. Mann; Todd Esker

(57) ABSTRACT

This invention provides, among other things, compounds useful for treating diseases such as cancer, pharmaceutical formulations containing such compounds, as well as combinations of these compounds with at least one additional therapeutic agent.

39 Claims, 9 Drawing Sheets

(56) References Cited

OTHER PUBLICATIONS

Figure 4:
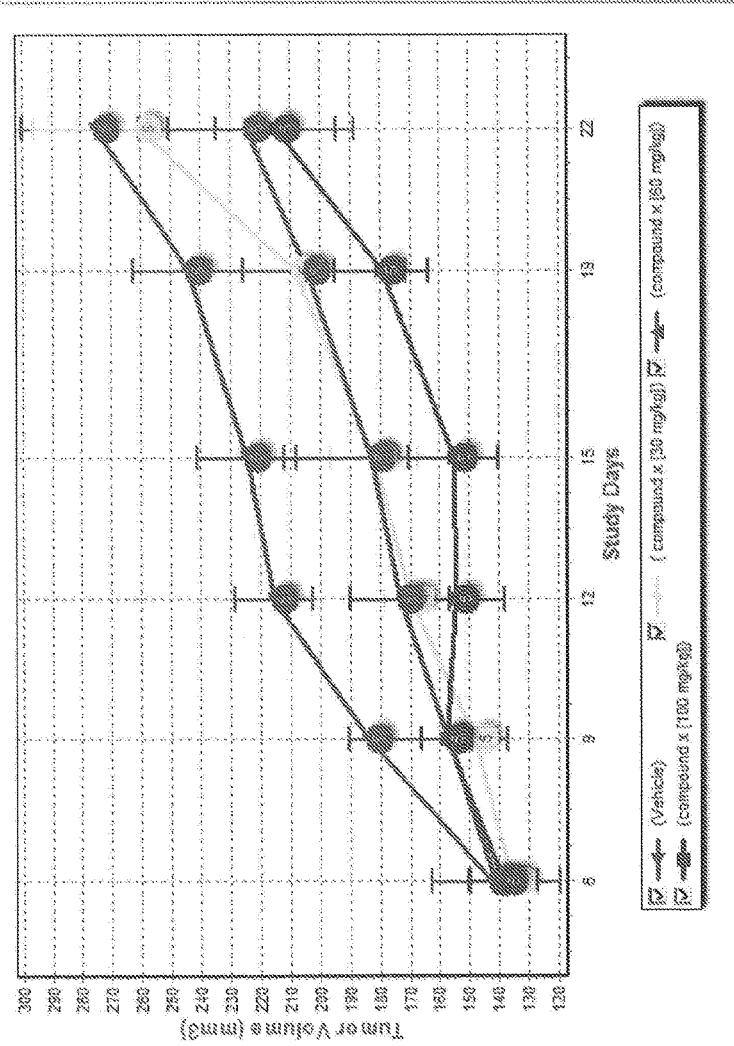

Peukert, S. et al., Expert Opinion on Therapeutic Patents, vol. 14, No. 11, pp. 1531-1551 (2004).
Ram et al., Journal of Medicinal Chemistry, vol. 35, pp. 539-547 (1992).
Yuan, Z. et al., Expert Opinion on Therapeutic Patents, vol. 27, No. 3, pp. 363-382 (2016).
Zaremba, T. et al., Anti-Cancer Agents in Medicinal Chemistry, vol. 7, No. 5, pp. 515-523 (2007).

* cited by examiner

FIGURE 1
Development of novel triple PARP1/ABL/Tubulin polymerization inhibitors

| Compound Name | PARP1 (IC50 µM) | ABL1 (IC50 µM) | ABL1 E255K (IC50 µM) | ABL2 (Arg) (IC50 µM) | Cellular rH2AX change (1µM)[1] | Tubulin polymerization[2] |
|---|---|---|---|---|---|---|
| 2 | 15.97 | 0.777 | NT[5] | 3.490 | 43.00 | -5.966 |
| 1 | 9.980 | 0.238 | 0.646 | 0.881 | NT | 40.065 |
| 3 | 6.681 | 0.969 | NT | 2.250 | NT | 78.346 |
| Olaparib | 0.005 | NA | NT | NT | 34.70 | NA |
| Vinblastine | NT | NT | NT | NT | NT | 139.789 |
| Paclitaxel | NT | NT | NT | NT | NT | -267.2112 |

Compounds have demonstrated high-target specificity in *in vitro* enzymatic assays:
- Compounds inhibit PARP1 activity
- Compounds inhibit ABL1 activity
- Compounds inhibit mutated ABL1 activity
- Compounds inhibit ABL2 activity
- Compounds inhibit induce double strand DNA damage
- Compounds inhibit tubulin polymerization 1. Cellular rH2AX, a biomarker for DNA Double strand breaks (% Increase versus DMSO only control) compound concentration = 1µM)
2. % Inhibition at 30 minutes, compound concentration=4µM
NA= Not Active
NT= Not Tested
✓ Olaparib is a potent PARP1 inhibitor currently in clinical testing Breast, ovarian and other cancers
✓ Vinblastine and paclitaxol are approved antimitotic inhibitors

FIGURE 2

**Novel compounds dramatically suppress *in vitro* cell viability of various cancer cell types**

(Mean IC50s from three different experiments)

| | Lung cancer | Ovarian cancer | Pancreatic cancer | Breast cancer | Mesothelioma | | | |
|---|---|---|---|---|---|---|---|---|
| | A549 | OVCAR8 | CAPAN1 | MDA-MB-436 | MSTO-211H | H28 | H2052 | H2452 |
| 1 | 0.1264 | 0.5542 | 0.5441 | 0.657 | 0.19 | 0.51 | 0.10 | 0.45 |
| 3 | 0.6975 | 3.336 | 1.295 | 1.996 | 1.78 | 3.73 | 0.86 | 2.75 |
| 2 | 2.68 | 2.527 | 3.3 | 2.913 | 3.72 | 5.12 | 2.08 | 5.00 |
| Olaparib | 2.706 | 9.832 | 10.31 | 2.328 | 6.78 | 33.57 | 6.23 | 4.27 |
| Imatinib Mesylate | NT | NT | NT | NT | 9.09 | 30.65 | 6.588 | 7.44 |
| Ponatinib | NT | NT | NT | NT | 0.10 | 0.64 | 0.11 | 0.84 |

✓ Olaparib is a potent PARP1 inhibitor currently in clinical testing Breast, ovarian and other cancers ✓ Gleevac=Imatinib Mesylate is an orally bioavailability mesylate salt of Imatinib, which is a multi-target inhibitor of v-Abl, c-Kit and PDGFR with IC50 of 0.6 μM, 0.1 μM, respectively.

✓ Ponatinib is a novel, potent multi-target inhibitor of Abl, PDGFRα, VEGFR2, FGFR1 and Src with IC50 or 0.37 nM, 1.1nM, 1.5 nM, 2.2 nM and 5.4 nM, respectively

FIGURE 3

Testing of Compound 1 on 13 Multiple Myeloma cell lines
12/04/2014

*Cell Viability assay*

| Cell lines | IC50 ($\mu M$) |
|---|---|
| Amo1 | 0.151 |
| H929 | 0.292 |
| JJN3 | 0.355 |
| KMS11 | 0.385 |
| L363 | 0.702 |
| MM1.R | 0.608 |
| MM1.S | 0.379 |
| OPM2 | 0.305 |
| OPM1 | 0.490 |
| RPMI | 0.540 |
| U266 | 0.473 |
| INA6 | 0.264 |
| LP1 | 0.279 |

Compound 1 synergizes with cisplatin in suppressing in vitro cancer cell viability

ANTI-CANCER COMPOUNDS

CROSS-REFERENCE TO RELATED APPLICATIONS

The application claims the benefit of U.S. Provisional Application No. 62/164,745 filed May 21, 2015, which is incorporated herein by reference in its entirety.

BACKGROUND OF THE INVENTION

There is a need in the art for compounds which can treat cancer. This, and other uses of these compounds are described herein.

SUMMARY OF THE INVENTION

This invention provides, among other things, compounds useful for treating diseases associated with PARP1 (Poly ADP Ribose Polymerase and/or ABL1 (Abelson murine leukemia viral oncogene homolog and/or ABL2 (Abelson murine leukemia viral oncogene homolog and/or tubulin, pharmaceutical formulations containing such compounds, as well as combinations of these compounds with at least one additional therapeutic agent.

DETAILED DESCRIPTION OF THE DRAWINGS

Figure 5:
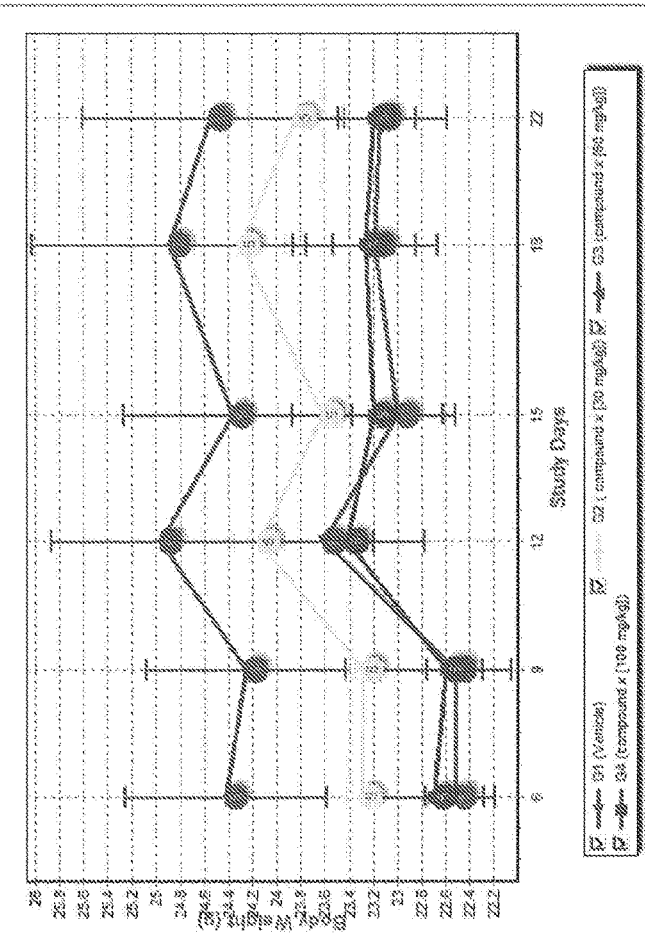
Figure 6:
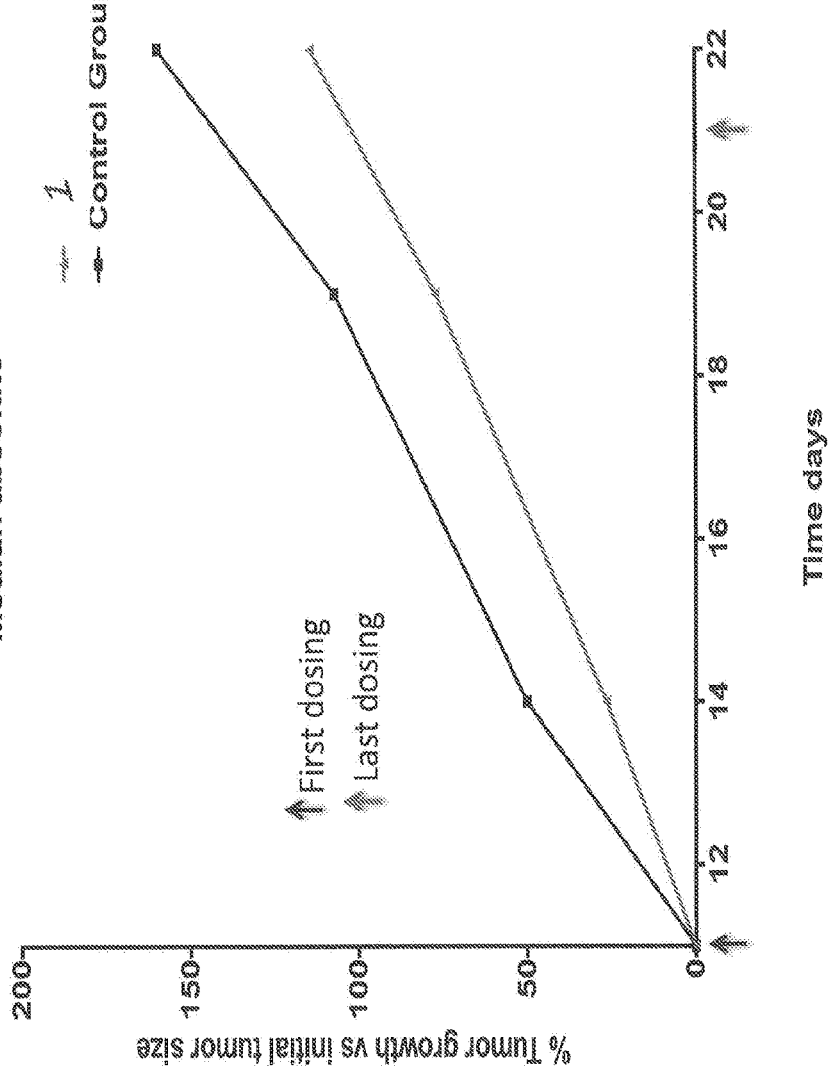
Figure 7:
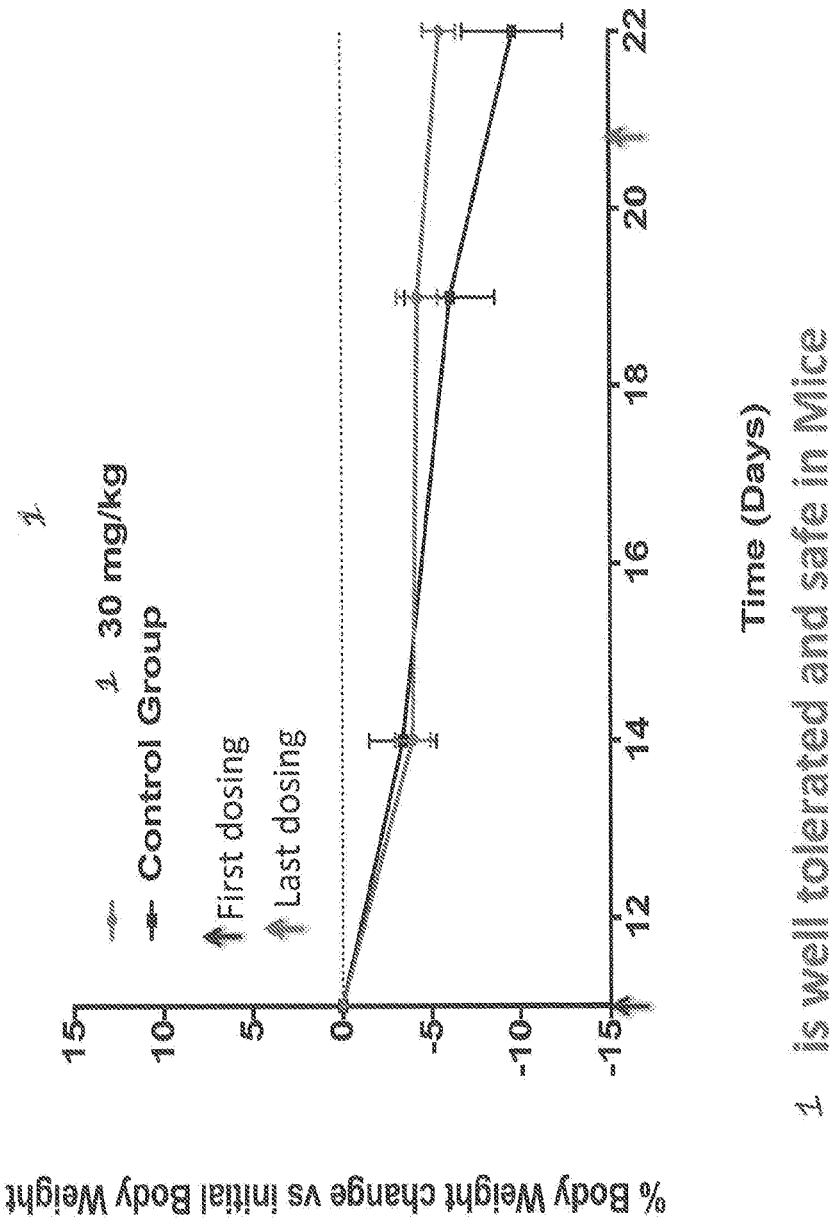
Figure 8:
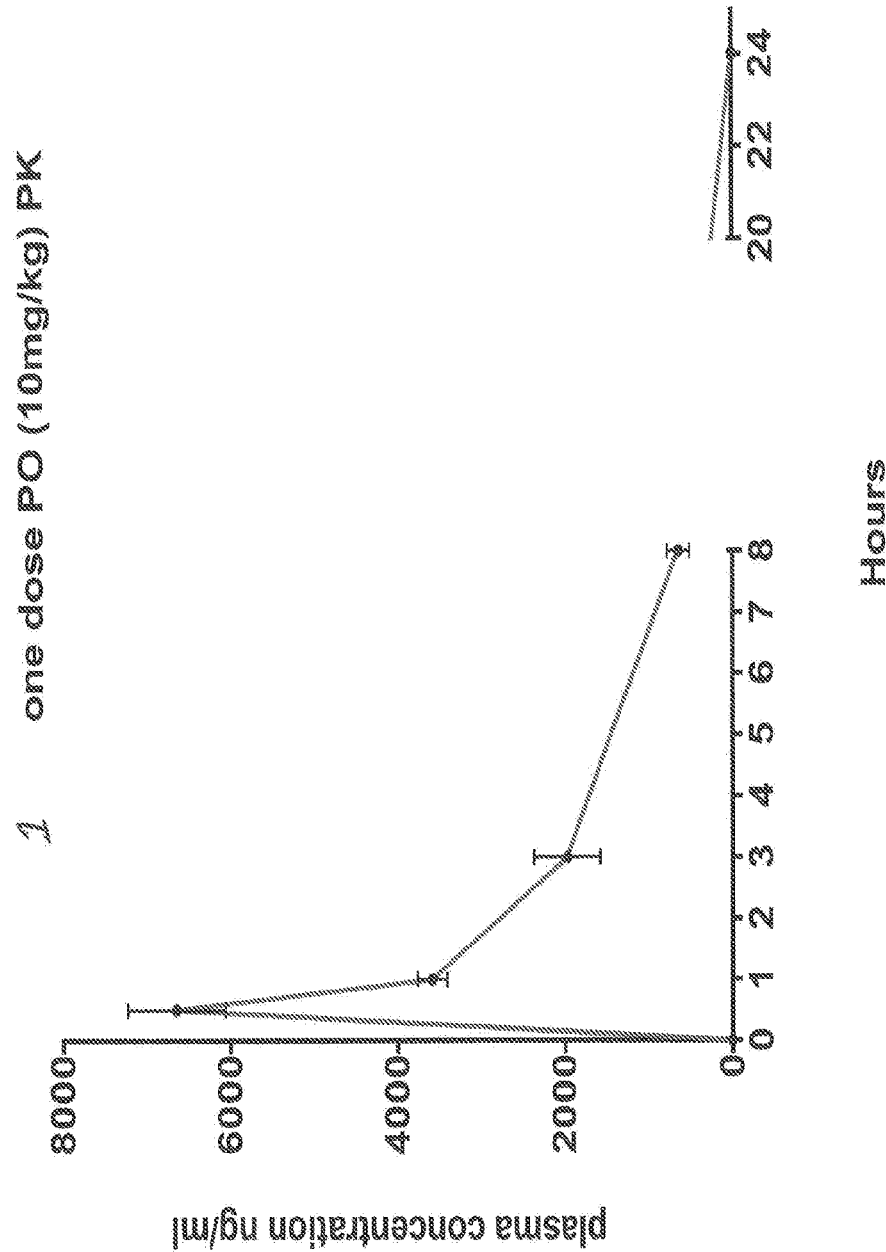
Figure 9:
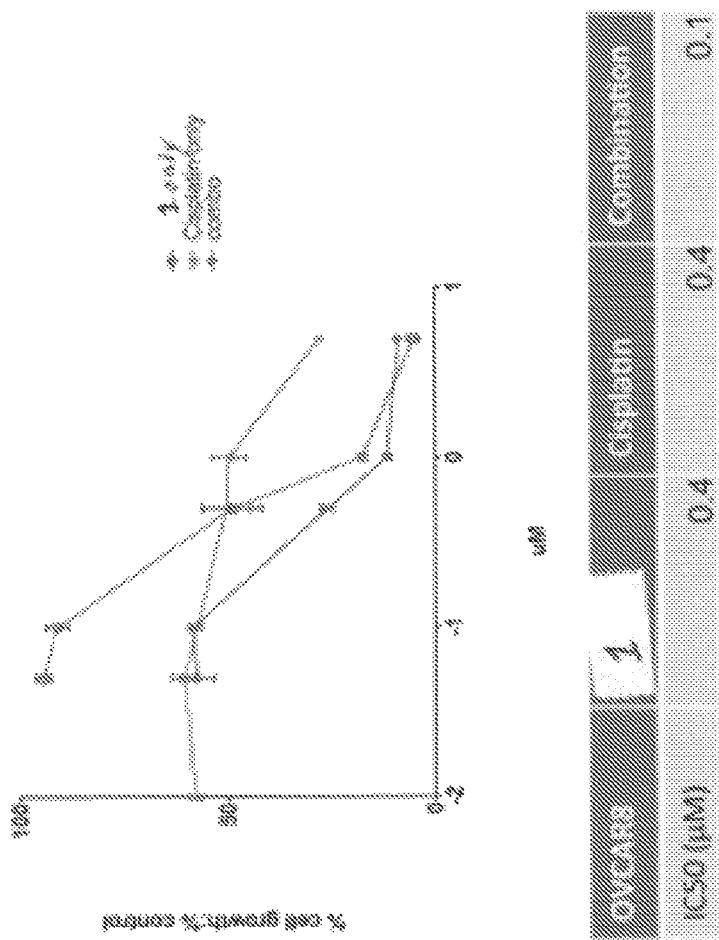

FIG. 1 provides biological data regarding the invention.
FIG. 2 provides biological data regarding the invention.
FIG. 3 provides biological data regarding the invention.
FIG. 4 provides biological data regarding the invention.
FIG. 5 provides biological data regarding the invention.
FIG. 6 provides biological data regarding the invention.
FIG. 7 provides biological data regarding the invention.
FIG. 8 provides biological data regarding the invention.
FIG. 9 provides biological data regarding the invention.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used. Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl)amide; KHMDS is potassium bis(trimethylsilyl)amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2$(pddf) is 1,1'-Bis (diphenylphosphino) ferrocene]dichloropalladium(II); Pd/C is the catalyst known as palladium on carbon; $Pd_2(dba)_3$ is an organometallic catalyst known as tris(dibenzylideneacetone)dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "poly" as used herein means at least 2. For example, a polyvalent metal ion is a metal ion having a valency of at least 2.

"Moiety" refers to a radical of a molecule that is attached to the remainder of the molecule.

The symbol ⌇, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—O$CH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above.

Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR" C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R'"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R'" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R'"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted C$_1$ or C$_2$ or C$_3$ or C$_4$ or C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5 to 7-membered ring" or "5 or 6 or 7 membered ring" includes, for example phenyl, pyridinyl and piperidinyl. The term "5 to 7-membered heterocycloalkyl ring" "5 or 6 or 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), and aluminum (Al).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical formulation administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as PARP1 (Poly ADP Ribose Polymerase1) and/or ABL1 (Abelson murine leukemia viral oncogene homolog 1) and/or ABL2 (Abelson murine leukemia viral oncogene homolog 2) and/or tubulin.

Embodiments of the invention also encompass compounds that are poly- or multi-valent species, including, for example, species such as dimers, trimers, tetramers and higher homologs of the compounds of use in the invention or reactive analogues thereof.

II. Introduction

The invention provides novel compounds. The novel compounds, as well as pharmaceutical formulations containing such compounds or combinations of these compounds with at least one additional therapeutic agent, can be used for, among other things, treating diseases, including cancer.

III. The Compounds

III. a)

In one aspect, the invention provides a compound of the invention. In an exemplary embodiment, the invention is a compound described herein. In an exemplary embodiment, the invention is a compound according to a formula described herein.

In another aspect, the invention provides a compound, or a salt or a hydrate or a solvate thereof, having a structure according to formula (I):

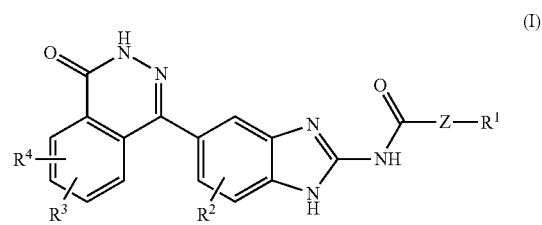

(I)

wherein Z is —O— or —CH$_2$— or —NH— or —N(CH$_2$R$^5$)— wherein R$^5$ is hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl; R$^1$ is hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ heteroalkyl or substituted or unsubstituted C$_3$ or C$_4$ or C$_5$ or C$_6$ cycloalkyl or unsubstituted phenyl or substituted or unsubstituted piperidinyl or substituted or unsubstituted azetidinyl; R$^2$ is hydrogen or methyl or ethyl or propyl or isopropyl or halogen; R$^3$ is hydrogen or halogen or methyl or ethyl or propyl or isopropyl; R$^4$ is hydrogen or halogen or methyl or ethyl or propyl or isopropyl. In an exemplary embodiment, R$^1$ is unsubstituted C$_1$ or C$_2$ or C$_3$ or C$_4$ or C$_5$ or C$_6$ or C$_7$ or C$_8$ or C$_9$ or C$_{10}$ alkyl. In an exemplary embodiment, R$^1$ is substituted C$_1$ or C$_2$ or C$_3$ or C$_4$ or C$_5$ or C$_6$ or C$_7$ or C$_8$ or C$_9$ or C$_{10}$ alkyl. In an exemplary embodiment, R$^1$ is unsubstituted C$_1$ or C$_2$ or C$_3$ or C$_4$ or C$_5$ or C$_6$ or C$_7$ or C$_8$ or C$_9$ or C$_{10}$ heteroalkyl. In an exemplary embodiment, R$^1$ is substituted C$_1$ or C$_2$ or C$_3$ or C$_4$ or C$_5$ or C$_6$ or C$_7$ or C$_8$ or C$_9$ or C$_{10}$ alkyl. In an exemplary embodiment, R$^5$ is H.

In another aspect, the invention provides a compound, or a salt or a hydrate or a solvate thereof, having a structure according to formula (II):

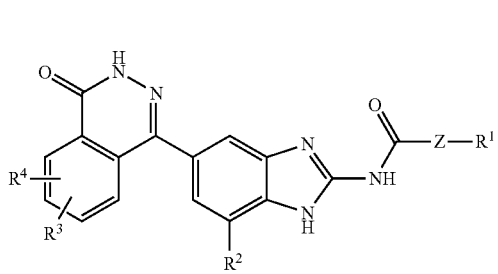

(II)

wherein Z, $R^1$, $R^2$, $R^3$, and $R^4$ are as described herein.

In another aspect, the invention provides a compound, or a salt or a hydrate or a solvate thereof, having a structure according to formula (III):

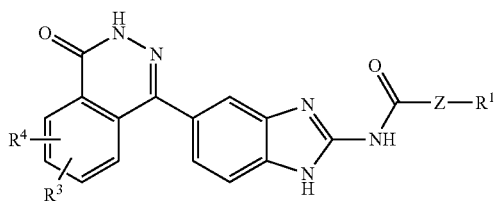

(III)

wherein Z, $R^1$, $R^3$, and $R^4$ are as described herein.

In another aspect, the invention provides a compound, or a salt or a hydrate or a solvate thereof, having a structure according to formula (IV):

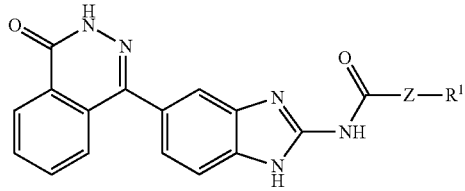

(IV)

wherein Z and $R^1$ are as described herein.

In another aspect, the invention provides a compound, or a salt or a hydrate or a solvate thereof, having a structure according to formula (V):

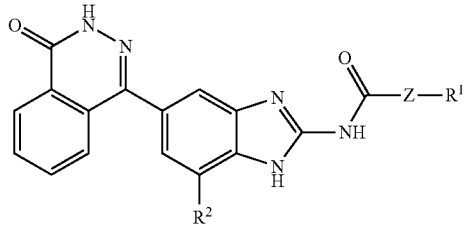

(V)

wherein Z, $R^1$ and $R^2$ are as described herein.

In another aspect, the invention provides a compound, or a salt or a hydrate or a solvate thereof, having a structure according to formula (VI):

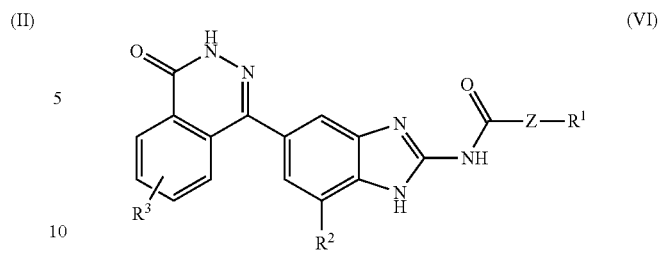

(VI)

wherein Z, $R^1$, $R^2$ and $R^3$ are as described herein.

In another aspect, the invention provides a compound, or a salt or a hydrate or a solvate thereof, having a structure according to formula (VII):

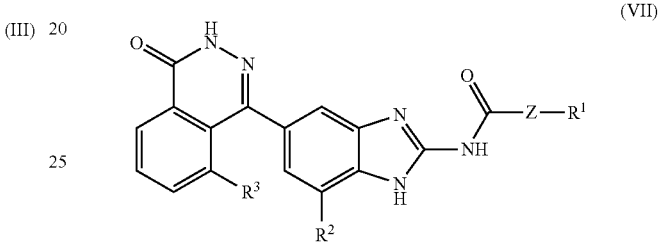

(VII)

wherein Z, $R^1$, $R^2$ and $R^3$ are as described herein.

In another aspect, the invention provides a compound, or a salt or a hydrate or a solvate thereof, having a structure according to formula (VIII):

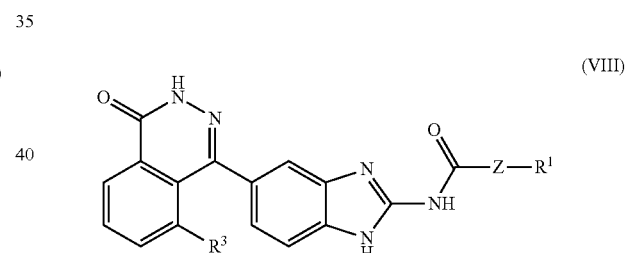

(VIII)

wherein Z, $R^1$ and $R^3$ are as described herein.

In another aspect, the invention provides a compound, or a salt or a hydrate or a solvate thereof, having a structure according to formula (IX):

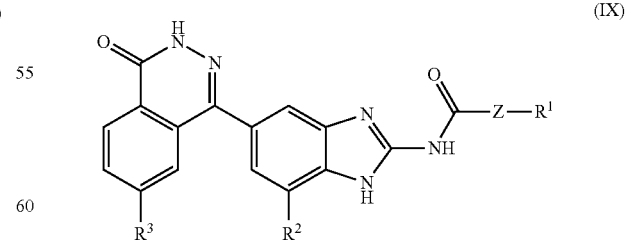

(IX)

wherein Z, $R^1$, $R^2$ and $R^3$ are as described herein.

In another aspect, the invention provides a compound, or a salt or a hydrate or a solvate thereof, having a structure according to formula (X):

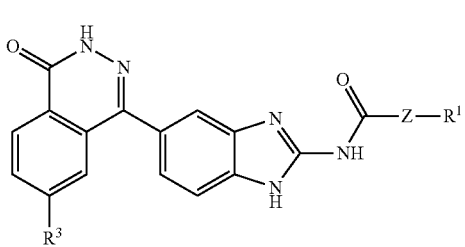

(X)

wherein Z, R$^1$ and R$^3$ are as described herein.

In another aspect, the invention provides a compound, or a salt or a hydrate or a solvate thereof, having a structure according to formula (XI):

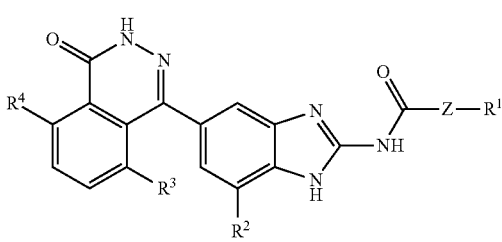

(XI)

wherein Z, R$^1$, R$^2$, R$^3$, and R$^4$ are as described herein.

In another aspect, the invention provides a compound, or a salt or a hydrate or a solvate thereof, having a structure according to formula (XII):

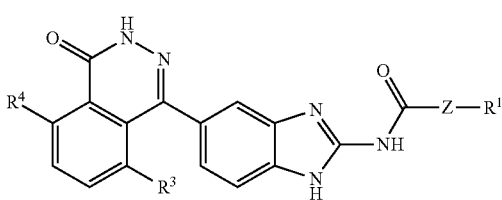

(XII)

wherein Z, R$^1$, R$^3$, and R$^4$ are as described herein.

In another aspect, the invention provides a compound, or a salt or a hydrate or a solvate thereof, having a structure according to formula (XIII):

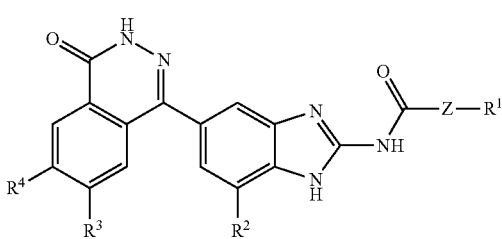

(XIII)

wherein Z, R$^1$, R$^2$, R$^3$, and R$^4$ are as described herein.

In another aspect, the invention provides a compound, or a salt or a hydrate or a solvate thereof, having a structure according to formula (XIV):

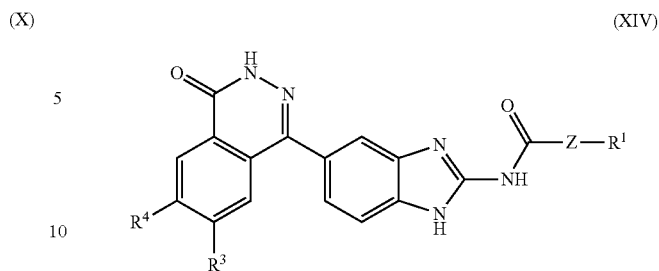

(XIV)

wherein Z, R$^1$, R$^3$, and R$^4$ are as described herein.

In another aspect, the invention provides a compound, or a salt or a hydrate or a solvate thereof, having a structure according to formula (XV):

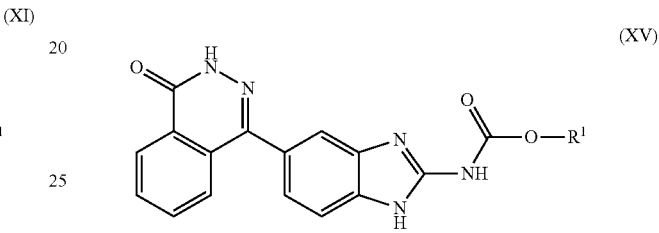

(XV)

wherein R$^1$ is as described wherein.

In an exemplary embodiment, the compound is according to a formula described herein, or a salt, or a hydrate, or a solvate thereof, wherein Z is —O— or —CH$_2$— or —NH—; R$^1$ is hydrogen or substituted or unsubstituted C$_1$ or C$_2$ or C$_3$ or C$_4$ or C$_5$ alkyl or substituted or unsubstituted C$_1$ or C$_2$ or C$_3$ or C$_4$ or C$_5$ heteroalkyl or substituted or unsubstituted C$_3$ or C$_4$ or C$_5$ or C$_6$ cycloalkyl or unsubstituted phenyl or substituted or unsubstituted piperidinyl or substituted or unsubstituted azetidinyl; R$^2$ is hydrogen or methyl or halogen; R$^3$ is hydrogen or fluoro or chloro or methyl; R$^4$ is hydrogen or fluoro or chloro or methyl.

In an exemplary embodiment, the compound is according to a formula described herein, or a salt, or a hydrate, or a solvate thereof, wherein Z is —O— or —CH$_2$— or —NH—; R$^1$ is substituted or unsubstituted C$_1$ or C$_2$ or C$_3$ or C$_4$ or C$_5$ alkyl or substituted or unsubstituted C$_1$ or C$_2$ or C$_3$ or C$_4$ or C$_5$ heteroalkyl or substituted or unsubstituted C$_3$ or C$_4$ or C$_5$ or C$_6$ cycloalkyl or unsubstituted phenyl or substituted or unsubstituted piperidinyl or substituted or unsubstituted azetidinyl; R$^2$ is hydrogen or methyl or halogen; R$^3$ is hydrogen or fluoro or chloro or methyl; R$^4$ is hydrogen or fluoro or chloro or methyl.

In an exemplary embodiment, the compound is according to a formula described herein, or a salt, or a hydrate, or a solvate thereof, wherein Z is —CH$_2$—; R$^1$ is hydrogen; R$^2$ is hydrogen or methyl or halogen; R$^3$ is hydrogen or fluoro or chloro or methyl; R$^4$ is hydrogen or fluoro or chloro or methyl.

In an exemplary embodiment, the compound is according to a formula described herein, or a salt, or a hydrate, or a solvate thereof, wherein R$^1$, R$^2$, R$^3$, and R$^4$ are as described herein, and Z is —O—. In an exemplary embodiment, the compound is a formula described herein, or a salt, or a hydrate, or a solvate thereof, wherein R$^1$, R$^2$, R$^3$, and R$^4$ are as described herein, and Z is —CH$_2$—. In an exemplary embodiment, the compound is a formula described herein, or a salt, or a hydrate, or a solvate thereof, wherein R$^2$, R$^3$, and R$^4$ are as described herein, Z is —CH$_2$—, and R$^1$ is hydrogen. In an exemplary embodiment, the compound is according to formula (I), or a salt, or a hydrate, or a solvate thereof, wherein $R^1$, $R^2$, $R^3$, and $R^4$ are as described herein, and Z is —NH—. In an exemplary embodiment, the compound is a formula described herein, or a salt, or a hydrate, or a solvate thereof, wherein $R^1$, $R^2$, $R^3$, and $R^4$ are as described herein, and Z is —N(CH$_2$R$^5$). In an exemplary embodiment, the compound is a formula described herein, or a salt, or a hydrate, or a solvate thereof, wherein $R^1$, $R^2$, $R^3$, and $R^4$ are as described herein, and Z is —N(CH$_3$)—.

In an exemplary embodiment, the compound is a formula described herein, or a salt, or a hydrate, or a solvate thereof, wherein Z, $R^1$, $R^3$, and $R^4$ are as described herein, and $R^2$ is methyl. In an exemplary embodiment, the compound is a formula described herein, or a salt, or a hydrate, or a solvate thereof, wherein Z, $R^1$, $R^3$, and $R^4$ are as described herein, and $R^2$ is ethyl. In an exemplary embodiment, the compound is a formula described herein, or a salt, or a hydrate, or a solvate thereof, wherein Z, $R^1$, $R^3$, and $R^4$ are as described herein, and $R^2$ is propyl. In an exemplary embodiment, the compound is a formula described herein, or a salt, or a hydrate, or a solvate thereof, wherein Z, $R^1$, $R^3$, and $R^4$ are as described herein, and $R^2$ is isopropyl. In an exemplary embodiment, the compound is a formula described herein, or a salt, or a hydrate, or a solvate thereof, wherein Z, $R^1$, $R^3$, and $R^4$ are as described herein, and $R^2$ is halogen. In an exemplary embodiment, the compound is a formula described herein, or a salt, or a hydrate, or a solvate thereof, wherein Z, $R^3$, and $R^4$ are as described herein, and $R^2$ is chlorine. In an exemplary embodiment, the compound is a formula described herein, or a salt, or a hydrate, or a solvate thereof, wherein Z, $R^1$, $R^3$, and $R^4$ are as described herein, and $R^2$ is bromine. In an exemplary embodiment, the compound is a formula described herein, or a salt, or a hydrate, or a solvate thereof, wherein Z, $R^1$, $R^3$, and $R^4$ are as described herein, and $R^2$ is hydrogen.

In an exemplary embodiment, the compound is a formula described herein, or a salt, or a hydrate, or a solvate thereof, wherein Z, $R^1$, $R^2$, and $R^4$ are as described herein, and $R^3$ is fluoro. In an exemplary embodiment, the compound is a formula described herein, or a salt, or a hydrate, or a solvate thereof, wherein Z, $R^1$, $R^2$, and $R^4$ are as described herein, and $R^3$ is chloro. In an exemplary embodiment, the compound is a formula described herein, or a salt, or a hydrate, or a solvate thereof, wherein Z, $R^1$, $R^2$, and $R^4$ are as described herein, and $R^3$ is methyl. In an exemplary embodiment, the compound is a formula described herein, or a salt, or a hydrate, or a solvate thereof, wherein Z, $R^1$, $R^2$, and $R^4$ are as described herein, and $R^3$ is hydrogen.

In an exemplary embodiment, the compound is a formula described herein, or a salt, or a hydrate, or a solvate thereof, wherein Z, $R^1$ and $R^2$ are as described herein, $R^3$ is fluoro and $R^4$ is hydrogen. In an exemplary embodiment, the compound is a formula described herein, or a salt, or a hydrate, or a solvate thereof, wherein Z, $R^1$ and $R^2$ are as described herein, $R^3$ is chloro and $R^4$ is hydrogen. In an exemplary embodiment, the compound is a formula described herein, or a salt, or a hydrate, or a solvate thereof, wherein Z, $R^1$ and $R^2$ are as described herein, $R^3$ is methyl and $R^4$ is hydrogen. In an exemplary embodiment, the compound is a formula described herein, or a salt, or a hydrate, or a solvate thereof, wherein Z, $R^1$ and $R^2$ are as described herein, $R^3$ is hydrogen and $R^4$ is hydrogen. In an exemplary embodiment, the compound is a formula described herein, or a salt, or a hydrate, or a solvate thereof, wherein Z, $R^1$ and $R^2$ are as described herein, $R^3$ is fluoro and $R^4$ is fluoro. In an exemplary embodiment, the compound is a formula described herein, or a salt, or a hydrate, or a solvate thereof, wherein Z, $R^1$ and $R^2$ are as described herein, $R^3$ is chloro and $R^4$ is chloro.

In an exemplary embodiment, the compound is a formula described herein, or a salt, or a hydrate, or a solvate thereof, wherein Z, $R^1$ is as described herein, and $R^2$ is hydrogen, $R^3$ is hydrogen and $R^4$ is hydrogen.

In an exemplary embodiment, the compound is a formula described herein, or a salt, or a hydrate, or a solvate thereof, wherein Z, $R^2$, $R^3$, and $R^4$ are as described herein, and $R^1$ is methyl. In an exemplary embodiment, the compound is a formula described herein, or a salt, or a hydrate, or a solvate thereof, wherein Z, $R^2$, $R^3$, and $R^4$ are as described herein, and $R^1$ is ethyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_3$ alkyl. In an exemplary embodiment, the compound is a formula described herein, or a salt, or a hydrate, or a solvate thereof, wherein Z, $R^2$, $R^3$, and $R^4$ are as described herein, and $R^1$ is propyl. In an exemplary embodiment, the compound is a formula described herein, or a salt, or a hydrate, or a solvate thereof, wherein Z, $R^2$, $R^3$, and $R^4$ are as described herein, and $R^1$ is isopropyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_4$ alkyl. In an exemplary embodiment, the compound is a formula described herein, or a salt, or a hydrate, or a solvate thereof, wherein Z, $R^2$, $R^3$, and $R^4$ are as described herein, and $R^1$ is t-butyl. In an exemplary embodiment, the compound is a formula described herein, or a salt, or a hydrate, or a solvate thereof, wherein Z, $R^2$, $R^3$, and $R^4$ are as described herein, and $R^1$ is sec-butyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_5$ alkyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_6$ alkyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_7$ alkyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_8$ alkyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_9$ alkyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted $C_{10}$ alkyl.

In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with unsubstituted $C_1$ or $C_2$ or $C_3$ or $C_4$ or $C_5$ or $C_6$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ alkyl, substituted with unsubstituted $C_1$ or $C_2$ or $C_3$ or $C_4$ or $C_5$ or $C_6$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ alkyl, substituted with unsubstituted $C_1$ or $C_2$ or $C_3$ or $C_4$ or $C_5$ or $C_6$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ alkyl, substituted with unsubstituted $C_1$ or $C_2$ or $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_1$ or $C_2$ or $C_3$ or $C_4$ or $C_5$ or $C_6$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_1$ or $C_2$ or $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is ethyl, substituted with methoxy.

In an exemplary embodiment, the compound is a formula described herein, or a salt, or a hydrate, or a solvate thereof, wherein Z, $R^2$, $R^3$, and $R^4$ are as described herein, and $R^1$ is $C_1$ alkyl, substituted with unsubstituted $C_1$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ alkyl, substituted with unsubstituted $C_2$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ alkyl, substituted with unsubstituted $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ alkyl, substituted with unsubstituted $C_4$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ alkyl, substituted with unsubstituted $C_5$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_1$ alkyl, substituted with unsubstituted $C_6$ alkoxy.

In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_1$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_2$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_4$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_5$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_2$ alkyl, substituted with unsubstituted $C_6$ alkoxy.

In an exemplary embodiment, the compound is a formula described herein, or a salt, or a hydrate, or a solvate thereof, wherein Z, $R^2$, $R^3$, and $R^4$ are as described herein, and $R^1$ is $C_3$ alkyl, substituted with unsubstituted $C_1$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_3$ alkyl, substituted with unsubstituted $C_2$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_3$ alkyl, substituted with unsubstituted $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_3$ alkyl, substituted with unsubstituted $C_4$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_3$ alkyl, substituted with unsubstituted $C_5$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_3$ alkyl, substituted with unsubstituted $C_6$ alkoxy.

In an exemplary embodiment, the compound is a formula described herein, or a salt, or a hydrate, or a solvate thereof, wherein Z, $R^2$, $R^3$, and $R^4$ are as described herein, and $R^1$ is $C_4$ alkyl, substituted with unsubstituted $C_1$ or $C_2$ or $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_4$ alkyl, substituted with unsubstituted $C_4$ or $C_5$ or $C_6$ alkoxy.

In an exemplary embodiment, the compound is a formula described herein, or a salt, or a hydrate, or a solvate thereof, wherein Z, $R^2$, $R^3$, and $R^4$ are as described herein, and $R^1$ is $C_5$ alkyl, substituted with unsubstituted $C_1$ or $C_2$ or $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_5$ alkyl, substituted with unsubstituted $C_4$ or $C_5$ or $C_6$ alkoxy.

In an exemplary embodiment, the compound is a formula described herein, or a salt, or a hydrate, or a solvate thereof, wherein Z, $R^2$, $R^3$, and $R^4$ are as described herein, and $R^1$ is $C_6$ alkyl, substituted with unsubstituted $C_1$ or $C_2$ or $C_3$ alkoxy. In an exemplary embodiment, the compound is a formula described herein, or a salt, or a hydrate, or a solvate thereof, wherein Z, $R^2$, $R^3$, and $R^4$ are as described herein, and $R^1$ is $C_6$ alkyl, substituted with unsubstituted $C_4$ or $C_5$ or $C_6$ alkoxy.

In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with unsubstituted dimethylamino. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$, substituted with unsubstituted dimethylamino. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$, substituted with unsubstituted dimethylamino.

In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with fluorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ alkyl, substituted with fluorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with one fluorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ alkyl, substituted with one fluorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with two fluorines. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ alkyl, substituted with two fluorines. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ alkyl, substituted with three fluorines. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ alkyl, substituted with three fluorines.

In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with chlorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ alkyl, substituted with chlorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with one chlorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ alkyl, substituted with one chlorine. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with two chlorines. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ alkyl, substituted with two chlorines. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ alkyl, substituted with three chlorines. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ alkyl, substituted with three chlorines.

In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ or $C_4$ or $C_5$ or $C_6$ or $C_7$ or $C_8$ or $C_9$ or $C_{10}$ alkyl, substituted with cyano. In an exemplary embodiment, the compound is a formula described herein, or a salt, or a hydrate, or a solvate thereof, wherein Z, $R^2$, $R^3$, and $R^4$ are as described herein, and $R^1$ is $C_1$ or $C_2$ or $C_3$ alkyl, substituted with cyano. In an exemplary embodiment, the compound is a formula described herein, or a salt, or a hydrate, or a solvate thereof, wherein Z, $R^2$, $R^3$, and $R^4$ are as described herein, and $R^1$ is benzyl. In an exemplary embodiment, the compound is a formula described herein, or a salt, or a hydrate, or a solvate thereof, wherein Z, $R^2$, $R^3$, and $R^4$ are as described herein, and $R^1$ is unsubstituted phenyl. In an exemplary embodiment, the compound is a formula described herein, or a salt, or a hydrate, or a solvate thereof, wherein Z, $R^2$, $R^3$, and $R^4$ are as described herein, and $R^1$ is cyclohexyl.

In an exemplary embodiment, the compound is a formula described herein, or a salt, or a hydrate, or a solvate thereof, wherein $R^1$ is as described herein, and Z is O; $R^2$ is H; $R^3$ is H; and $R^4$ is H. In an exemplary embodiment, the compound is a formula described herein, or a salt, or a hydrate, or a solvate thereof, wherein $R^1$ is as described herein, and Z is NH; $R^2$ is H; $R^3$ is H; and $R^4$ is H. In an exemplary embodiment, the compound is a formula described herein, or a salt, or a hydrate, or a solvate thereof, wherein $R^1$ is as described herein, and Z is $CH_2$; $R^2$ is H; $R^3$ is H; and $R^4$ is H.

In an exemplary embodiment, the compound is a formula described herein, or a salt, or a hydrate, or a solvate thereof, wherein $R^1$ is as described herein, and Z is O; $R^2$ is Cl; $R^3$ is H; and $R^4$ is H. In an exemplary embodiment, the compound is a formula described herein, or a salt, or a hydrate, or a solvate thereof, wherein $R^1$ is as described herein, and Z is NH; $R^2$ is Cl; $R^3$ is H; and $R^4$ is H. In an exemplary embodiment, the compound is a formula described herein, or a salt, or a hydrate, or a solvate thereof, wherein $R^1$ is as described herein, and Z is $CH_2$; $R^2$ is Cl; $R^3$ is H; and $R^4$ is H.

In an exemplary embodiment, the compound is a formula described herein, or a salt, or a hydrate, or a solvate thereof, wherein $R^1$ is as described herein, and Z is O; $R^2$ is Br; $R^3$ is H; and $R^4$ is H. In an exemplary embodiment, the compound is a formula described herein, or a salt, or a hydrate, or a solvate thereof, wherein $R^1$ is as described herein, and Z is NH; $R^2$ is Br; $R^3$ is H; and $R^4$ is H. In an exemplary embodiment, the compound is a formula described herein, or a salt, or a hydrate, or a solvate thereof, wherein $R^1$ is as described herein, and Z is $CH_2$; $R^2$ is Br; $R^3$ is H; and $R^4$ is H.

In an exemplary embodiment, the compound is a formula described herein, or a salt, or a hydrate, or a solvate thereof, wherein $R^1$ is as described herein, and Z is O; $R^2$ is $CH_3$; $R^3$ is H; and $R^4$ is H. In an exemplary embodiment, the compound is a formula described herein, or a salt, or a hydrate, or a solvate thereof, wherein $R^1$ is as described herein, and Z is NH; $R^2$ is $CH_3$; $R^3$ is H; and $R^4$ is H. In an exemplary embodiment, the compound is a formula described herein, or a salt, or a hydrate, or a solvate thereof, wherein $R^1$ is as described herein, and Z is $CH_2$; $R^2$ is $CH_3$; $R^3$ is H; and $R^4$ is H.

In an exemplary embodiment, the compound is a formula described herein, or a salt, or a hydrate, or a solvate thereof, wherein $R^1$ is as described herein, and Z is O; $R^2$ is H or Cl or Br or $CH_3$; $R^3$ is H or F or Cl or $CH_3$; and $R^4$ is H or F or Cl or CH$_3$. In an exemplary embodiment, the compound is a formula described herein, or a salt, or a hydrate, or a solvate thereof, wherein R$^1$ is as described herein, and Z is NH; R$^2$ is H or Cl or Br or CH$_3$; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is CH$_2$; R$^2$ is H or Cl or Br or CH$_3$; R$^3$ is H or F or Cl or CH$_3$; and R$^4$ is H or F or Cl or CH$_3$.

In an exemplary embodiment, the compound is a formula described herein, or a salt, or a hydrate, or a solvate thereof, wherein R$^1$ is as described herein, and Z is O; R$^2$ is H; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is NH; R$^2$ is H; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is CH$_2$; R$^2$ is H; R$^3$ is H or F or Cl or CH$_3$; and R$^4$ is H or F or Cl or CH$_3$.

In an exemplary embodiment, the compound is a formula described herein, or a salt, or a hydrate, or a solvate thereof, wherein R$^1$ is as described herein, and Z is O; R$^2$ is Cl; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is NH; R$^2$ is Cl; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is CH$_2$; R$^2$ is Cl; R$^3$ is H or F or Cl or CH$_3$; and R$^4$ is H or F or Cl or CH$_3$.

In an exemplary embodiment, the compound is a formula described herein, or a salt, or a hydrate, or a solvate thereof, wherein R$^1$ is as described herein, and Z is O; R$^2$ is Br; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is NH; R$^2$ is Br; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is CH$_2$; R$^2$ is Br; R$^3$ is H or F or Cl or CH$_3$; and R$^4$ is H or F or Cl or CH$_3$.

In an exemplary embodiment, the compound is a formula described herein, or a salt, or a hydrate, or a solvate thereof, wherein R$^1$ is as described herein, and Z is O; R$^2$ is CH$_3$; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is NH; R$^2$ is CH$_3$; R$^3$ is H or F or Cl or CH$_3$; and R$^4$ is H or F or Cl or CH$_3$. In an exemplary embodiment, the compound is a formula described herein, or a salt, or a hydrate, or a solvate thereof, wherein R$^1$ is as described herein, and Z is CH$_2$; R$^2$ is CH$_3$; R$^3$ is H or F or Cl or CH$_3$; and R$^4$ is H or F or Cl or CH$_3$.

In an exemplary embodiment, the compound is a formula described herein, or a salt, or a hydrate, or a solvate thereof, wherein R$^1$ is as described herein, and Z is O; R$^2$ is H or Cl or Br or CH$_3$; R$^3$ is F or Cl or CH$_3$; and R$^4$ is H. In an exemplary embodiment, the compound is a formula described herein, or a salt, or a hydrate, or a solvate thereof, wherein R$^1$ is as described herein, and Z is NH; R$^2$ is H or Cl or Br or CH$_3$; R$^3$ is F or Cl or CH$_3$; and R$^4$ is H. In an exemplary embodiment, the compound is a formula described herein, or a salt, or a hydrate, or a solvate thereof, wherein R$^1$ is as described herein, and Z is CH$_2$; R$^2$ is H or Cl or Br or CH$_3$; R$^3$ is F or Cl or CH$_3$; and R$^4$ is H.

In an exemplary embodiment, the compound is a formula described herein, or a salt, or a hydrate, or a solvate thereof, wherein R$^1$ is as described herein, and Z is O; R$^2$ is H or Cl or Br or CH$_3$; R$^3$ is F or Cl or CH$_3$; and R$^4$ is F or Cl or CH$_3$. In an exemplary embodiment, the compound is a formula described herein, or a salt, or a hydrate, or a solvate thereof, wherein R$^1$ is as described herein, and Z is NH; R$^2$ is H or Cl or Br or CH$_3$; R$^3$ is F or Cl or CH$_3$; and R$^4$ is F or Cl or CH$_3$. In an exemplary embodiment, the compound is a formula described herein, or a salt, or a hydrate, or a solvate thereof, wherein R$^1$ is as described herein, and Z is CH$_2$; R$^2$ is H or Cl or Br or CH$_3$; R$^3$ is F or Cl or CH$_3$; and R$^4$ is F or Cl or CH$_3$.

In an exemplary embodiment, the compound is a formula described herein, or a salt, or a hydrate, or a solvate thereof, wherein R$^1$ is as described herein, and Z is O; R$^2$ is H or Cl or Br or CH$_3$; R$^3$ is F or Cl; and R$^4$ is F or Cl. In an exemplary embodiment, the compound is a formula described herein, or a salt, or a hydrate, or a solvate thereof, wherein R$^1$ is as described herein, and Z is NH; R$^2$ is H or Cl or Br or CH$_3$; R$^3$ is F or Cl; and R$^4$ is F or Cl. In an exemplary embodiment, the compound is a formula described herein, or a salt, or a hydrate, or a solvate thereof, wherein R$^1$ is as described herein, and Z is CH$_2$; R$^2$ is H or Cl or Br or CH$_3$; R$^3$ is F or Cl; and R$^4$ is F or Cl.

In an exemplary embodiment, the compound is a formula described herein, or a salt, or a hydrate, or a solvate thereof, wherein R$^1$ is as described herein, and Z is O; R$^2$ is H or Cl or Br or CH$_3$; R$^3$ is F; and R$^4$ is F. In an exemplary embodiment, the compound is a formula described herein, or a salt, or a hydrate, or a solvate thereof, wherein R$^1$ is as described herein, and Z is NH; R$^2$ is H or Cl or Br or CH$_3$; R$^3$ is F; and R$^4$ is F. In an exemplary embodiment, the compound is a formula described herein, or a salt, or a hydrate, or a solvate thereof, wherein R$^1$ is as described herein, and Z is CH$_2$; R$^2$ is H or Cl or Br or CH$_3$; R$^3$ is F; and R$^4$ is F.

In an exemplary embodiment, the compound is a formula described herein, or a salt, or a hydrate, or a solvate thereof, wherein R$^1$ is as described herein, and Z is O; R$^2$ is H or Cl or Br or CH$_3$; R$^3$ is Cl; and R$^4$ is Cl. In an exemplary embodiment, the compound is a formula described herein, or a salt, or a hydrate, or a solvate thereof, wherein R$^1$ is as described herein, and Z is NH; R$^2$ is H or Cl or Br or CH$_3$; R$^3$ is Cl; and R$^4$ is Cl. In an exemplary embodiment, the compound is a formula described herein, or a salt, or a hydrate, or a solvate thereof, wherein R$^1$ is as described herein, and Z is CH$_2$; R$^2$ is H or Cl or Br or CH$_3$; R$^3$ is Cl; and R$^4$ is Cl.

In an exemplary embodiment, the compound is a formula described herein, or a salt, or a hydrate, or a solvate thereof, wherein R$^1$ is as described herein, and Z is O; R$^2$ is H; R$^3$ is F; and R$^4$ is H. In an exemplary embodiment, the compound is a formula described herein, or a salt, or a hydrate, or a solvate thereof, wherein R$^1$ is as described herein, and Z is NH; R$^2$ is H; R$^3$ is F; and R$^4$ is H. In an exemplary embodiment, the compound is a formula described herein, or a salt, or a hydrate, or a solvate thereof, wherein R$^1$ is as described herein, and Z is CH$_2$; R$^2$ is H; R$^3$ is F; and R$^4$ is H.

In an exemplary embodiment, the compound is a formula described herein, or a salt, or a hydrate, or a solvate thereof, wherein R$^1$ is as described herein, and Z is O; R$^2$ is H; R$^3$ is F; and R$^4$ is F. In an exemplary embodiment, the compound is a formula described herein, or a salt, or a hydrate, or a solvate thereof, wherein $R^1$ is as described herein, and Z is NH; $R^2$ is H; $R^3$ is F; and $R^4$ is F. In an exemplary embodiment, the compound is a formula described herein, or a salt, or a hydrate, or a solvate thereof, wherein $R^1$ is as described herein, and Z is $CH_2$; $R^2$ is H; $R^3$ is F; and $R^4$ is F.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

III.b) Combinations Comprising Additional Therapeutic Agents

The compounds of the invention may also be used in combination with additional therapeutic agents. The invention thus provides, in a further aspect, a combination comprising a compound of the invention together with at least one additional therapeutic agent. In an exemplary embodiment, the combination comprises a compound described herein or a pharmaceutically acceptable salt thereof together with at least one additional therapeutic agent. In an exemplary embodiment, the additional therapeutic agent is a compound of the invention. In an exemplary embodiment, the combination comprises: a) a compound of the invention and b) a first additional therapeutic agent. In an exemplary embodiment, the combination comprises: a) a compound of the invention; b) a first additional therapeutic agent; and c) a second additional therapeutic agent. In an exemplary embodiment, the combination comprises: a) a compound of the invention; b) a first additional therapeutic agent; c) a second additional therapeutic agent; and d) a third additional therapeutic agent. In an exemplary embodiment, the combination comprises: a) a compound of the invention according to Formula (I) and b) a first additional therapeutic agent. In an exemplary embodiment, the combination comprises: a) a compound of the invention according to Formula (I); b) a first additional therapeutic agent; and c) a second additional therapeutic agent.

When a compound of the invention is used in combination with at least one additional therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician.

In an exemplary embodiment, the additional therapeutic agent is useful in treating cancer. In an exemplary embodiment, the additional therapeutic agent is cisplatin. In an exemplary embodiment, the additional therapeutic agent is paclitaxel.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

Compounds described herein can be converted into hydrates and solvates by methods similar to those described herein.

IV. Methods of Inhibiting PARP1 and/or ABL1 and/or ABL2 and/or Tubulin

The compounds of the invention inhibit one or more proteins, and said one or more proteins are PARP1 and/or ABL1 and/or ABL2 and/or tubulin, and therefore have the potential to treat diseases in which these proteins are associated.

In a further aspect, the invention provides a method of inhibiting PARP1 and/or ABL1 and/or ABL2 and/or tubulin, said method comprising: contacting said PARP1 and/or ABL1 and/or ABL2 and/or tubulin with an effective amount of a compound of the invention, thereby inhibiting said PARP1 and/or ABL1 and/or ABL2 and/or tubulin. In an exemplary embodiment, the one or more proteins is one protein which is PARP1. In an exemplary embodiment, the one or more proteins is one protein which is ABL1. In an exemplary embodiment, the one or more proteins is one protein which is ABL2. In an exemplary embodiment, the one or more proteins is one protein which is tubulin. In an exemplary embodiment, the one or more proteins are two proteins which are PARP1 and tubulin. In an exemplary embodiment, the one or more proteins are two proteins which are PARP1 and ABL1. In an exemplary embodiment, the one or more proteins are two proteins which are PARP1 and ABL2. In an exemplary embodiment, the one or more proteins are two proteins which are ABL1 and tubulin. In an exemplary embodiment, the one or more proteins are two proteins which are ABL2 and tubulin. In an exemplary embodiment, the one or more proteins are three proteins which are PARP1, ABL2, and tubulin. In an exemplary embodiment, the one or more proteins are three proteins which are PARP1, ABL1, and tubulin.

V. Methods of Treating Disease

The compounds of the invention exhibit potency against disease, such as cancer, and therefore have the potential to achieve therapeutic efficacy in the animals described herein.

In another aspect, the invention provides a method of treating a disease. The method includes administering to the animal a therapeutically effective amount of the compound of the invention, sufficient to treat the disease. In another aspect, the invention provides a method of treating a disease in an animal comprising administering to the animal a therapeutically effective amount of the compound of the invention, wherein the animal is in need of treatment, sufficient to treat the disease. In another aspect, the invention provides a method of treating a disease in an animal comprising administering to the animal a therapeutically effective amount of the compound of the invention, wherein the animal is not otherwise in need of treatment with the compound of the invention, sufficient to treat the disease. In an exemplary embodiment, the disease is cancer. In an exemplary embodiment, the disease is multiple myeloma.

In another exemplary embodiment, the animal is a human or a farm animal or a companion animal. In another exemplary embodiment, the animal is a human. In another exemplary embodiment, the animal is a goat or pig or sheep or horse or cow or bull. In another exemplary embodiment, the animal is a cat or a dog or a rabbit. In another exemplary embodiment, the animal is a mouse.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another exemplary embodiment, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate;

granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat.* B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of infected cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain infected cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 µm column coupled with an Agilent 1050 series VWD UV detector at 210 nm. Conditions: Solvent A:H$_2$O/1% acetonitrile/0.1% HCO$_2$H; Solvent B: methanol.

Proton magnetic resonance ($^1$H NMR) spectra were recorded on a Varian INOVA NMR spectrometer [400 MHz ($^1$H) or 500 MHz ($^1$H)]. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 µL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with frits (1/in, 1/out). The eluent was 0-100% EtOAc in heptane or 0-10% MeOH in CH$_2$Cl$_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

HPLC purification was performed using a 50 mm Varian Dynamax HPLC 21.4 mm Microsorb Guard-8 $C_{18}$ column, Dyonex Chromeleon operating system coupled with a Varian Prostar 320 UV-vis detector (254 nm) and a Sedex55 ELS detector. Conditions: Solvent A:H$_2$O/1% acetonitrile/ 0.1% HCO$_2$H; Solvent B: MeOH. The appropriate solvent gradient for purification was determined based on the results of analytical HPLC experiments. The resulting fractions were analyzed, combined as appropriate, and evaporated under reduced pressure to provide purified material.

The following experimental sections illustrate procedures for the preparation of intermediates and methods for the preparation of products according to this invention. It should be evident to those skilled in the art that appropriate substitution of both the materials and methods disclosed herein will produce the examples illustrated below and those encompassed by the scope of the invention.

All solvents used were commercially available and were used without further purification. Reactions were typically run using anhydrous solvents under an inert atmosphere of N$_2$.

Compounds are named using the AutoNom 2000 add-on for MDL ISIS™ Draw 2.5 SP2 or their catalogue name if commercially available.

Starting materials used were either available from commercial sources or prepared according to literature procedures and had experimental data in accordance with those reported.

Example 1

Synthesis of Compounds of the Invention

Scheme 1 depicts the general synthetic routes for compounds of the invention and is not intended to be limiting. Specific examples are described subsequently to this general synthetic description. In the generalizations below, specific reaction conditions or details, for example, added reagents, catalysts, solvents, reaction temperature, and the like are not described. The general routes depicted in conjunction with the specific examples provided contain sufficient information to allow one of ordinary skill in the art to synthesize compounds of the invention.

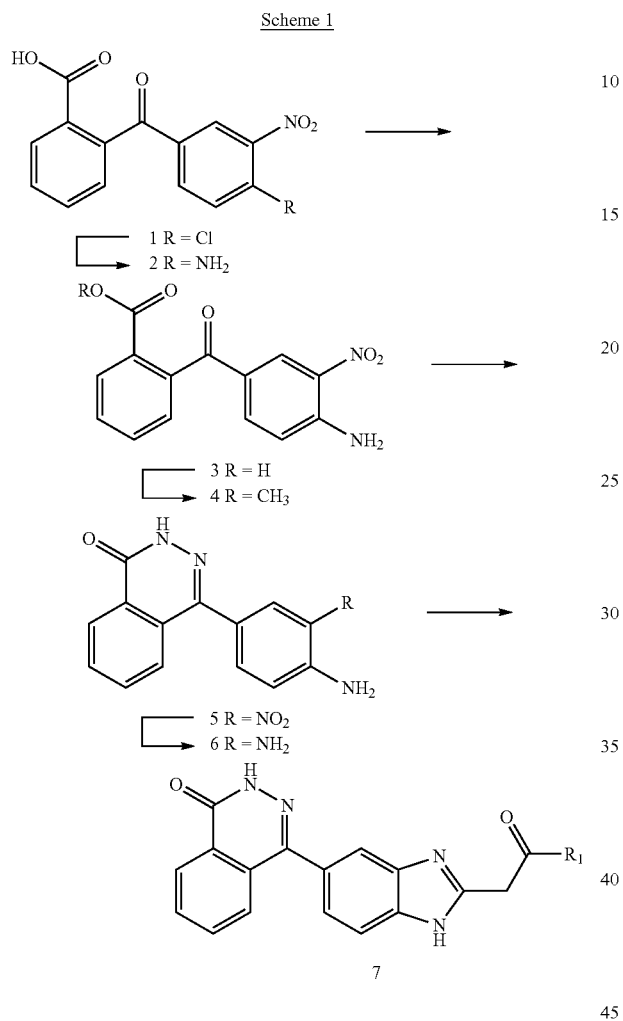

Scheme 1

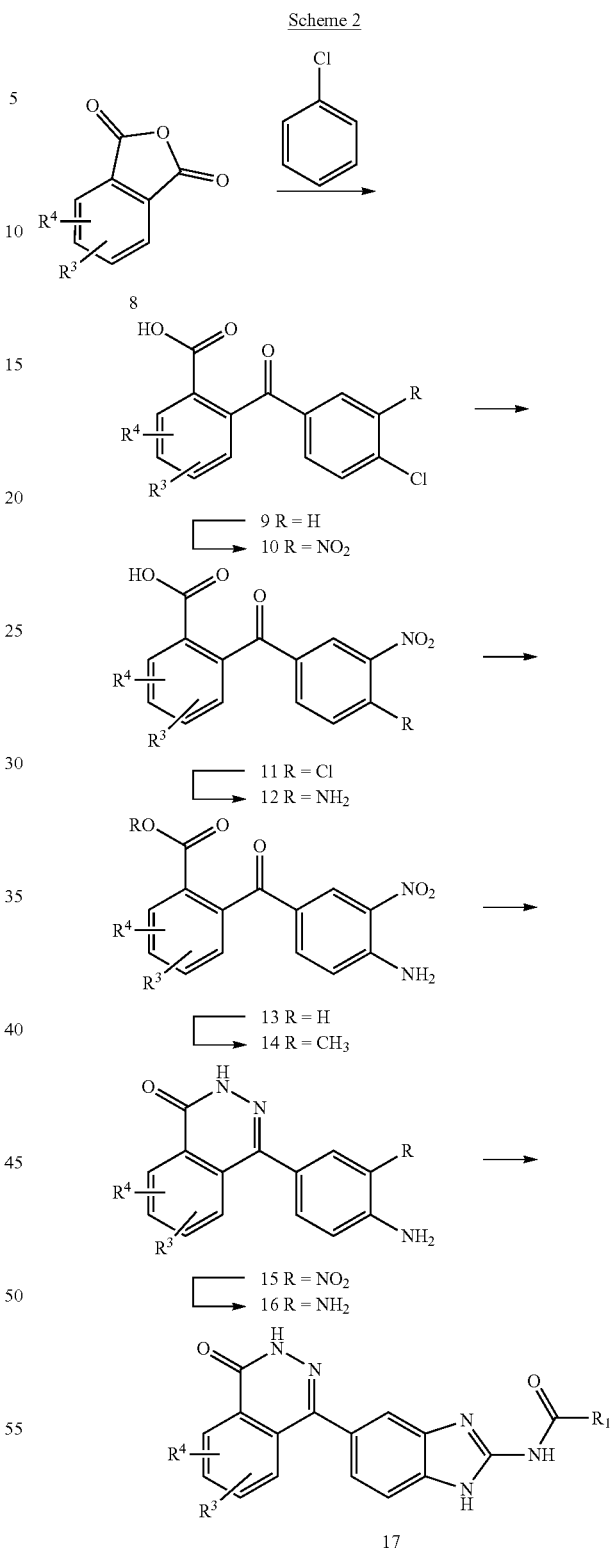

Scheme 2

Compounds of the inventions may also generally be prepared according to the sequence outlined in Scheme 1. For example, 2-(4-chloro-3-nitrobenzoyl)benzoic acid (1) may be converted to (2) in nucleophilic displacement of the chloride with ammonia in an appropriate solvent. Subsequent conversion of the carboxylic acid intermediate, followed by reaction with hydrazine hydrate in an appropriate solvent leads to cyclic compound (5). Reduction of intermediate (5) may be carried out under a range of conditions for example catalytic hydrogenation or hydrogen transfer may be employed using palladium on carbon, platinum oxide or Raney nickel catalysts. Alternatively, iron metal or tin (II) chloride may also be used as effective reducing agents. Conversion of the resulting phenylenediamine (6) to benzimidazole (7) can be achieved in one step for example treating (6) with 1,3-bis(methoxycarbonyl)-2-methyl-2-thiopseudourea in acetic acid with heating. Alternatively, the conversion to (6) may be carried out by treatment first with methoxycarbonyl isothiocyanate following by heating in the presence of an appropriate carbodiimide. To introduce other carbamates, ureas or amides at the benzimidazole 2-position the thiopseudourea reagent of choice may be straightforwardly prepared.

In an alternative synthetic approach depicted in Scheme 2 compounds of the invention may be prepared via electrophilic aromatic substitution of a suitable precursor such as a optionally substituted cyclic anhydride (8) with a substituted aromatic fragment in a regio-selective manner to afford an intermediate (9). Nitration of intermediate (9), followed by subsequent modifications described for the synthesis of (7) afford alternatively substituted derivatives of (17).
Compound No. 11.

Ethyl(5-(6,7-difluoro-4-oxo-3,4-dihydrophthalazin-1-yl)-1H-benzimidazol-2-yl)carbamate STEP 1 To a solution of 4,5-difluorophthalic anhydride (5.0 g, 27.16 mmol) in 1,1,2,2-tetrachloroethane (25 mL) chlorobenzene (3.4 mL, 30.56 mmol) was added followed by the addition of aluminum chloride (7.25 g, 54.32 mmol). The reaction mixture was stirred at 80° C. overnight. Cooling it to room temperature the mixture was poured into ice water (500 mL) and extracted with ethyl acetate (2×300 mL). The organic layer was separated and washed with 2M aqueous hydrochloric acid. (150 mL) and brine (2×150 mL), dried over anhydrous sodium sulfate, the solvent was concentrated to give crude 2-(4-chlorobenzoyl)-4,5-difluorobenzoic acid MS [ESI] for $C_{14}H_7ClF_2O_3$: 295 (M⁻). The crude solid was dissolved in a mixture of methanol (250 mL) and concentrated sulfuric acid (10 mL) and heated to reflux overnight. The reaction mixture was cooled to room temperature and the solvent was concentrated, partitioned with ethyl acetate (300 mL) and water (150 ml). The organic layer was separated, washed with water (2×150 mL), 2M aqueous sodium hydroxide. (2×150 mL) and brine (2×150 mL), dried over anhydrous sodium sulfate and concentrated. The resulting crude product was purified by gradient silica gel flash chromatography (hexane: ethyl acetate) to give methyl 2-(4-chlorobenzoyl)-4,5-difluorobenzoate (6.3 g, 75%). 1H-NMR (300 MHz, d₆-DMSO): 7.82 (d, 2H), 7.71 (d, 1H), 7.52 (d, 2H), 7.42 (d, 1H), 3.86 (s, 3H). MS [ESI] for $C_{15}H_9ClF_2O_3$: 311 (M⁺).

STEP 2 To a solution of methyl 2-(4-chlorobenzoyl)-4,5-difluorobenzoate (6.2 g, 20.00 mmol) in a mixture of tetrahydrofuran (120 mL), methanol (60 mL) and water (10 mL) was added 4M aqueous potassium hydroxide (10 mL, 40.00 mmol) and the reaction mixture was stirred at 64° C. overnight. It was cooled to room temperature and the solvent was concentrated. The pH was adjusted to 2 by the addition of 6N aqueous hydrochloric acid and partitioned with ethyl acetate (300 mL) and water (100 ml). The organic layer was separated, washed with brine (2×250 mL), dried over anhydrous sodium sulfate and concentrated. The precipitated white solid was collected by filtration to give 2-(4-chlorobenzoyl)-4,5-difluorobenzoic acid (5.7 g, 96%). MS [ESI] for $C_{14}H_7ClF_2O_3$: 295 (M⁻).

STEP 3 To solution of 2-(4-chlorobenzoyl)-4,5-difluorobenzoic acid (5.2 g, 17.53 mmol) in concentrated sulfuric acid (25 mL) was added dropwise a solution of fuming nitric acid (0.80 ml, 17.53 mmol) in concentrated sulfuric acid (5.0 mL) at 0° C. and the reaction mixture was stirred for an additional three hours. It was poured onto crushed ice; the precipitated product was collected by filtration. The crude was partitioned with ethyl acetate (300 mL) and water (100 mL), the organic layer was separated and washed with water (2×150 mL) and brine (250 mL) dried over anhydrous sodium sulfate and concentrated. The resulting crude product was triturated with hexanes and the solid was collected by filtration to give 2-(4-chloro-3-nitrobenzoyl)-4,5-difluorobenzoic acid (4.6 g, 77%). 1H-NMR (300 MHz, d₆-DMSO): 12.98 (s, 1H), 8.28 (s, 1H), 8.25 (d, 1H), 7.91 (d, 1H), 7.86 (d, 1H), 7.72 (d, 1H). MS [ESI] for $C_{14}H_6ClF_2NO_5$: 340 (M⁻), 341(M).

STEP 4 A slurry of 2-(4-chloro-3-nitrobenzoyl)-4,5-difluorobenzoic acid (4.5 g, 13.17 mmol) in 28-30 wt % aqueous ammonium hydroxide (200 mL) was heated to 80° C. for 72 hours. The solution was cooled to room temperature and the volume was reduced to 50 ml. The pH was adjusted to 5 by the addition of 6N aqueous hydrochloric acid and the yellow precipitate was collected by filtration, washed with water, dried in vacuo to give 2-(4-amino-3-nitrobenzoyl)-4,5-difluorobenzoic acid (4.2 g, 98%). MS [ESI] for $C_{14}H_8F_2N_2O_5$: 322 [M].

STEP 5 A solution of 2-(4-amino-3-nitrobenzoyl)-4,5-difluorobenzoic acid (4.2 g, 13.00 mmol) in a mixture of methanol (250 mL) and concentrated sulfuric acid (10 mL) was heated to reflux overnight. The reaction mixture was cooled to room temperature and the solvent was concentrated, partitioned with ethyl acetate (300 mL) and water (150 ml). The organic layer was washed with water (2×100 mL), 2M aqueous sodium hydroxide. (2×150 mL) and brine (2×150 mL), dried over anhydrous sodium sulfate and concentrated. The resulting crude product was purified by gradient silica gel flash chromatography (hexane: ethyl acetate) to give methyl 2-(4-amino-3-nitrobenzoyl)-4,5-difluorobenzoate (4.2 g, 96%). MS [ESI] for $C_{15}H_{10}F_2N_2O_5$: 337 [MH⁺].

STEP 6 A solution of methyl 2-(4-amino-3-nitrobenzoyl)-4,5-difluorobenzoate (4.2 g, 12.50 mmol) in a mixture of methanol (150 mL) and 50-60 wt % aqueous solution of hydrazine (7.75 mL, 125.0 mmol) was heated to 64° C. for 18 hours. During the reaction a precipitate has formed. The reaction mixture was cooled to room temperature and concentrated. The precipitate was collected by filtration, washed with cold methanol, diethyl ether and hexanes, dried in vacuo to give 4-(4-amino-3-nitrophenyl)-6,7-difluorophthalazin-1(2H)-one (3.7 g, 95%). 1H-NMR (300 MHz, d₆-DMSO): 12.86 (s, 1H), 8.30 (s, 1H), 8.20 (m, 2H), 7.94 (d, 1H), 7.38 (d, 1H). MS [ESI] for $C_{14}H_8F_2N_4O_3$: 319 [MH⁺].

STEP 7 A slurry of 4-(4-amino-3-nitrophenyl)-6,7-difluorophthalazin-1(2H)-one (0.32 g, 1.0 mmol), ammonium formate (1.26 g, 20.0 mmol) and 10% Pd/C (0.10 g, wet) in methanol (50 mL) was stirred at 64 50° C. overnight. The catalyst was filtered off using a pad of Celite and the solvent was concentrated, partitioned with ethyl acetate (150 mL) and saturated aqueous sodium bicarbonate (100 ml). The organic layer was separated, washed with brine (2×100 mL), dried over anhydrous sodium sulfate and concentrated to give 4-(3,4-diaminophenyl)-6,7-difluorophthalazin-1(2H)-one as tan solid. MS [ESI] for $C_{14}H_{10}F_2N_4O$: 289 [MH+]. The crude product was used without further purification.

STEP 8 A solution of 4-(3,4-diaminophenyl)-6,7-difluorophthalazin-1(2H)-one (0.28 g, 1.00 mmol) and 1,3-bis(ethoxycarbonyl)-2-methyl-2-thiopseudourea (0.24 g, 1.00 mmol) in acetic acid (5.0 mL) was stirred at 102° C. for two hours. After cooling the reaction mixture to room temperature it was diluted with water (5 mL) and the pH was adjusted to 8 by the addition of 10N aqueous sodium hydroxide (8.6 mL). The white precipitate was collected by filtration, washed with water and dried in vacuo. The crude product was suspended in a mixture of ethyl acetate (50 mL) and ethanol (5 mL), heated to reflux. After cooling to room temperature the off white solid was collected by filtration to give ethyl(5-(6,7-difluoro-4-oxo-3,4-dihydrophthalazin-1-yl)-1H-benzimidazol-2-yl)carbamate (0.16 g, 42%). 1H-NMR (300 MHz, d₆-DMSO): 12.94 (s, 1H), 11.82 (br s, 2H), 8.20 (d, 1H), 8.08 (m, 2H), 7.94 (d, 1H), 7.68 (d, 1H), 4.22 (q, 2H), 1.26 (t, 3H). MS [ESI] for $C_{18}H_{13}F_2N_5O_3$: 386 [MH⁺].

Using the same technique and substituting with alternative reagents the following compounds of the invention were prepared:

Scheme 3

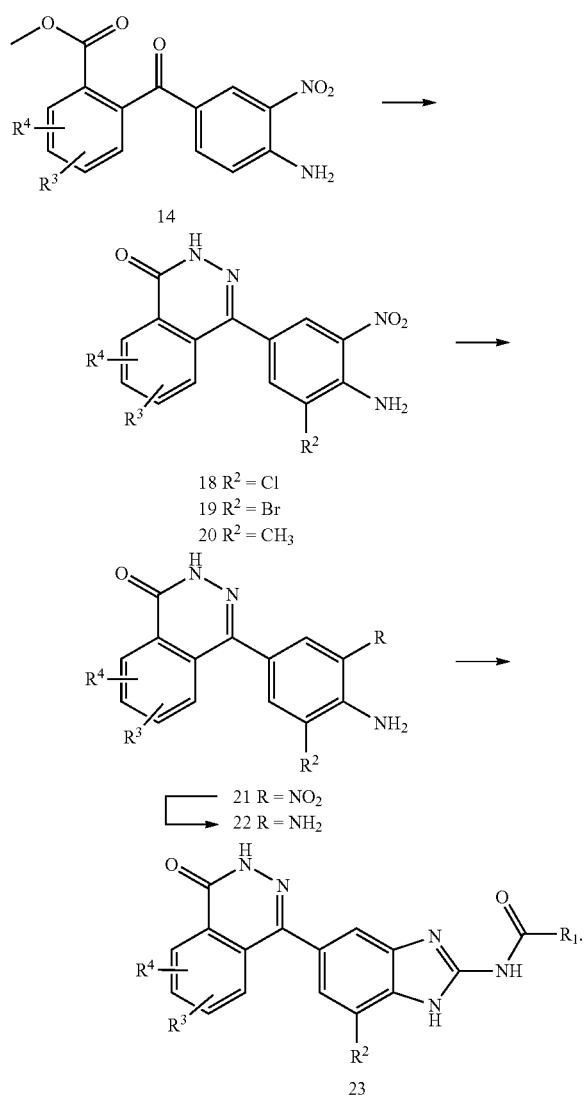

18 R² = Cl
19 R² = Br
20 R² = CH₃

21 R = NO₂
22 R = NH₂

23

In certain cases additional substituent (R²) may be introduced to the benzimidazole aromatic ring using N-Chlorosuccinimide (NCS) for (18) or N-Bromorosuccinimide (NBS) for (19). Additional elaboration of (19) using palladium mediated carbon-carbon bond formation reactions may afford (20). Conversion of these intermediates using synthetic steps described for the synthesis of (7) affords additionally substituted derivatives of this invention (23), Scheme 3.

Compound No. 145.

STEP 1 To a solution of methyl 2-(4-amino-3-nitrobenzoyl)benzoate (0.60 g, 2.00 mmol) in N,N-dimethylformamid (5 mL) was added N-Bromorosuccinimide (0.36 g, 2.00 mmol) in one portion. The reaction mixture was stirred at room temperature for 18 hours. The mixture was partitioned with ethyl acetate (100 mL) and 1M aqueous hydrochloric acid (50 ml). The organic layer was washed with 1M aqueous hydrochloric acid (50 ml) and brine (2×50 mL), dried over anhydrous sodium sulfate and concentrated. The resulting crude was purified by gradient silica gel flash chromatography (hexane: ethyl acetate) to give methyl 2-(4-amino-3-bromo-5-nitrobenzoyl)benzoate (0.70 g, 92%). 1H-NMR (300 MHz, d₆-DMSO): 8.30 (m, 1H), 8.14 (s, 1H), 8.10 (s, 1H), 7.98 (d, 1H), 7.88 (d, 1H), 7.70 (m, 3H), 3.88 (t, 3H). MS [ESI] $C_{15}H_{11}BrN_2O_5$: 381 [MH⁺].

STEP 2 A solution of methyl 2-(4-amino-3-bromo-5-nitrobenzoyl)benzoate (0.38 g, 1.00 mmol), methylboronic acid (72 mg, 1.20 mmol) and potassium carbonate (0.41 g, 3.00 mmol) in a mixture of 1,4-dioxane (5 mL) and water (0.5 mL) was degassed by repeatedly evacuating then bubbling nitrogen gas through the solution, followed by the addition of dichloro[1,1'-bis(diphenylphosphino)ferrocene]palladium(II) dichloromethane adduct (82 mg, 0.10 mmol) and stirring the reaction mixture at 80° C. overnight, then it was cooled to room temperature and partitioned with ethyl acetate (100 mL) and 1M aqueous hydrochloric acid (50 ml). The organic layer was washed with 1M aqueous hydrochloric acid (50 ml) and brine (2×50 mL), dried over anhydrous sodium sulfate and concentrated. The resulting crude was purified by gradient silica gel flash chromatography (hexane: ethyl acetate) to give methyl 2-(4-amino-3-methyl-5-nitrobenzoyl)benzoate (0.26 g, 84%). MS [ESI] $C_{16}H_{14}N_2O_5$: 315 [MH⁺].

STEP 3 A solution methyl 2-(4-amino-3-methyl-5-nitrobenzoyl)benzoate (0.26 g, 0.82 mmol) in a mixture of methanol (25 mL) and 50-60 wt % aqueous solution of hydrazine (0.50 mL, 8.20 mmol) was heated to 64° C. for 18 hours. The reaction mixture was cooled to room temperature and concentrated. The resulting precipitate was collected by filtration, washed with cold methanol, diethyl ether and hexanes, dried in vacuo to give 4-(4-amino-3-methyl-5-nitrophenyl)phthalazin-1(2H)-one (0.24 g, quantitative). MS [ESI] $C_{15}H_{12}N_4O_3$: 297 [MH⁺]. The crude product was used without further purification.

STEP 4 A slurry of 4-(4-amino-3-methyl-5-nitrophenyl)phthalazin-1(2H)-one (0.24 g, 0.82 mmol), ammonium formate (1.00 g, 16.40 mmol) and 10% Pd/C (0.80 mg, wet) in methanol (50 mL) was refluxed for two hours. The catalyst was filtered and the solvent was concentrated, partitioned with ethyl acetate (150 mL) and saturated aqueous sodium bicarbonate (50 ml). The organic layer was separated, washed with brine (2×100 mL), dried over anhydrous sodium sulfate and concentrated to give 4-(3,4-diamino-5-methylphenyl)phthalazin-1(2H)-one as white solid (0.18 g, 82%). MS [ESI] for $C_{15}H_{14}N_4O$: 267 [MH⁺]. The crude product was used without further purification.

STEP 5 A solution of 4-(3,4-diamino-5-methylphenyl)phthalazin-1(2H)-one (0.13 g, 0.50 mmol) and 1,3-bis(ethoxycarbonyl)-2-methyl-2-thiopseudourea (0.12 g, 0.50 mmol) in acetic acid (5.0 mL) was stirred at 98° C. overnight. After cooling the mixture to room temperature it was diluted with water (5 mL) and the pH was adjusted to 8 by the addition of 10N aqueous sodium hydroxide (8.6 mL). The white precipitate was collected by filtration, washed with water and dried in vacuo. The crude product was triturated with ethyl acetate (50 mL). The white solid was collected by filtration to give ethyl(7-methyl-5-(4-oxo-3,4-dihydrophthalazin-1-yl)-1H-benzimidazol-2-yl)carbamate (78 mg, 43%). 1H-NMR (300 MHz, d₆-DMSO): 13.42 (s, 1H), 12.02 (br s, 2H), 8.18 (d, 1H), 7.98 (m, 2H), 7.80 (m, 2H), 7.70 (m, 1H), 4.20 (q, 2H), 1.98 (s, 3H), 1.26 (t, 3H). MS [ESI] for $C_{19}H_{17}N_5O_3$: 364 [MH⁺].

Scheme 4

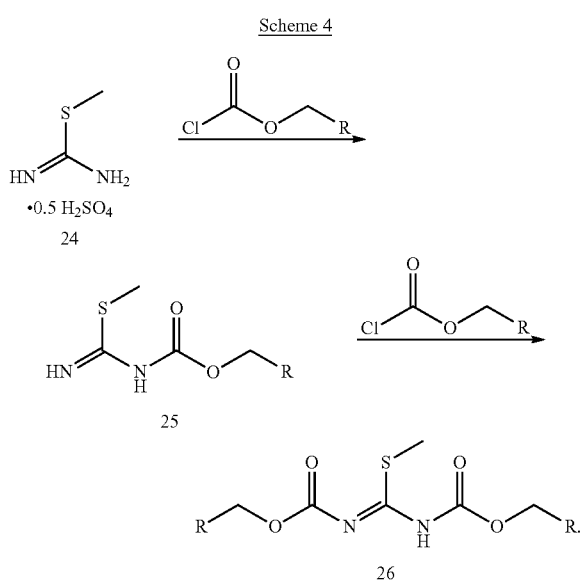

In some cases it may be desired to introduce a variety of carbamate, amide or urea groups at the benzimidazole 2-position. In such an instance, the thiopsueudourea reagent of choice may be straightforwardly prepared according to the two step method illustrated in Scheme 4. For example, reaction of a chloroformate with 2-methyl-2-thiopseudourea hemi sulfate (24) under aqueous or non-aqueous basic conditions affords mono-substituted 2-methyl-2-thiopsueudourea (25) followed by conversion to a di-substituted 2-methyl-2-thiopseudourea reagent (26) which reacts with phenylenediamines to give compounds of the invention. Alternatively, acid chlorides and anhydrides, activated ester, isocyanates or isothiocyanates may also be reacted with 2-methyl-2-thiopseudourea under appropriate conditions to afford di-substituted 2-methyl-2-thiopsueudourea reagents similar to (26). Mono-substituted derivatives such as (25) may also be useful in the synthesis of functionalized 2-aminobenzimidazoles.

Reagent Synthesis 1,3-bis(ethoxycarbonyl)-2-methyl-2-thiopseudourea

To a suspension of 2-methyl-2-thiopseudourea hemi sulfate (4.56 g, 16.40 mmol) and sodium bicarbonate (6.90 g, 82.00 mmol) in a mixture of water (30 mL) and tetrahydrofuran (20 mL) was added dropwise a solution of ethyl chloroformate (3.30 mL, 34.40 mmol) in tetrahydrofuran (20 mL) at 0° C. in a course of two hours and was stirred overnight at room temperature. The solvent was concentrated, and the residue was partitioned with ethyl acetate (400 mL) and water (250 ml). The organic layer was washed with water (2×150 mL) and brine (2×250 mL), dried over anhydrous sodium sulfate and concentrated to give 1-ethoxycarbonyl-2-methyl-2-thiopseudourea (2.70 g). The resulting crude product was used without further purification.

To a solution of 1-ethoxycarbonyl-2-methyl-2-thiopseudourea (2.70 g, 16.40 mmol) and triethylamine (4.60 mL, 32.80 mmol) in tetrahydrofuran (30 mL) was added dropwise a solution of ethyl chloroformate (1.70 mL, 17.40 mmol) in tetrahydrofuran (20 mL) at 0° C. and was stirred overnight at room temperature. It was partitioned with ethyl acetate (400 mL) and 1M aqueous hydrochloric acid (150 ml). The organic layer was washed with 1M aqueous hydrochloric acid (2×150 mL) and brine (2×250 mL), dried over anhydrous sodium sulfate and concentrated. The resulting crude product was purified by gradient silica gel flash chromatography (hexane: ethyl acetate) to give 1,3-bis (ethoxycarbonyl)-2-methyl-2-thiopseudourea as an oil (solidifies to white solid upon standing) (3.65 g, 95%). 1H-NMR (300 MHz, $d_6$-DMSO): 4.22 (m, 4H), 2.48 (s, 3H), 1.32 (m, 6H). MS [ESI] for $C_8H_{14}N_2O_4S$: 235 [MH$^+$].

Using the same technique and substituting with alternative reagents the following compounds of the invention were prepared:

1,3-bis(isobutyloxycarbonyl)-2-methyl-2-thiopseudourea: 1H-NMR (300 MHz, $d_6$-DMSO): 3.94 (d, 2H), 3.90 (d, 2H), 2.48 (s, 3H), 1.98-1.92 (m, 2H), 0.98-0.92 (m, 12H). MS [ESI] for $C_{12}H_{22}N_2O4S$: 291 [MH$^+$].

1,3-bis(methoxyethoxycarbonyl)-2-methyl-2-thiopseudourea: 1H-NMR (300 MHz, $d_6$-DMSO): 4.28 (m, 2H), 4.20 (m, 2H), 3.64 (m, 4H), 3.40 (s, 6H), 2.48 (s, 3H). MS [ESI] for $C_{10}H_{18}H_2O_6S$: 295 [MH$^+$].

1,3-bis(2-chloroethoxycarbonyl)-2-methyl-2-thiopseudourea: 1H-NMR (300 MHz, $d_6$-DMSO): 4.44 (m, 2H), 4.36 (m, 2H), 3.92 (m, 4H), 2.48 (s, 3H). MS [ESI] for $C_8H_{12}Cl_2N_2O_4S$: 303 [MH$^+$].

1,3-bis(3-chloropropyloxycarbonyl)-2-methyl-2-thiopseudourea: 1H-NMR (300 MHz, $d_6$-DMSO): 4.20 (m, 2H), 4.12 (m, 2H), 3.70 (m, 4H), 2.48 (s, 3H), 1.84 (m, 4H). MS [ESI] for $C_{10}H_{16}Cl_2N_2O_4S$: 331 [MH$^+$].

methyl N,N'-bis[(propyl)carbonyl] imidothiocarbamate: 1H-NMR (300 MHz, $d_6$-DMSO): 2.48 (s, 3H), 2.36 (m, 4H), 1.68 (m, 4H), 0.98 (m, 6H). MS [ESI] for $C_8H_{12}Cl_2N_2O_4S$: 303 [MH$^+$].

methyl N,N'-bis[(methoxymethyl)carbonyl]imidothiocarbamate: 1H-NMR (300 MHz, $d_6$-DMSO): 4.48 (s, 2H), 4.28 (s, 2H), 3.34 (s, 3H), 3.30 (s, 3H), 2.48 (s, 3H). MS [ESI] for $C_8H_{14}N_2O_4S$: 235 [MH$^+$].

N,N'-bis[(ethylamino)-carbonyl]carbamimidothioic acid methyl ester: 1H-NMR (300 MHz, $d_6$-DMSO): 3.24 (q, 2H), 3.08 (q, 2H), 2.46 (s, 3H), 1.12 (m, 6H). MS [ESI] for $C_8H_{16}N_4O_2S$: 233 [MH$^+$].

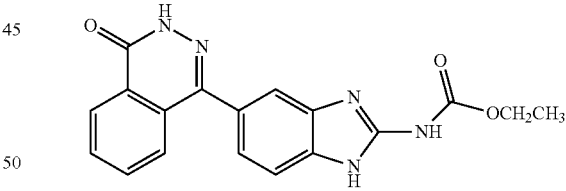

1. Ethyl(5-(4-oxo-3,4-dihydrophthalazin-1-yl)-1H-benzimidazol-2-yl)carbamate Hemi-Acetate or Ethyl(5-(4-oxo-3,4-dihydrophthalazin-1-yl)-1H-benzo[d]imidazol-2-yl)carbamate A solution of 2-(4-chloro-3-nitrobenzoyl)benzoic acid (5.0 g, 16.36 mmol) in 28-30 wt % aqueous ammonium hydroxide (200 mL) was heated to 80° C. for 72 hours. The solution was cooled to room temperature and it was concentrated to 25 ml. The pH was adjusted to 7 by the addition of 6N aqueous hydrochloric acid and the yellow precipitate was collected by filtration, washed with water, dried in vacuo to give 2-(4-amino-3-nitrobenzoyl)benzoic acid (4.4 g, 94%). MS [ESI] for $C_{14}H_{10}N_2O_5$: 287 [MH$^+$].

A solution of 2-(4-amino-3-nitrobenzoyl)benzoic acid (4.4 g, 15.37 mmol) I methanol (200 mL) in the presence of catalytic amount of sulfuric acid was heated to reflux for 18 hours. The reaction mixture was cooled to room temperature and the solvent was concentrated. The precipitated yellow solid was collected by filtration, washed with cold methanol and dried in vacuo to provide methyl 2-(4-amino-3-nitrobenzoyl)benzoate (4.5 g, 97%). MS [ESI] for $C_{15}H_{12}N_2O_5$: 301 [MH+].

To a solution of methyl 2-(4-amino-3-nitrobenzoyl)benzoate (0.30 g, 1.0 mmol) in 2-propanol (30 mL) an 50-60 wt % aqueous solution of hydrazine (0.31 mL, 5.0 mmol) was added and it was heated to 80° C. for 18 hours. The solution was cooled to room temperature and concentrated. The precipitate was collected by filtration, washed with methanol and dried in vacuo to give 4-(4-amino-3-nitrophenyl)phthalazin-1(2H)-one (0.28 g, quantitative). MS [ESI] for $C_{14}H_{10}N_4O_3$: 283 [MH+].

A solution of 4-(4-amino-3-nitrophenyl)phthalazin-1(2H)-one (0.28 g, 1.0 mmol) and ammonium formate (0.32 g, 5.0 mmol)) in methanol (30 mL) was stirred in the presence of 10% Pd/C at 50° C. for 18 hours then filtered through a pad of Celite. The Celite was washed with methanol (50 mL) and the solvent was concentrated to provide 4-(3,4-diaminophenyl)phthalazin-1(2H)-one (0.21 g, 84%) as a white solid. MS [ESI] for $C_{14}H_{12}N_4O$: 253 [MH+].

A solution of 4-(3,4-diaminophenyl)phthalazin-1(2H)-one (0.16 g, 0.63 mmol) and 1,3-bis(ethoxycarbonyl)-2-methyl-2-thiopseudourea (0.15 g, 0.63 mmol) in acetic acid (3.0 mL) was stirred at 80° C. for 2 hours, after cooling the mixture to room temperature the white precipitate was collected by filtration, washed with water and ethanol and dried in vacuo to give ethyl(5-(4-oxo-3,4-dihydrophthalazin-1-yl)-1H-benzimidazol-2-yl)carbamate hemiacetate (0.11 g, 52%). 1H-NMR (300 MHz, d₆-DMSO): 12.76 (s, 1H), 11.75 (br s, 2H), 8.33 (m, 1H), 7.87 (m, 1H), 7.75 (m, 2H), 7.60 (d, 1H), 7.53 (d, 1H), 7.27 (dd, 1H), 4.23 (m, 2H), 1.90 (s, 1.5H), 1.29 (t, 3H). MS [ESI] for $C_{18}H_{15}N_5O_3$: 351 [MH+].

Using the same technique and substituting with alternative reagents the following compounds of the invention were prepared:

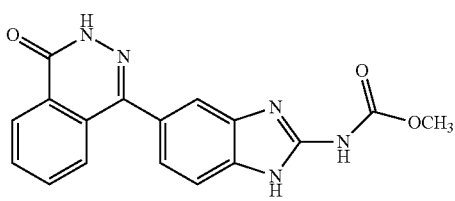 [SMILES: COC(=O)Nc1nc2cc(-c3n[nH]c(=O)c4ccccc34)ccc2[nH]1]

2. Methyl(5-(4-oxo-3,4-dihydrophthalazin-1-yl)-1H-benzimidazol-2-yl)carbamate Hemi-Acetate or Methyl(5-(4-oxo-3,4-dihydrophthalazin-1-yl)-1H-benzo[d]imidazol-2-yl)carbamate 1H-NMR (300 MHz, d₆-DMSO): 12.75 (s, 1H), 11.74 (br s, 2H), 8.32 (m, 1H), 7.87 (m, 3H), 7.68 (m, 3H), 3.73 (s, 3H). MS [ESI] for $C_{17}H_{13}N_5O_3$: 336 [MH+].

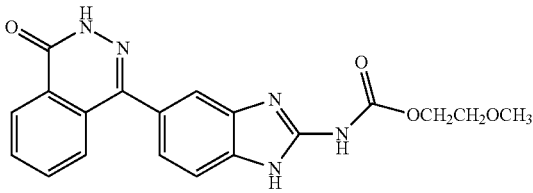

3. 2-Methoxyethyl(5-(4-oxo-3,4-dihydrophthalazin-1-yl)-1H-benzimidazol-2-yl)carbamate or 2-methoxyethyl(5-(4-oxo-3,4-dihydrophthalazin-1-yl)-1H-benzo[d]imidazol-2-yl)carbamate 1H-NMR (300 MHz, d₆-DMSO): 12.77 (s, 1H), 11.76 (br s, 2H), 8.33 (m, 1H), 7.87 (m, 2H), 7.76 (m, 1H), 7.56 (m, 2H), 7.28 (dd, 1H), 4.32 (m, 2H), 3.61 (m, 2H), 3.40 (s, 3H). MS [ESI] for $C_{19}H_{17}N_5O_4$: 380 [MH+].

Using the same technique and substituting with alternative reagents the following compounds of the invention may also be prepared:

Compound No. 4.
Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(methoxycarbonyl)-2-methyl-2-thiopseudourea in step 5.

Compound No. 5.
Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(methoxycarbonyl)-2-methyl-2-thiopseudourea in step 5.

Compound No. 6.
Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(methoxycarbonyl)-2-methyl-2-thiopseudourea in step 5.

Compound No. 7.
Methyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(methoxycarbonyl)-2-methyl-2-thiopseudourea in step 5.

Compound No. 8.
Ethyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(ethoxycarbonyl)-2-methyl-2-thiopseudourea in step 5.

Compound No. 9.
Ethyl(5-(7-fluoro-4-oxo-3,4-dihydrophthalazin-1-yl)-1H-benzimidazol-2-yl)carbamate was prepared using 2-(4-chloro-3-nitrobenzoyl)-4-fluorobenzoic acid in step 1 and 1,3-bis(ethoxycarbonyl)-2-methyl-2-thiopseudourea in step 5. ¹H-NMR (300 MHz, d₆-DMSO): 12.86 (s, 1H), 11.92 (s, 2H), 8.14 (m, 1H), 8.08 (m, 2H), 7.96 (d, 1H), 7.68 (d, 1H), 7.58 (m, 1H), 4.18 (q, 2H), 1.24 (t, 3H). MS [ESI] for $C_{18}H_{14}FN_5O_3$: 368 [MH+].

Compound No. 10.
Ethyl(5-(5,8-difluoro-4-oxo-3,4-dihydrophthalazin-1-yl)-1H-benzimidazol-2-yl)carbamate was prepared using 2-(4-chloro-3-nitrobenzoyl)-3,6-difluorobenzoic acid in step 1 and 1,3-bis(ethoxycarbonyl)-2-methyl-2-thiopseudourea in step 5. ¹H-NMR (300 MHz, d₆-DMSO): 12.82 (s, 1H), 11.90 (s, 2H), 8.06 (m, 2H), 7.68 (d, 1H), 7.58 (m, 1H), 7.54 (m, 1H), 4.20 (q, 2H), 1.26 (t, 3H). MS [ESI] for $C_{18}H_{13}F_2N_5O_3$: 386 [MH⁺].

Compound No. 11.

Ethyl(5-(6,7-difluoro-4-oxo-3,4-dihydrophthalazin-1-yl)-1H-benzimidazol-2-yl)carbamate was prepared using 2-(4-chloro-3-nitrobenzoyl)-4,5-difluorobenzoic acid in step 1 and 1,3-bis(ethoxycarbonyl)-2-methyl-2-thiopseudourea in step 5.

Compound No. 12.

2-Methoxyethyl(5-(8-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(mehoxyethoxycarbonyl)-2-methyl-2-thiopseudourea in step 5.

Compound No. 13.

2-Methoxyethyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(metohyethoxycarbonyl)-2-methyl-2-thiopseudourea in step 5.

Compound No. 14.

2-Methoxyethyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(methoxyyethoxycarbonyl)-2-methyl-2-thiopseudourea in step 5.

Compound No. 15.

2-Methoxyethyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(methoxyethoxycarbonyl)-2-methyl-2-thiopseudourea in step 5.

Compound No. 16.

Methyl(5-(8-chloro-4-oxo-3,4-dihydrophthalazin-1-yl)-1H-benzimidazol-2-yl)carbamate can be prepared using 2-(4-chloro-3-nitrobenzoyl)-3-chlorobenzoic acid in step 1 and 1,3-bis(methoxycarbonyl)-2-methyl-2-thiopseudourea in step 5.

Compound No. 17.

Methyl(5-(7-chloro-4-oxo-3,4-dihydrophthalazin-1-yl)-1H-benzimidazol-2-yl)carbamate can be prepared using 2-(4-chloro-3-nitrobenzoyl)-4-chlorobenzoic acid in step 1 and 1,3-bis(methoxycarbonyl)-2-methyl-2-thiopseudourea in step 5.

Compound No. 18.

Methyl(5-(5,8-dichloro-4-oxo-3,4-dihydrophthalazin-1-yl)-1H-benzimidazol-2-yl)carbamate can be prepared using 2-(4-chloro-3-nitrobenzoyl)-3,6-dichlorobenzoic acid in step 1 and 1,3-bis(methoxycarbonyl)-2-methyl-2-thiopseudourea in step 5.

Compound No. 19.

Methyl(5-(6,7-dichloro-4-oxo-3,4-dihydrophthalazin-1-yl)-1H-benzimidazol-2-yl)carbamate can be prepared using 2-(4-chloro-3-nitrobenzoyl)-4,5-dichlorobenzoic acid in step 1 and 1,3-bis(methoxycarbonyl)-2-methyl-2-thiopseudourea in step 5.

Compound No. 20.

Ethyl(5-(8-chloro-4-oxo-3,4-dihydrophthalazin-1-yl)-1H-benzimidazol-2-yl)carbamate was prepared using 2-(4-chloro-3-nitrobenzoyl)-3-chlorobenzoic acid in step 1 and 1,3-bis(ethoxycarbonyl)-2-methyl-2-thiopseudourea in step 5. ¹H-NMR (300 MHz, d₆-DMSO): 12.86 (s, 1H), 11.94 (s, 2H), 8.08-8.04 (m, 3H), 7.78 (d, 1H) 7.70 (m, 1H), 7.68 (m, 1H), 4.17 (q, 2H), 1.24 (t, 3H). MS [ESI] for $C_{18}H_{14}ClN_5O_3$: 384 [MH⁺].

Compound No. 21.

Ethyl(5-(7-chloro-4-oxo-3,4-dihydrophthalazin-1-yl)-1H-benzimidazol-2-yl)carbamate was prepared using 2-(4-chloro-3-nitrobenzoyl)-4-chlorobenzoic acid in step 1 and 1,3-bis(ethoxycarbonyl)-2-methyl-2-thiopseudourea in step 5. ¹H-NMR (300 MHz, d₆-DMSO): 12.87 (s, 1H), 11.94 (s, 2H), 8.12-8.10 (m, 2H), 8.06 (m, 2H), 7.68 (m, 2H), 4.20 (q, 2H), 1.26 (t, 3H). MS [ESI] for $C_{18}H_{14}ClN_5O_3$: 384 [MH⁺].

Compound No. 22.

Ethyl(5-(5,8-dichloro-4-oxo-3,4-dihydrophthalazin-1-yl)-1H-benzimidazol-2-yl)carbamate was prepared using 2-(4-chloro-3-nitrobenzoyl)-3,6-dichlorobenzoic acid in step 1 and 1,3-bis(ethoxycarbonyl)-2-methyl-2-thiopseudourea in step 5. ¹H-NMR (300 MHz, d₆-DMSO): 12.86 (s, 1H), 11.92 (s, 2H), 8.06 (m, 2H), 7.72 (d, 1H), 7.68 (m, 1H), 7.62 (m, 1H), 4.18 (q, 2H), 1.26 (t, 3H). MS [ESI] for $C_{18}H_{13}Cl_2N_5O_3$: 418 [MH⁺].

Compound No. 23.

Ethyl(5-(6,7-dichloro-4-oxo-3,4-dihydrophthalazin-1-yl)-1H-benzimidazol-2-yl)carbamate was prepared using 2-(4-chloro-3-nitrobenzoyl)-4,5-dichlorobenzoic acid in step 1 and 1,3-bis(ethoxycarbonyl)-2-methyl-2-thiopseudourea in step 5. ¹H-NMR (300 MHz, d₆-DMSO): 12.96 (s, 1H), 11.94 (s, 2H), 8.20 (d, 1H), 8.08 (m, 2H), 8.04 (s, 1H), 7.68 (d, 1H), 4.18 (q, 2H), 1.26 (t, 3H). MS [ESI] for $C_{18}H_{13}Cl_2N_5O_3$: 418 [MH⁺].

Compound No. 24.

2-Methoxyethyl(5-(8-chloro-4-oxo-3,4-dihydrophthalazin-1-yl)-1H-benzimidazol-2-yl)carbamate can be prepared using 2-(4-chloro-3-nitrobenzoyl)-3-chlorobenzoic acid in step 1 and 1,3-bis(metoxyethoxycarbonyl)-2-methyl-2-thiopseudourea in step 5.

Compound No. 25.

2-Methoxyethyl(5-(7-chloro-4-oxo-3,4-dihydrophthalazin-1-yl)-1H-benzimidazol-2-yl)carbamate can be prepared using 2-(4-chloro-3-nitrobenzoyl)-4-chlorobenzoic acid in step 1 and 1,3-bis(methoxyethoxycarbonyl)-2-methyl-2-thiopseudourea in step 5.

Compound No. 26.

2-Methoxyethyl(5-(5,8-dichloro-4-oxo-3,4-dihydrophthalazin-1-yl)-1H-benzimidazol-2-yl)carbamate can be prepared using 2-(4-chloro-3-nitrobenzoyl)-3,6-dichlorobenzoic acid in step 1 and 1,3-bis(methoxyethoxycarbonyl)-2-methyl-2-thiopseudourea in step 5.

Compound No. 27.

2-Methoxyethyl(5-(6,7-dichloro-4-oxo-3,4-dihydrophthalazin-1-yl)-1H-benzimidazol-2-yl)carbamate can be prepared using 2-(4-chloro-3-nitrobenzoyl)-4,5-dichlorobenzoic acid in step 1 and 1,3-bis(metoxyethoxycarbonyl)-2-methyl-2-thiopseudourea in step 5.

Compound No. 28.

Methyl(5-(8-methyl-4-oxo-3,4-dihydrophthalazin-1-yl)-1H-benzimidazol-2-yl)carbamate can be prepared using 2-(4-chloro-3-nitrobenzoyl)-3-methylbenzoic acid in step 1 and 1,3-bis(methoxycarbonyl)-2-methyl-2-thiopseudourea in step 5.

Compound No. 29.

Methyl(5-(7-methyl-4-oxo-3,4-dihydrophthalazin-1-yl)-1H-benzimidazol-2-yl)carbamate can be prepared using 2-(4-chloro-3-nitrobenzoyl)-4-methylbenzoic acid in step 1 and 1,3-bis(methoxycarbonyl)-2-methyl-2-thiopseudourea in step 5.

Compound No. 30.

Ethyl(5-(8-methyl-4-oxo-3,4-dihydrophthalazin-1-yl)-1H-benzimidazol-2-yl)carbamate can be prepared using 2-(4-chloro-3-nitrobenzoyl)-3-methylbenzoic acid in step 1 and 1,3-bis(ethoxycarbonyl)-2-methyl-2-thiopseudourea in step 5.

Compound No. 31.
Ethyl(5-(7-methyl-4-oxo-3,4-dihydrophthalazin-1-yl)-1H-benzimidazol-2-yl)carbamate can be prepared using 2-(4-chloro-3-nitrobenzoyl)-4-methylbenzoic acid in step 1 and 1,3-bis(ethoxycarbonyl)-2-methyl-2-thiopseudourea in step 5.

Compound No. 32.
2-Methoxyethyl(5-(8-methyl-4-oxo-3,4-dihydrophthalazin-1-yl)-1H-benzimidazol-2-yl)carbamate can be prepared using 2-(4-chloro-3-nitrobenzoyl)-3-methylbenzoic acid in step 1 and 1,3-bis(methoxyethoxycarbonyl)-2-methyl-2-thiopseudourea in step 5.

Compound No. 33.
2-Methoxyethyl(5-(7-methyl-4-oxo-3,4-dihydrophthalazin-1-yl)-1H-benzimidazol-2-yl)carbamate can be prepared using 2-(4-chloro-3-nitrobenzoyl)-4-methylbenzoic acid in step 1 and 1,3-bis(methoxyethoxycarbonyl)-2-methyl-2-thiopseudourea in step 5.

Compound No. 34.
Isopropyl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1,3-bis(isopropyloxycarbonyl)-2-methyl-2-thiopseudourea in step 5.

Compound No. 35.
Isopropyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(isopropyloxycarbonyl)-2-methyl-2-thiopseudourea in step 5.

Compound No. 36.
Isopropyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(isopropyloxycarbonyl)-2-methyl-2-thiopseudourea in step 5.

Compound No. 37.
Isopropyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(isopropyloxycarbonyl)-2-methyl-2-thiopseudourea in step 5.

Compound No. 38.
Isopropyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(isopropyloxycarbonyl)-2-methyl-2-thiopseudourea in step 5.

Compound No. 39.
tert-Butyl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1,3-bis(tert-butyloxycarbonyl)-2-methyl-2-thiopseudourea in step 5.

Compound No. 40.
tert-Butyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(tert-butyloxycarbonyl)-2-methyl-2-thiopseudourea in step 5.

Compound No. 41.
tert-Butyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(tert-butyloxycarbonyl)-2-methyl-2-thiopseudourea in step 5.

Compound No. 42.
tert-Butyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(tert-butyloxycarbonyl)-2-methyl-2-thiopseudourea in step 5.

Compound No. 43.
tert-butyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(tert-butyloxycarbonyl)-2-methyl-2-thiopseudourea in step 5.

Compound No. 44.
sec-Butyl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1,3-bis(sec-butyloxycarbonyl)-2-methyl-2-thiopseudourea in step 5.

Compound No. 45.
sec-Butyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(sec-butyloxycarbonyl)-2-methyl-2-thiopseudourea in step 5.

Compound No. 46.
sec-Butyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(sec-butyloxycarbonyl)-2-methyl-2-thiopseudourea in step 5.

Compound No. 47.
sec-Butyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(sec-butyloxycarbonyl)-2-methyl-2-thiopseudourea in step 5.

Compound No. 48.
sec-Butyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(sec-butyloxycarbonyl)-2-methyl-2-thiopseudourea in step 5.

Compound No. 49.
Cyclopropyl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1,3 bis(cyclopropyloxycarbonyl)-2-methyl-2-thiopseudourea in step 5.

Compound No. 50.
Cyclopropyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3 bis(cyclopropyloxycarbonyl)-2-methyl-2-thiopseudourea in step 5.

Compound No. 51.
Cyclopropyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3 bis(cyclopropyloxycarbonyl)-2-methyl-2-thiopseudourea in step 5.

Compound No. 52.
Cyclopropyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3 bis(cyclopropyloxycarbonyl)-2-methyl-2-thiopseudourea in step 5.

Compound No. 53.

Cyclopropyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3 bis(cyclopropyloxycarbonyl)-2-methyl-2-thiopseudourea in step 5.

Compound No. 54.

Cyclobutyl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1,3 bis(cyclobutyloxycarbonyl)-2-methyl-2-thiopseudourea in step 5.

Compound No. 55.

Cyclobutyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3 bis(cyclobutyloxycarbonyl)-2-methyl-2-thiopseudourea in step 5.

Compound No. 56.

Cyclobutyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3 bis(cyclobutyloxycarbonyl)-2-methyl-2-thiopseudourea in step 5.

Compound No. 57.

Cyclobutyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3 bis(cyclobutyloxycarbonyl)-2-methyl-2-thiopseudourea in step 5.

Compound No. 58.

Cyclobutyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3 bis(cyclobutyloxycarbonyl)-2-methyl-2-thiopseudourea in step 5.

Compound No. 59.

2-Fluoroethyl(5-(4-oxo-3,4-dihydrophthalazin-1-yl)-1H-benzimidazol-2-yl)carbamate carbamate can be prepared using 2-(4-chloro-3-nitrobenzoyl)benzoic acid in step 1 and 1,3 bis(2-fluoroethoxycarbonyl)-2-methyl-2-thiopseudourea in step 5.

Compound No. 60.

2-Fluoroethyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3 bis(2-fluoroethoxycarbonyl)-2-methyl-2-thiopseudourea in step 5.

Compound No. 61.

2-Fluoroethyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3 bis(2-fluoroethoxycarbonyl)-2-methyl-2-thiopseudourea in step 5.

Compound No. 62.

2-Fluoroethyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3 bis(2-fluoroethoxycarbonyl)-2-methyl-2-thiopseudourea in step 5.

Compound No. 63.

2-Fluoroethyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3 bis(2-fluoroethoxycarbonyl)-2-methyl-2-thiopseudourea in step 5.

Compound No. 64.

2,2-Difluoroethyl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1,3 bis(2,2-difluoroethoxycarbonyl)-2-methyl-2-thiopseudourea in step 5.

Compound No. 65.

2,2-Difluoroethyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3 bis(2,2-difluoroethoxycarbonyl)-2-methyl-2-thiopseudourea in step 5.

Compound No. 66.

2,2-Difluoroethyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3 bis(2,2-difluoroethoxycarbonyl)-2-methyl-2-thiopseudourea in step 5.

Compound No. 67.

2,2-Difluoroethyl(5-(5,8-difluoro-4-oxo-3,4-dihydrophthalazin-1-yl)-1H-benzimidazol-2-yl)carbamate was prepared using 2-(4-chloro-3-nitrobenzoyl)-3,6-difluorobenzoic acid in step 1 and 1,3 bis(2,2-difluoroethoxycarbonyl)-2-methyl-2-thiopseudourea in step 5.

Compound No. 68.

2,2-Difluoroethyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3 bis(2,2-difluoroethoxycarbonyl)-2-methyl-2-thiopseudourea in step 5.

Compound No. 69.

2,2,2-Trifluoroethyl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1,3 bis(2,2,2-trifluoroethoxycarbonyl)-2-methyl-2-thiopseudourea in step 5.

Compound No. 70.

2,2,2-Trifluoroethyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3 bis(2,2,2-trifluoroethoxycarbonyl)-2-methyl-2-thiopseudourea in step 5.

Compound No. 71.

2,2,2-Trifluoroethyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3 bis(2,2,2-trifluoroethoxycarbonyl)-2-methyl-2-thiopseudourea in step 5.

Compound No. 72.

2,2,2-Trifluoroethyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3 bis(2,2,2-trifluoroethoxycarbonyl)-2-methyl-2-thiopseudourea in step 5.

Compound No. 73.

2,2,2-Trifluoroethyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3 bis(2,2,2-trifluoroethoxycarbonyl)-2-methyl-2-thiopseudourea in step 5.

Compound No. 74.

1-Methylazetidin-3-yl(5-(4-oxo-3,4-dihydrophthalazin-1-yl)-1H-benzimidazol-2-yl)carbamate can be prepared using 2-(4-chloro-3-nitrobenzoyl)benzoic acid in step 1 and 1-methylazetidin-3-yl[imino(methylthio)methyl]carbamate in step 5.

Compound No. 75.

1-Methylazetidin-3-yl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1-methylazetidin-3-yl[imino(methylthio)methyl]carbamate in step 5.

Compound No. 76.

1-Methylazetidin-3-yl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1-methylazetidin-3-yl[imino(methylthio)methyl] carbamate in step 5.

Compound No. 77.

1-Methylazetidin-3-yl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1-methylazetidin-3-yl[imino(methylthio)methyl]carbamate in step 5.

Compound No. 78.

1-Methylazetidin-3-yl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1-methylazetidin-3-yl[imino(methylthio)methyl]carbamate in step 5.

Compound No. 79.

1-Methyl-3-(5-(4-oxo-3,4-dihydrophthalazin-1-yl)-1H-benzimidazol-2-yl)urea can be prepared using 2-(4-chloro-3-nitrobenzoyl)benzoic acid in step 1 and N,N'-bis[(methylamino)-carbonyl]carbamimidothioic acid methyl ester in step 5.

Compound No. 80.

1-Ethyl-3-(5-(4-oxo-3,4-dihydrophthalazin-1-yl)-1H-benzimidazol-2-yl)urea was prepared using 2-(4-chloro-3-nitrobenzoyl)benzoic acid in step 1 and N,N'-bis[(ethylamino)-carbonyl]carbamimidothioic acid methyl ester in step 5. $^1$H-NMR (300 MHz, $d_6$-DMSO): 12.82 (s, 1H), 12.26 (s, 1H), 10.84 (s, 1H), 8.28 (d, 1H), 8.12 (s, 1H), 8.08 (d, 1H), 8.02 (d, 1H), 7.78 (m, 1H), 7.68 (m, 2H), 7.23 (s, 1H), 3.24 (m, 2H), 1.08 (t, 3H). MS [ESI] for $C_{18}H_{16}N_6O_2$: 349 [MH$^+$].

Compound No. 81.

1-Isopropyl-3-(5-(4-oxo-3,4-dihydrophthalazin-1-yl)-1H-benzimidazol-2-yl)urea can be prepared using 2-(4-chloro-3-nitrobenzoyl)benzoic acid in step 1 and N,N'-bis[(isopropylamino) carbonyl]carbamimidothioic acid methyl ester in step 5.

Compound No. 82.

1-Cyclopropyl-3-(5-(4-oxo-3,4-dihydrophthalazin-1-yl)-1H-benzimidazol-2-yl)urea can be prepared using 2-(4-chloro-3-nitrobenzoyl)benzoic acid in step 1 and N,N'-bis[(cyclopropylamino)-carbonyl]carbamimidothioic acid methyl ester in step 5.

Compound No. 83.

1,1-Dimethyl-3-(5-(4-oxo-3,4-dihydrophthalazin-1-yl)-1H-benzimidazol-2-yl)urea can be prepared using 2-(4-chloro-3-nitrobenzoyl)benzoic acid in step 1 and N,N'-bis[(1,1-dimetylamino)-carbonyl]carbamimidothioic acid methyl ester in step 5.

Compound No. 84.

N-(5-(4-oxo-3,4-dihydrophthalazin-1-yl)-1H-benzimidazol-2-yl)acetamide can be prepared using 2-(4-chloro-3-nitrobenzoyl)benzoic acid in step 1 and methyl N,N'-bis[(methyl)carbonyl]imidothiocarbamate in step 5.

Compound No. 85.

N-(5-(4-oxo-3,4-dihydrophthalazin-1-yl)-1H-benzimidazol-2-yl)propionamide can be prepared using 2-(4-chloro-3-nitrobenzoyl)benzoic acid in step 1 and methyl N,N'-bis[(ethyl)carbonyl] imidothiocarbamate in step 5.

Compound No. 86.

N-(5-(4-oxo-3,4-dihydrophthalazin-1-yl)-1H-benzimidazol-2-yl)butyramide was prepared using 2-(4-chloro-3-nitrobenzoyl)benzoic acid in step land methyl N,N'-bis[(propyl)carbonyl] imidothiocarbamate in step 5. $^1$H-NMR (300 MHz, $d_6$-DMSO): 12.78 (s, 1H), 12.22 (s, 1H), 11.58 (s, 1H), 8.28 (d, 1H), 7.98 (m, 2H), 7.78 (m, 1H), 7.58 (m, 2H), 7.26 (m, 1H), 2.42 (dd, 2H), 1.66 (m, 2H), 0.94 (t, 3H). MS [ESI] for $C_{19}H_{17}N_5O_2$: 348 [MH$^+$].

Compound No. 87.

2-Methoxy-N-(5-(4-oxo-3,4-dihydrophthalazin-1-yl)-1H-benzimidazol-2-yl)acetamide was prepared using 2-(4-chloro-3-nitrobenzoyl)benzoic acid in step land methyl N,N'-bis[(methoxymethyl)carbonyl]imidothiocarbamate in step 5. $^1$H-NMR (300 MHz, $d_6$-DMSO): 12.78 (s, 1H), 12.20 (s, 1H), 10.56 (s, 1H), 8.28 (d, 1H), 7.98 (m, 2H), 7.70 (m, 1H), 7.58 (m, 2H), 7.26 (m, 1H), 4.36 (s, 2H, 3.42 (s, 3H) MS [ESI] for $C_{18}H_{15}N_5O_3$: 350 [MH$^+$].

Compound No. 88.

2-Cyano-N-(5-(4-oxo-3,4-dihydrophthalazin-1-yl)-1H-benzimidazol-2-yl)acetamide can be prepared using 2-(4-chloro-3-nitrobenzoyl)benzoic acid in step land methyl N,N'-bis[(cyanomethyl)carbonyl] imidothiocarbamate in step 5.

Compound No. 89.

2-(Dimethylamino)-N-(5-(4-oxo-3,4-dihydrophthalazin-1-yl)-1H-benzimidazol-2-yl)acetamide can be prepared using 2-(4-chloro-3-nitrobenzoyl)benzoic acid in step land methyl N,N'-bis[(N,N-dimethylaminomethyl)carbonyl]imidothiocarbamate in step 5.

Compound No. 90.

Ethyl(6-methyl-5-(4-oxo-3,4-dihydrophthalazin-1-yl)-1H-benzimidazol-2-yl)carbamate can be prepared using 4-(4,5-diamino-2-methylphenyl)phthalazin-1(2H)-one and 1,3-bis(ethoxycarbonyl)-2-methyl-2-thiopseudourea in step 5.

Compound No. 91.

Ethyl(7-methyl-5-(4-oxo-3,4-dihydrophthalazin-1-yl)-1H-benzimidazol-2-yl)carbamate can be prepared using 4-(3,4-diamino-5-methylphenyl)phthalazin-1(2H)-one and 1,3-bis(ethoxycarbonyl)-2-methyl-2-thiopseudourea in step 5.

Compound No. 92.

Ethyl(4-methyl-5-(4-oxo-3,4-dihydrophthalazin-1-yl)-1H-benzimidazol-2-yl)carbamate can be prepared using 4-(3,4-diamino-2-methylphenyl)phthalazin-1(2H)-one and 1,3-bis(ethoxycarbonyl)-2-methyl-2-thiopseudourea in step 5.

Compound No. 93.

Ethyl(5-(7-fluoro-4-oxo-3,4-dihydrophthalazin-1-yl)-6-methyl-1H-benzimidazol-2-yl)carbamate can be prepared using 4-(4,5-diamino-2-methylphenyl)-6-fluorophthalazin-1 (2H)-one and 1,3-bis(ethoxycarbonyl)-2-methyl-2-thiopseudourea in step 5.

Compound No. 94.

Ethyl(5-(6,7-difluoro-4-oxo-3,4-dihydrophthalazin-1-yl)-6-methyl-1H-benzimidazol-2-yl)carbamate can be prepared using 4-(4,5-diamino-2-methylphenyl)-6,7-difluorophthalazin-1(2H)-one and 1,3-bis(ethoxycarbonyl)-2-methyl-2-thiopseudourea in step 5.

Compound No. 95.

Ethyl(5-(7-fluoro-4-oxo-3,4-dihydrophthalazin-1-yl)-7-methyl-1H-benzimidazol-2-yl)carbamate can be prepared using 4-(3,4-diamino-5-methylphenyl)-6-fluorophthalazin-1 (2H)-one and 1,3-bis(ethoxycarbonyl)-2-methyl-2-thiopseudourea in step 5.

Compound No. 96.

Ethyl(5-(6,7-difluoro-4-oxo-3,4-dihydrophthalazin-1-yl)-7-methyl-1H-benzimidazol-2-yl)carbamate can be prepared using 4-(3,4-diamino-5-methylphenyl)-6,7-difluorophthalazin-1(2H)-one and 1,3-bis(ethoxycarbonyl)-2-methyl-2-thiopseudourea in step 5.

Compound No. 97.

Ethyl(5-(7-fluoro-4-oxo-3,4-dihydrophthalazin-1-yl)-4-methyl-1H-benzimidazol-2-yl)carbamate can be prepared using 4-(3,4-diamino-2-methylphenyl)-6-fluorophthalazin-1(2H)-one and 1,3-bis(ethoxycarbonyl)-2-methyl-2-thiopseudourea in step 5.

Compound No. 98.

Ethyl(5-(6,7-difluoro-4-oxo-3,4-dihydrophthalazin-1-yl)-4-methyl-1H-benzimidazol-2-yl)carbamate can be prepared using 4-(3,4-diamino-2-methylphenyl)-6,7-difluorophthalazin-1(2H)-one and 1,3-bis(ethoxycarbonyl)-2-methyl-2-thiopseudourea in step 5.

Compound No. 99.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(isobutyloxycarbonyl)-2-methyl-2-thiopseudourea in step 5.

Compound No. 100.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(isobutyloxycarbonyl)-2-methyl-2-thiopseudourea in step 5.

Compound No. 101.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(isobutyloxycarbonyl)-2-methyl-2-thiopseudourea in step 5.

Compound No. 102.

Methyl(5-(6,7-difluoro-4-oxo-3,4-dihydrophthalazin-1-yl)-1H-benzimidazol-2-yl)carbamate was prepared using 2-(4-chloro-3-nitrobenzoyl)-4,5-difluorobenzoic acid in step 1 and 1,3-bis(isobutyloxycarbonyl)-2-methyl-2-thiopseudourea in step 5. $^1$H-NMR (300 MHz, d$_6$-DMSO): 12.94 (s, 1H), 11.90 (s, 2H), 8.18 (d, 1H), 8.06 (m, 2H), 7.94 (d, 1H), 7.66 (d, 1H), 3.98 (, 2H), 1.98 (m, 1H), 0.98 (d, 6H). MS [ESI] for $C_{20}H_{17}F_2N_5O_3$: 414 [MH$^+$].

Compound No. 103.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(2-chloroethoxycarbonyl)-2-methyl-2-thiopseudourea in step 5.

Compound No. 104.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(2-chloroethoxycarbonyl)-2-methyl-2-thiopseudourea in step 5.

Compound No. 105.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(2-chloroethoxycarbonyl)-2-methyl-2-thiopseudourea in step 5.

Compound No. 106.

Methyl(5-(6,7-difluoro-4-oxo-3,4-dihydrophthalazin-1-yl)-1H-benzimidazol-2-yl)carbamate was prepared using 2-(4-chloro-3-nitrobenzoyl)-4,5-difluorobenzoic acid in step 1 and 1,3-bis(2-chloroethoxycarbonyl)-2-methyl-2-thiopseudourea in step 5. MS [ESI] for $C_{18}H_{12}ClF_2N_5O_3$: 420 [MH$^+$].

Compound No. 107.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(2-chloroethoxycarbonyl)-2-methyl-2-thiopseudourea in step 5, followed by subsequent reaction of the crude product with dimethylamine.

Compound No. 108.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(2-chloroethoxycarbonyl)-2-methyl-2-thiopseudourea in step 5, followed by subsequent reaction of the crude product with dimethylamine.

Compound No. 109.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(2-chloroethoxycarbonyl)-2-methyl-2-thiopseudourea in step 5, followed by subsequent reaction of the crude product with dimethylamine.

Compound No. 110.

Methyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(2-chloroethoxycarbonyl)-2-methyl-2-thiopseudourea in step 5, followed by subsequent reaction of the crude product with dimethylamine.

Compound No. 111.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(3-chloropropyloxycarbonyl)-2-methyl-2-thiopseudourea in step 5.

Compound No. 112.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(3-chloropropyloxycarbonyl)-2-methyl-2-thiopseudourea in step 5.

Compound No. 113.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(3-chloropropyloxycarbonyl)-2-methyl-2-thiopseudourea in step 5.

Compound No. 114.

Methyl(5-(6,7-difluoro-4-oxo-3,4-dihydrophthalazin-1-yl)-1H-benzimidazol-2-yl)carbamate was prepared using 2-(4-chloro-3-nitrobenzoyl)-4,5-difluorobenzoic acid in step 1 and 1,3-bis(3-chloropropyloxycarbonyl)-2-methyl-2-thiopseudourea in step 5. MS [ESI] for $C_{19}H_{14}ClF_2N_5O_3$: 434 [MH$^+$].

Compound No. 115.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(3-chloropropyloxycarbonyl)-2-methyl-2-thiopseudourea in step 5, followed by subsequent reaction of the crude product with dimethylamine.

Compound No. 116.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(3-chloropropyloxycarbonyl)-2-methyl-2-thiopseudourea in step 5, followed by subsequent reaction of the crude product with dimethylamine.

Compound No. 117.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(3-chloropropyloxycarbonyl)-2-methyl-2-thiopseudourea in step 5, followed by subsequent reaction of the crude product with dimethylamine.

Compound No. 118.

Methyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(3-chloropropyloxycarbonyl)-2-methyl-2-thiopseudourea in step 5, followed by subsequent reaction of the crude product with dimethylamine.

Compound No. 119.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(cyclohexyl-4-oxycarbonyl)-2-methyl-2-thiopseudourea in step 5.

Compound No. 120.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(cyclohexyl-4-oxycarbonyl oxycarbonyl)-2-methyl-2-thiopseudourea in step 5.

Compound No. 121.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(cyclohexyl-4-oxycarbonyl)-2-methyl-2-thiopseudourea in step 5.

Compound No. 122.

Methyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(cyclohexyl-4-oxycarbonyl)-2-methyl-2-thiopseudourea in step 5.

Compound No. 123.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis{1-[(1,1-dimethylethox)carbonyl-piperidine]-4-oxycarbonyl}-2-methyl-2-thiopseudourea in step 5, followed by subsequent de-protection and reductive alkylation.

Compound No. 124.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis{1-[(1,1-dimethylethox)carbonyl-piperidine]-4-oxycarbonyl}-2-methyl-2-thiopseudourea in step 5, followed by subsequent de-protection and reductive alkylation.

Compound No. 125.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis{1-[(1,1-dimethylethox)carbonyl-piperidine]-4-oxycarbonyl}-2-methyl-2-thiopseudourea in step 5, followed by subsequent de-protection and reductive alkylation.

Compound No. 126.

Methyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis{1-[(1,1-dimethylethox)carbonyl-piperidine]-4-oxycarbonyl}-2-methyl-2-thiopseudourea in step 5, followed by subsequent de-protection and reductive alkylation.

Compound No. 127.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(benzyloxycarbonyl)-2-methyl-2-thiopseudourea in step 5.

Compound No. 128.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(benzyloxycarbonyl)-2-methyl-2-thiopseudourea in step 5.

Compound No. 129.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(benzyl-oxycarbonyl)-2-methyl-2-thiopseudourea in step 5.

Compound No. 130.

Methyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(benzyloxycarbonyl)-2-methyl-2-thiopseudourea in step 5.

Compound No. 131.

Methyl(5-(8-fluoro-4-oxo-3,4-dihydrophthalazin-1-yl)-1H-benzimidazol-2-yl)carbamate can be prepared using 2-(4-chloro-3-nitrobenzoyl)-3-fluorobenzoic acid in step 1 and 1,3-bis(phenoxycarbonyl)-2-methyl-2-thiopseudourea in step 5.

Compound No. 132.

Methyl(5-(7-fluoro-4-oxo-3,4-dihydrophthalazin-1-yl)-1H-benzimidazol-2-yl)carbamate can be prepared using 2-(4-chloro-3-nitrobenzoyl)-4-fluorobenzoic acid in step 1 and 1,3-bis(phenoxycarbonyl)-2-methyl-2-thiopseudourea in step 5.

Compound No. 133.

Methyl(5-(5,8-difluoro-4-oxo-3,4-dihydrophthalazin-1-yl)-1H-benzimidazol-2-yl)carbamate can be prepared using 2-(4-chloro-3-nitrobenzoyl)-3,6-difluorobenzoic acid in step 1 and 1,3-bis(phenoxycarbonyl)-2-methyl-2-thiopseudourea in step 5.

Compound No. 134.

Methyl(5-(6,7-difluoro-4-oxo-3,4-dihydrophthalazin-1-yl)-1H-benzimidazol-2-yl)carbamate can be prepared using 2-(4-chloro-3-nitrobenzoyl)-4,5-difluorobenzoic acid in step 1 and 1,3-bis(phenoxycarbonyl)-2-methyl-2-thiopseudourea in step 5.

Compound No. 135.

Ethyl(7-chloro-5-(4-oxo-3,4-dihydrophthalazin-1-yl)-1H-benzimidazol-2-yl)carbamate was prepared using 4-(3,4-diamino-5-chlorophenyl)phthalazin-1(2H)-one and 1,3 bis(ethoxycarbonyl)-2-methyl-2-thiopseudourea in step 5.
$^1$H-NMR (300 MHz, $d_6$-DMSO): 12.94 (s, 1H), 12.38 (s, 1H), 11.98 (s, 1H), 8.16 (d, 1H), 7.98-7.90 (m, 3H), 7.76 (m, 1H), 7.68 (m, 1H), 4.18 (q, 2H), 1.26 (t, 3H). MS [ESI] for $C_{18}H_{14}ClN_5O_3$: 384 [MH$^+$].

Compound No. 136.

Methyl(7-chloro-5-(4-oxo-3,4-dihydrophthalazin-1-yl)-1H-benzimidazol-2-yl)carbamate can be prepared using 4-(3,4-diamino-5-chlorophenyl)phthalazin-1(2H)-one and 1,3 bis(methoxycarbonyl)-2-methyl-2-thiopseudourea in step 5.

Compound No. 137.

2-Methoxyethyl(7-chloro-5-(4-oxo-3,4-dihydrophthalazin-1-yl)-1H-benzimidazol-2-yl)carbamate was prepared using 4-(3,4-diamino-5-chlorophenyl)phthalazin-1(2H)-one and 1,3 bis(methoxyethoxycarbonyl)-2-methyl-2-thiopseudourea in step 5. MS [ESI] $C_{19}H_{16}ClN_5O_4$: 414 [MH$^+$].

Compound No. 138.

1-Ethyl-3-(7-chloro-5-(4-oxo-3,4-dihydrophthalazin-1-yl)-1H-benzimidazol-2-yl)urea was prepared using 4-(3,4-diamino-5-chlorophenyl)phthalazin-1(2H)-one and N,N'-bis[(ethylamino)-carbonyl]carbamimidothioic acid methyl ester in step 5. MS [ESI] $C_{18}H_{15}ClN_6O_2$: 383 [MH$^+$].

Compound No. 139.

N-(7-chloro-5-(4-oxo-3,4-dihydrophthalazin-1-yl)-1H-benzimidazol-2-yl)butyramide was prepared using 4-(3,4-diamino-5-chlorophenyl)phthalazin-1(2H)-one and N,N'-bis[(propyl)carbonyl-imidothiocarbamate in step 5. 1H-NMR (300 MHz, d$_6$-DMSO): 12.86 (s, 1H), 12.28 (s, 1H), 10.98 (s, 1H), 8.16 (d, 1H), 8.00-7.91 (m, 3H), 7.78 (m, 1H), 7.68 (m, 1H), 2.40 (dd, 2H), 1.66 (m, 2H), 0.98 (t, 3H). MS [ESI] for $C_{19}H_{16}ClN_5O_2$: 382 [MH$^+$].

Compound No. 140.

Ethyl(7-bromo-5-(4-oxo-3,4-dihydrophthalazin-1-yl)-1H-benzimidazol-2-yl)carbamate was prepared using 4-(3,4-diamino-5-bromophenyl)phthalazin-1(2H)-one and 1,3 bis(ethoxycarbonyl)-2-methyl-2-thiopseudourea in step 5. 1H-NMR (300 MHz, d$_6$-DMSO): 12.96 (s, 1H), 12.38 (s, 1H), 11.96 (s, 1H), 8.18 (d, 1H), 8.09 (s, 1H), 8.01 (m, 2H), 7.76 (m, 1H), 7.68 (m, 1H), 4.18 (q, 2H), 1.26 (t, 3H). MS [ESI] for $C_{18}H_{14}BrN_5O_3$: 428 [MH$^+$].

Compound No. 141.

Methyl(7-bromo-5-(4-oxo-3,4-dihydrophthalazin-1-yl)-1H-benzimidazol-2-yl)carbamate can be prepared using 4-(3,4-diamino-5-bromophenyl)phthalazin-1(2H)-one and 1,3 bis(methoxycarbonyl)-2-methyl-2-thiopseudourea in step 5.

Compound No. 142.

2-Methoxyethyl(7-bromo-5-(4-oxo-3,4-dihydrophthalazin-1-yl)-1H-benzimidazol-2-yl)carbamate can be prepared using 4-(3,4-diamino-5-bromophenyl)phthalazin-1(2H)-one and 1,3 bis(methoxyethoxycarbonyl)-2-methyl-2-thiopseudourea in step 5.

Compound No. 143.

1-Ethyl-3-(7-bromo-5-(4-oxo-3,4-dihydrophthalazin-1-yl)-1H-benzimidazol-2-yl)urea can be prepared using 4-(3,4-diamino-5-bromophenyl)phthalazin-1(2H)-one and N,N'-bis[(ethylamino)-carbonyl]carbamimidothioic acid methyl ester in step 5.

Compound No. 144.

N-(7-bromo-5-(4-oxo-3,4-dihydrophthalazin-1-yl)-1H-benzimidazol-2-yl)butyramide can be prepared using 4-(3,4-diamino-5-bromophenyl)phthalazin-1(2H)-one and N,N'-bis[(propyl)carbonyl-imidothiocarbamate in step 5.

Compound No. 145.

Ethyl(7-methyl-5-(4-oxo-3,4-dihydrophthalazin-1-yl)-1H-benzimidazol-2-yl)carbamate can be prepared using 4-(3,4-diamino-5-methylphenyl)phthalazin-1(2H)-one and 1,3 bis(ethoxycarbonyl)-2-methyl-2-thiopseudourea in step 5.

Compound No. 146.

Methyl(7-methyl-5-(4-oxo-3,4-dihydrophthalazin-1-yl)-1H-benzimidazol-2-yl)carbamate can be prepared using 4-(3,4-diamino-5-methylphenyl)phthalazin-1(2H)-one and 1,3 bis(methoxycarbonyl)-2-methyl-2-thiopseudourea in step 5.

Compound No. 147.

2-Methoxyethyl(7-methyl-5-(4-oxo-3,4-dihydrophthalazin-1-yl)-1H-benzimidazol-2-yl)carbamate can be prepared using 4-(3,4-diamino-5-methylphenyl)phthalazin-1(2H)-one and 1,3 bis(methoxyethoxycarbonyl)-2-methyl-2-thiopseudourea in step 5.

Compound No. 148.

1-Ethyl-3-(7-methyl-5-(4-oxo-3,4-dihydrophthalazin-1-yl)-1H-benzimidazol-2-yl)urea can be prepared using 4-(3,4-diamino-5-methylphenyl)phthalazin-1(2H)-one and N,N'-bis[(ethylamino)-carbonyl] carbamimidothioic acid methyl ester in step 5.

Compound No. 149.

N-(7-methyl-5-(4-oxo-3,4-dihydrophthalazin-1-yl)-1H-benzimidazol-2-yl)butyramide can be prepared using 4-(3,4-diamino-5-methylphenyl)phthalazin-1(2H)-one and N,N'-bis[(propyl)carbonyl-imidothiocarbamate in step 5.

| Compound No. | Structure | Name |
|---|---|---|
| 1. | 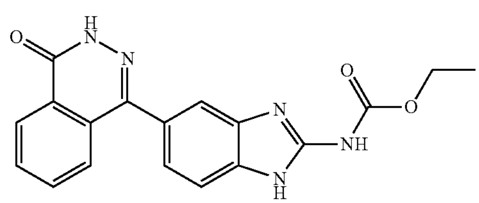 [SMILES: CCOC(=O)Nc1nc2cc(-c3n[nH]c(=O)c4ccccc34)ccc2[nH]1] | Ethyl (5-(4-oxo-3,4-dihydrophthalazin-1-yl)-1H-benzimidazol-2-yl)carbamate |
| 2. | 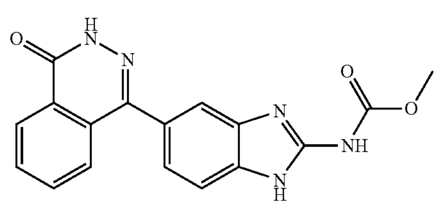 [SMILES: COC(=O)Nc1nc2cc(-c3n[nH]c(=O)c4ccccc34)ccc2[nH]1] | Methyl (5-(4-oxo-3,4-dihydrophthalazin-1-yl)-1H-benzimidazol-2-yl)carbamate |

| Compound No. | Structure | Name |
|---|---|---|
| 3. | 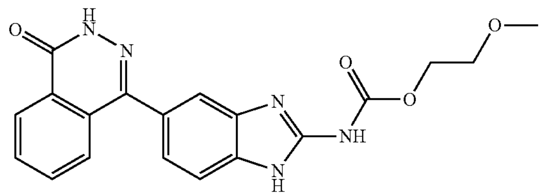 [SMILES: COCCOC(=O)Nc1nc2cc(-c3n[nH]c(=O)c4ccccc34)ccc2[nH]1] | 2-Methoxyethyl (5-(4-oxo-3,4-dihydrophthalazin-1-yl)-1H-benzimidazol-2-yl)carbamate |
| 4. | 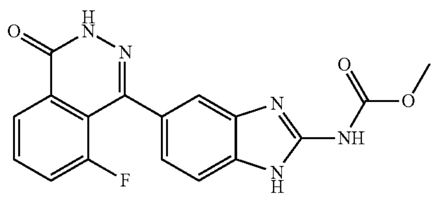 [SMILES: COC(=O)Nc1nc2cc(-c3n[nH]c(=O)c4cccc(F)c34)ccc2[nH]1] | Methyl (5-(8-fluoro-4-oxo-3,4-dihydrophthalazin-1-yl)-1H-benzimidazol-2-yl)carbamate |
| 5. | 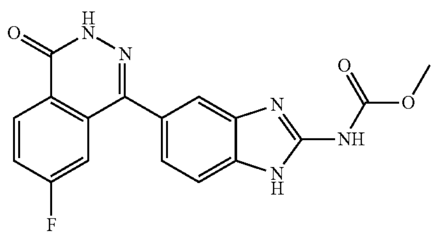 [SMILES: COC(=O)Nc1nc2cc(-c3n[nH]c(=O)c4ccc(F)cc34)ccc2[nH]1] | Methyl (5-(7-fluoro-4-oxo-3,4-dihydrophthalazin-1-yl)-1H-benzimidazol-2-yl)carbamate |
| 6. | 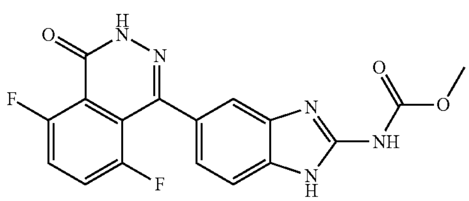 [SMILES: COC(=O)Nc1nc2cc(-c3n[nH]c(=O)c4c(F)ccc(F)c34)ccc2[nH]1] | Methyl (5-(5,8-difluoro-4-oxo-3,4-dihydrophthalazin-1-yl)-1H-benzimidazol-2-yl)carbamate |
| 7. | 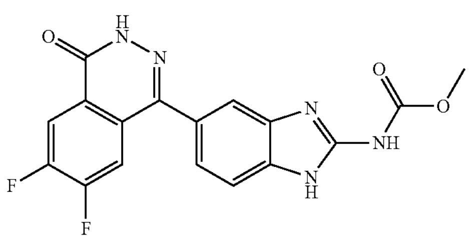 [SMILES: COC(=O)Nc1nc2cc(-c3n[nH]c(=O)c4cc(F)c(F)cc34)ccc2[nH]1] | Methyl (5-(6,7-difluoro-4-oxo-3,4-dihydrophthalazin-1-yl)-1H-benzimidazol-2-yl)carbamate |
| 8. | 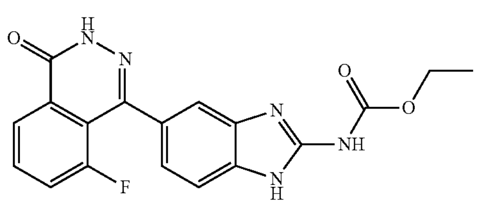 [SMILES: CCOC(=O)Nc1nc2cc(-c3n[nH]c(=O)c4cccc(F)c34)ccc2[nH]1] | Ethyl (5-(8-fluoro-4-oxo-3,4-dihydrophthalazin-1-yl)-1H-benzimidazol-2-yl)carbamate |
| 9. | 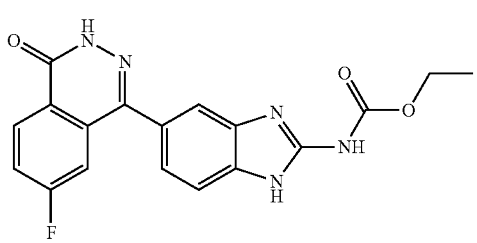 [SMILES: CCOC(=O)Nc1nc2cc(-c3n[nH]c(=O)c4ccc(F)cc34)ccc2[nH]1] | Ethyl (5-(7-fluoro-4-oxo-3,4-dihydrophthalazin-1-yl)-1H-benzimidazol-2-yl)carbamate |

-continued

| Compound No. | Structure | Name |
|---|---|---|
| 10. | 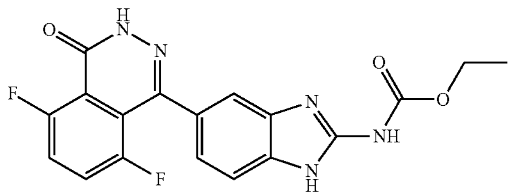 [SMILES: CCOC(=O)Nc1nc2cc(-c3n[nH]c(=O)c4c(F)ccc(F)c34)ccc2[nH]1] | Ethyl (5-(5,8-difluoro-4-oxo-3,4-dihydrophthalazin-1-yl)-1H-benzimidazol-2-yl)carbamate |
| 11. | 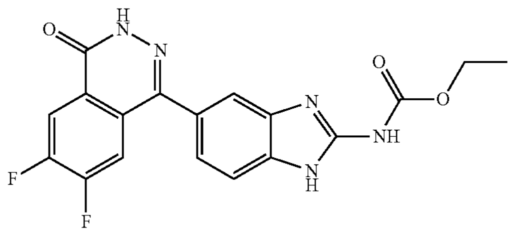 [SMILES: CCOC(=O)Nc1nc2cc(-c3n[nH]c(=O)c4cc(F)c(F)cc34)ccc2[nH]1] | Ethyl (5-(6,7-difluoro-4-oxo-3,4-dihydrophthalazin-1-yl)-1H-benzimidazol-2-yl)carbamate |
| 12. | 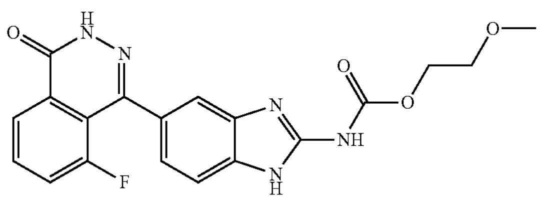 [SMILES: COCCOC(=O)Nc1nc2cc(-c3n[nH]c(=O)c4cccc(F)c34)ccc2[nH]1] | 2-Methoxyethyl (5-(8-fluoro-4-oxo-3,4-dihydrophthalazin-1-yl)-1H-benzimidazol-2-yl)carbmaate |
| 13. | 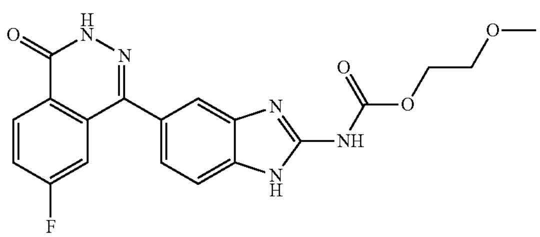 [SMILES: COCCOC(=O)Nc1nc2cc(-c3n[nH]c(=O)c4ccc(F)cc34)ccc2[nH]1] | 2-Methoxyethyl (5-(7-fluoro-4-oxo-3,4-dihydrophthalazin-1-yl)-1H-benzimidazol-2-yl)carbmaate |
| 14. | 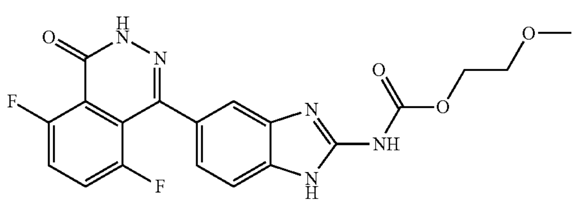 [SMILES: COCCOC(=O)Nc1nc2cc(-c3n[nH]c(=O)c4c(F)ccc(F)c34)ccc2[nH]1] | 2-Methoxyethyl (5-(5,8-difluoro-4-oxo-3,4-dihydrophthalazin-1-yl)-1H-benzimidazol-2-yl)carbamate |
| 15. | 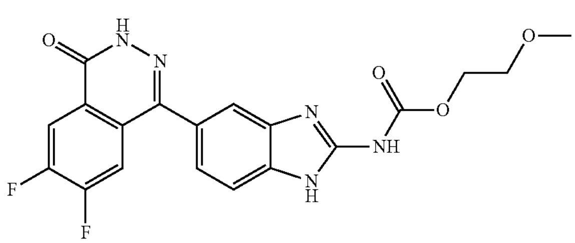 [SMILES: COCCOC(=O)Nc1nc2cc(-c3n[nH]c(=O)c4cc(F)c(F)cc34)ccc2[nH]1] | 2-Methoxyethyl (5-(6,7-difluoro-4-oxo-3,4-dihydrophthalazin-1-yl)-1H-benzimidazol-2-yl)carbamate |
| 16. | 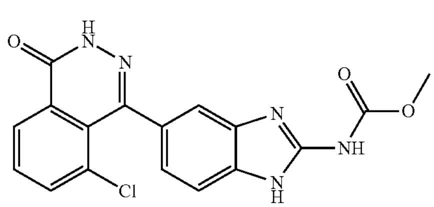 [SMILES: COC(=O)Nc1nc2cc(-c3n[nH]c(=O)c4cccc(Cl)c34)ccc2[nH]1] | Methyl (5-(8-chloro-4-oxo-3,4-dihydrophthalazin-1-yl)-1H-benzimidazol-2-yl)carbamate |

-continued

| Compound No. | Structure | Name |
|---|---|---|
| 17. | 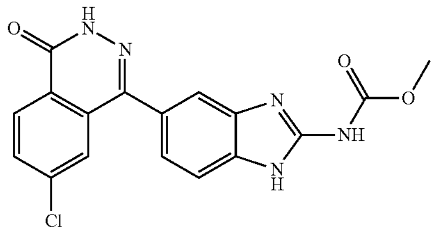 [SMILES: COC(=O)Nc1nc2cc(-c3n[nH]c(=O)c4ccc(Cl)cc34)ccc2[nH]1] | Methyl (5-(7-chloro-4-oxo-3,4-dihydrophthalazin-1-yl)-1H-benzimidazol-2-yl)carbamate |
| 18. | 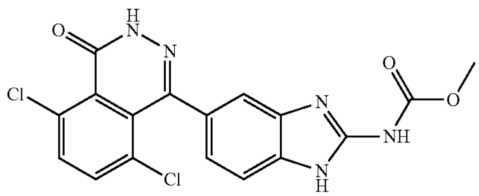 [SMILES: COC(=O)Nc1nc2cc(-c3n[nH]c(=O)c4c(Cl)ccc(Cl)c34)ccc2[nH]1] | Methyl (5-(5,8-dichloro-4-oxo-3,4-dihydrophthalazin-1-yl)-1H-benzimidazol-2-yl)carbamate |
| 19. | 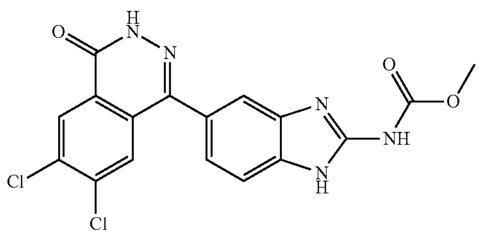 [SMILES: COC(=O)Nc1nc2cc(-c3n[nH]c(=O)c4cc(Cl)c(Cl)cc34)ccc2[nH]1] | Methyl (5-(6,7-dichloro-4-oxo-3,4-dihydrophthalazin-1-yl)-1H-benzimidazol-2-yl)carbamate |
| 20. | 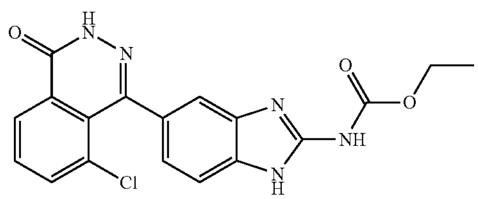 [SMILES: CCOC(=O)Nc1nc2cc(-c3n[nH]c(=O)c4cccc(Cl)c34)ccc2[nH]1] | Ethyl (5-(8-chloro-4-oxo-3,4-dihydrophthalazin-1-yl)-1H-benzimidazol-2-yl)carbamate |
| 21. | 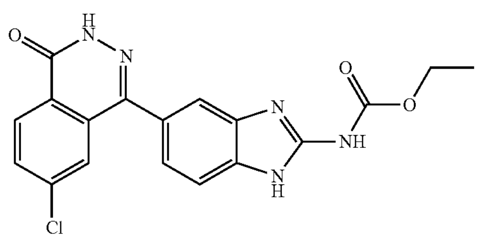 [SMILES: CCOC(=O)Nc1nc2cc(-c3n[nH]c(=O)c4ccc(Cl)cc34)ccc2[nH]1] | Ethyl (5-(7-chloro-4-oxo-3,4-dihydrophthalazin-1-yl)-1H-benzimidazol-2-yl)carbamate |
| 22. | 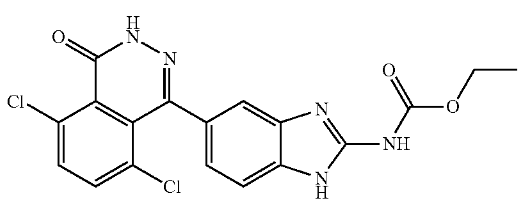 [SMILES: CCOC(=O)Nc1nc2cc(-c3n[nH]c(=O)c4c(Cl)ccc(Cl)c34)ccc2[nH]1] | Ethyl (5-(5,8-dichloro-4-oxo-3,4-dihydrophthalazin-1-yl)-1H-benzimidazol-2-yl)carbamate |
| 23. | 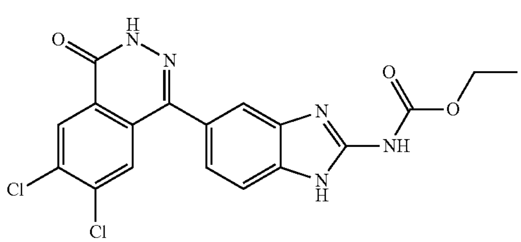 [SMILES: CCOC(=O)Nc1nc2cc(-c3n[nH]c(=O)c4cc(Cl)c(Cl)cc34)ccc2[nH]1] | Ethyl (5-(6,7-dichloro-4-oxo-3,4-dihydrophthalazin-1-yl)-1H-benzimidazol-2-yl)carbamate |

| Compound No. | Structure | Name |
|---|---|---|
| 24. | 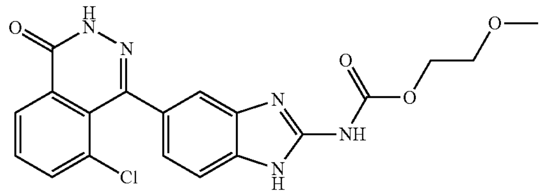 [SMILES: COCCOC(=O)Nc1nc2cc(-c3n[nH]c(=O)c4cccc(Cl)c34)ccc2[nH]1] | 2-Methoxyethyl (5-(8-chloro-4-oxo-3,4-dihydrophthalazin-1-yl)-1H-benzimidazol-2-yl)carbamate |
| 25. | 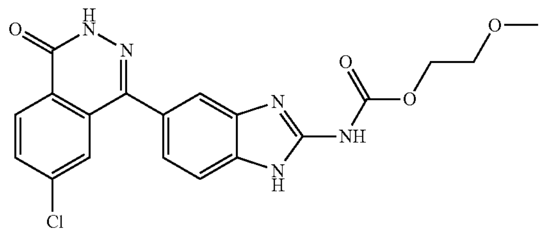 [SMILES: COCCOC(=O)Nc1nc2cc(-c3n[nH]c(=O)c4ccc(Cl)cc34)ccc2[nH]1] | 2-Methoxyethyl (5-(7-chloro-4-oxo-3,4-dihydrophthalazin-1-yl)-1H-benzimidazol-2-yl)carbamate |
| 26. | 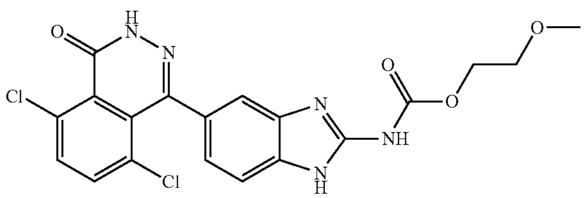 [SMILES: COCCOC(=O)Nc1nc2cc(-c3n[nH]c(=O)c4c(Cl)ccc(Cl)c34)ccc2[nH]1] | 2-Methoxyethyl (5-(5,8-dichloro-4-oxo-3,4-dihydrophthalazin-1-yl)-1H-benzimidazol-2-yl)carbamate |
| 27. | 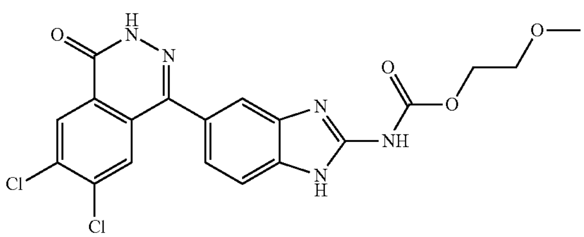 [SMILES: COCCOC(=O)Nc1nc2cc(-c3n[nH]c(=O)c4cc(Cl)c(Cl)cc34)ccc2[nH]1] | 2-Methoxyethyl (5-(6,7-dichloro-4-oxo-3,4-dihydrophthalazin-1-yl)-1H-benzimidazol-2-yl)carbamate |
| 28. | 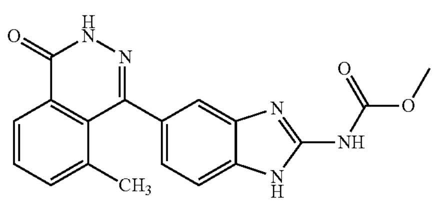 [SMILES: COC(=O)Nc1nc2cc(-c3n[nH]c(=O)c4cccc(C)c34)ccc2[nH]1] | Methyl (5-(8-methyl-4-oxo-3,4-dihydrophthalazin-1-yl)-1H-benzimidazol-2-yl)carbamate |
| 29. | 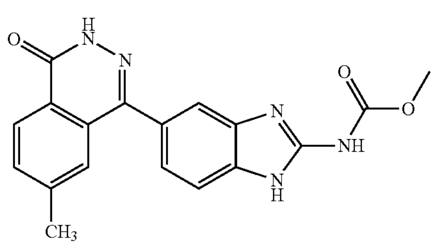 [SMILES: COC(=O)Nc1nc2cc(-c3n[nH]c(=O)c4ccc(C)cc34)ccc2[nH]1] | Methyl (5-(7-methyl-4-oxo-3,4-dihydrophthalazin-1-yl)-1H-benzimidazol-2-yl)carbamate |
| 30. | 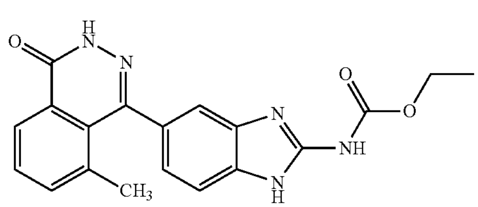 [SMILES: CCOC(=O)Nc1nc2cc(-c3n[nH]c(=O)c4cccc(C)c34)ccc2[nH]1] | Ethyl (5-(8-methyl-4-oxo-3,4-dihydrophthalazin-1-yl)-1H-benzimidazol-2-yl)carbamate |

-continued

| Compound No. | Structure | Name |
|---|---|---|
| 31. | 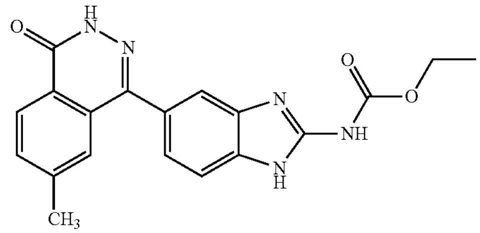 [SMILES: CCOC(=O)Nc1nc2cc(-c3n[nH]c(=O)c4ccc(C)cc34)ccc2[nH]1] | Ethyl (5-(7-methyl-4-oxo-3,4-dihydrophthalazin-1-yl)-1H-benzimidazol-2-yl)carbamate |
| 32. | 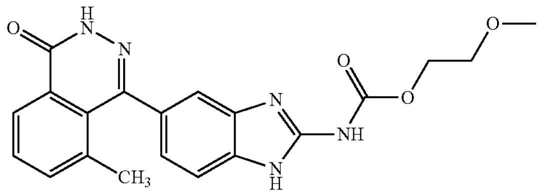 [SMILES: COCCOC(=O)Nc1nc2cc(-c3n[nH]c(=O)c4cccc(C)c34)ccc2[nH]1] | 2-Methoxyethyl (5-(8-methyl-4-oxo-3,4-dihydrophthalazin-1-yl)-1H-benzimidazol-2-yl)carbamate |
| 33. | 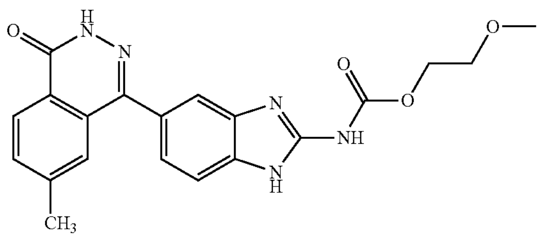 [SMILES: COCCOC(=O)Nc1nc2cc(-c3n[nH]c(=O)c4ccc(C)cc34)ccc2[nH]1] | 2-Methoxyethyl (5-(7-methyl-4-oxo-3,4-dihydrophthalazin-1-yl)-1H-benzimidazol-2-yl)carbamate |
| 34. | 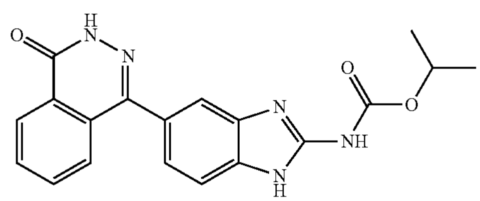 [SMILES: CC(C)OC(=O)Nc1nc2cc(-c3n[nH]c(=O)c4ccccc34)ccc2[nH]1] | Isopropyl (5-(4-oxo-3,4-dihydrophthalazin-1-yl)-1H-benzimidazol-2-yl)carbamate |
| 35. | 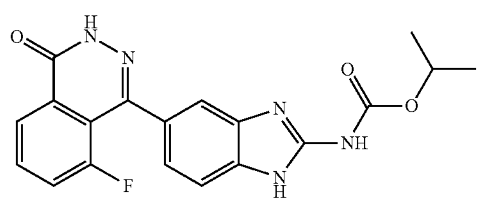 [SMILES: CC(C)OC(=O)Nc1nc2cc(-c3n[nH]c(=O)c4cccc(F)c34)ccc2[nH]1] | Isopropyl (5-(8-fluoro-4-oxo-3,4-dihydrophthalazin-1-yl)-1H-benzimidazol-2-yl)carbamate |
| 36. | 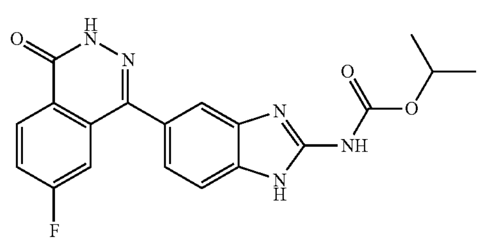 [SMILES: CC(C)OC(=O)Nc1nc2cc(-c3n[nH]c(=O)c4ccc(F)cc34)ccc2[nH]1] | Isopropyl (5-(7-fluoro-4-oxo-3,4-dihydrophthalazin-1-yl)-1H-benzimidazol-2-yl)carbamate |
| 37. | 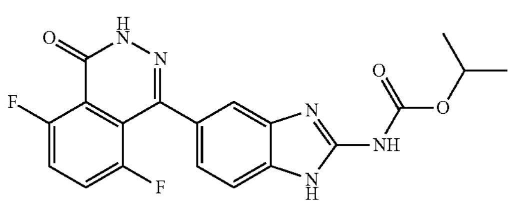 [SMILES: CC(C)OC(=O)Nc1nc2cc(-c3n[nH]c(=O)c4c(F)ccc(F)c34)ccc2[nH]1] | Isopropyl (5-(5,8-difluoro-4-oxo-3,4-dihydrophthalazin-1-yl)-1H-benzimidazol-2-yl)carbamate |

-continued

| Compound No. | Structure | Name |
|---|---|---|
| 38. | 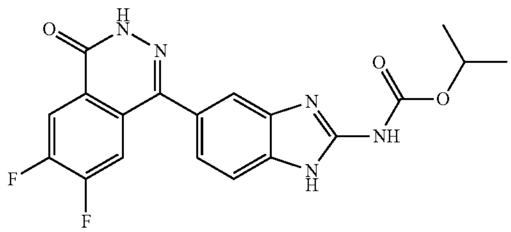 [SMILES: CC(C)OC(=O)Nc1nc2cc(-c3n[nH]c(=O)c4cc(F)c(F)cc34)ccc2[nH]1] | Isopropyl (5-(6,7-difluoro-4-oxo-3,4-dihydrophthalazin-1-yl)-1H-benzimidazol-2-yl)carbamate |
| 39. | 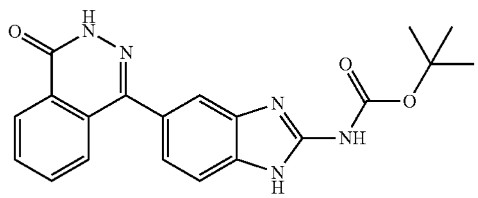 [SMILES: CC(C)(C)OC(=O)Nc1nc2cc(-c3n[nH]c(=O)c4ccccc34)ccc2[nH]1] | tert-Butyl (5-(4-oxo-3,4-dihydrophthalazin-1-yl)-1H-benzimidazol-2-yl)carbamate |
| 40. | 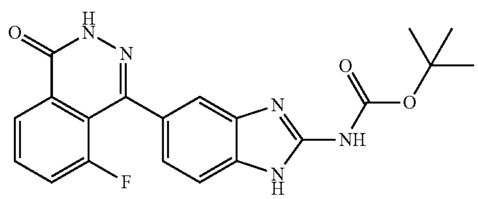 [SMILES: CC(C)(C)OC(=O)Nc1nc2cc(-c3n[nH]c(=O)c4cccc(F)c34)ccc2[nH]1] | tert-Butyl (5-(8-fluoro-4-oxo-3,4-dihydrophthalazin-1-yl)-1H-benzimidazol-2-yl)carbamate |
| 41. | 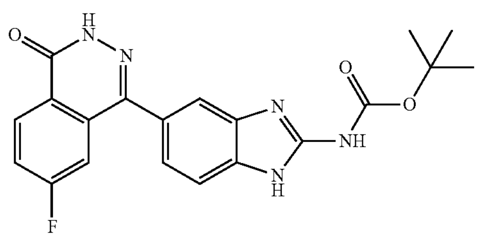 [SMILES: CC(C)(C)OC(=O)Nc1nc2cc(-c3n[nH]c(=O)c4ccc(F)cc34)ccc2[nH]1] | tert-Butyl (5-(7-fluoro-4-oxo-3,4-dihydrophthalazin-1-yl)-1H-benzimidazol-2-yl)carbamate |
| 42. | 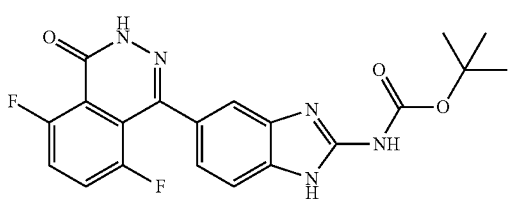 [SMILES: CC(C)(C)OC(=O)Nc1nc2cc(-c3n[nH]c(=O)c4c(F)ccc(F)c34)ccc2[nH]1] | tert-Butyl (5-(5,8-difluoro-4-oxo-3,4-dihydrophthalazin-1-yl)-1H-benzimidazol-2-yl)carbamate |
| 43. | 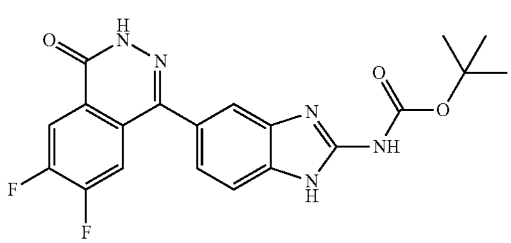 [SMILES: CC(C)(C)OC(=O)Nc1nc2cc(-c3n[nH]c(=O)c4cc(F)c(F)cc34)ccc2[nH]1] | tert-butyl (5-(6,7-difluoro-4-oxo-3,4-dihydrophthalazin-1-yl)-1H-benzimidazol-2-yl)carbamate |
| 44. | 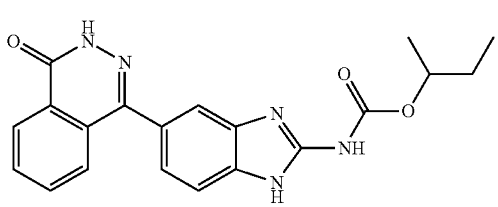 [SMILES: CCC(C)OC(=O)Nc1nc2cc(-c3n[nH]c(=O)c4ccccc34)ccc2[nH]1] | sec-Butyl (5-(4-oxo-3,4-dihydrophthalazin-1-yl)-1H-benzimidazol-2-yl)carbamate |

-continued

| Compound No. | Structure | Name |
|---|---|---|
| 45. | 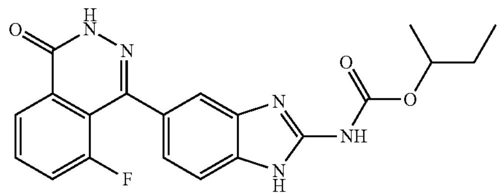 [SMILES: CCC(C)OC(=O)Nc1nc2cc(-c3n[nH]c(=O)c4cccc(F)c34)ccc2[nH]1] | sec-Butyl (5-(8-fluoro-4-oxo-3,4-dihydrophthalazin-1-yl)-1H-benzimidazol-2-yl)carbamate |
| 46. | 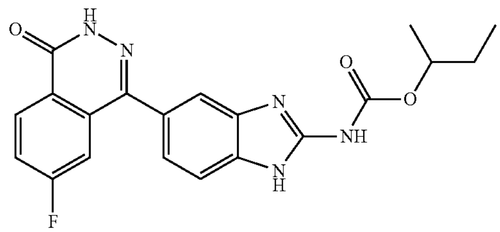 [SMILES: CCC(C)OC(=O)Nc1nc2cc(-c3n[nH]c(=O)c4ccc(F)cc34)ccc2[nH]1] | sec-Butyl (5-(7-fluoro-4-oxo-3,4-dihydrophthalazin-1-yl)-1H-benzimidazol-2-yl)carbamate |
| 47. | 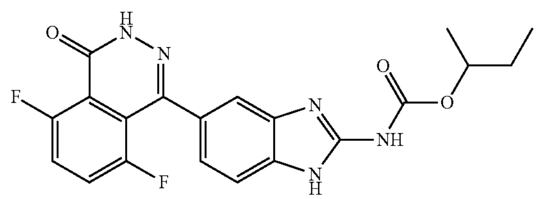 [SMILES: CCC(C)OC(=O)Nc1nc2cc(-c3n[nH]c(=O)c4c(F)ccc(F)c34)ccc2[nH]1] | sec-Butyl (5-(5,8-difluoro-4-oxo-3,4-dihydrophthalazin-1-yl)-1H-benzimidazol-2-yl)carbamate |
| 48. | 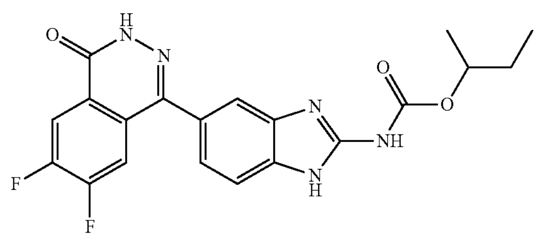 [SMILES: CCC(C)OC(=O)Nc1nc2cc(-c3n[nH]c(=O)c4cc(F)c(F)cc34)ccc2[nH]1] | sec-butyl (5-(6,7-difluoro-4-oxo-3,4-dihydrophthalazin-1-yl)-1H-benzimidazol-2-yl)carbamate |
| 49. | 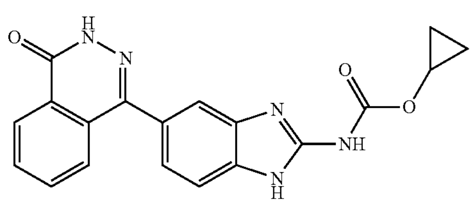 [SMILES: O=C(Nc1nc2cc(-c3n[nH]c(=O)c4ccccc34)ccc2[nH]1)OC1CC1] | Cyclopropyl (5-(4-oxo-3,4-dihydrophthalazin-1-yl)-1H-benzimidazol-2-yl)carbamate |
| 50. | 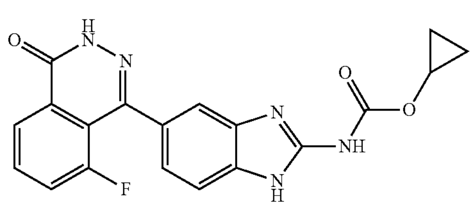 [SMILES: O=C(Nc1nc2cc(-c3n[nH]c(=O)c4cccc(F)c34)ccc2[nH]1)OC1CC1] | Cyclopropyl (5-(8-fluoro-4-oxo-3,4-dihydrophthalazin-1-yl)-1H-benzimidazol-2-yl)carbamate |
| 51. | 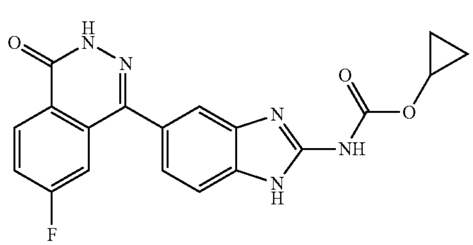 [SMILES: O=C(Nc1nc2cc(-c3n[nH]c(=O)c4ccc(F)cc34)ccc2[nH]1)OC1CC1] | Cyclopropyl (5-(7-fluoro-4-oxo-3,4-dihydrophthalazin-1-yl)-1H-benzimidazol-2-yl)carbamate |

| Compound No. | Structure | Name |
|---|---|---|
| 52. | 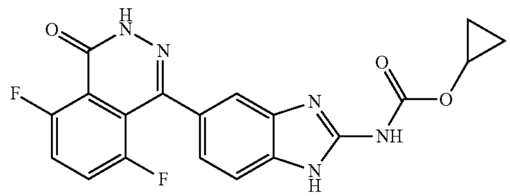 [SMILES: O=C(Nc1nc2cc(-c3n[nH]c(=O)c4c(F)ccc(F)c34)ccc2[nH]1)OC1CC1] | Cyclopropyl (5-(5,8-difluoro-4-oxo-3,4-dihydrophthalazin-1-yl)-1H-benzimidazol-2-yl)carbamate |
| 53. | 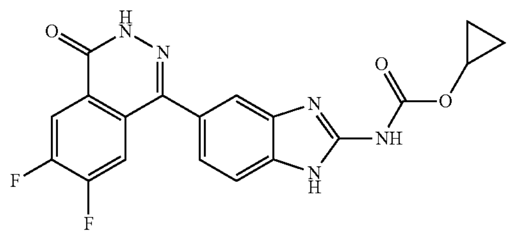 [SMILES: O=C(Nc1nc2cc(-c3n[nH]c(=O)c4cc(F)c(F)cc34)ccc2[nH]1)OC1CC1] | Cyclopropyl (5-(6,7-difluoro-4-oxo-3,4-dihydrophthalazin-1-yl)-1H-benzimidazol-2-yl)carbamate |
| 54. | 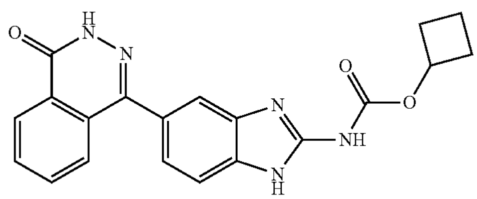 [SMILES: O=C(Nc1nc2cc(-c3n[nH]c(=O)c4ccccc34)ccc2[nH]1)OC1CCC1] | Cyclobutyl (5-(4-oxo-3,4-dihydrophthalazin-1-yl)-1H-benzimidazol-2-yl)carbamate |
| 55. | 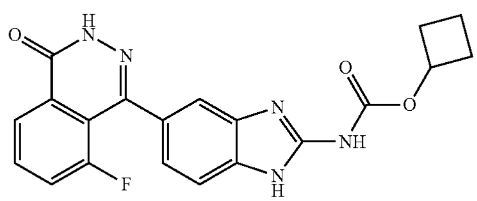 [SMILES: O=C(Nc1nc2cc(-c3n[nH]c(=O)c4cccc(F)c34)ccc2[nH]1)OC1CCC1] | Cyclobutyl (5-(8-fluoro-4-oxo-3,4-dihydrophthalazin-1-yl)-1H-benzimidazol-2-yl)carbamate |
| 56. | 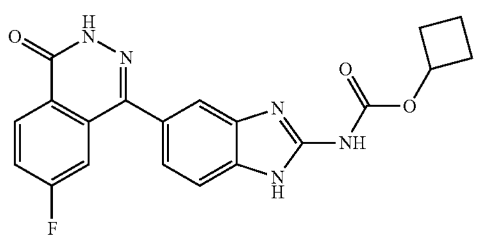 [SMILES: O=C(Nc1nc2cc(-c3n[nH]c(=O)c4ccc(F)cc34)ccc2[nH]1)OC1CCC1] | Cyclobutyl (5-(7-fluoro-4-oxo-3,4-dihydrophthalazin-1-yl)-1H-benzimidazol-2-yl)carbamate |
| 57. | 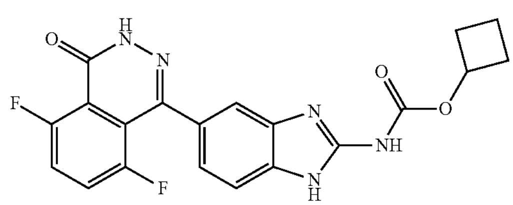 [SMILES: O=C(Nc1nc2cc(-c3n[nH]c(=O)c4c(F)ccc(F)c34)ccc2[nH]1)OC1CCC1] | Cyclobutyl (5-(5,8-difluoro-4-oxo-3,4-dihydrophthalazin-1-yl)-1H-benzimidazol-2-yl)carbamate |
| 58. | 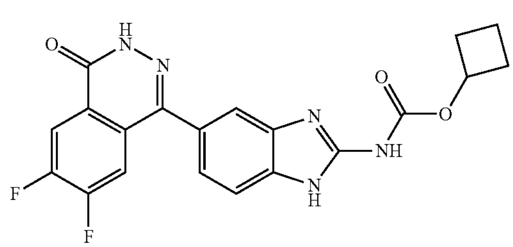 [SMILES: O=C(Nc1nc2cc(-c3n[nH]c(=O)c4cc(F)c(F)cc34)ccc2[nH]1)OC1CCC1] | Cyclobutyl (5-(6,7-difluoro-4-oxo-3,4-dihydrophthalazin-1-yl)-1H-benzimidazol-2-yl)carbamate |

-continued

| Compound No. | Structure | Name |
|---|---|---|
| 59. | 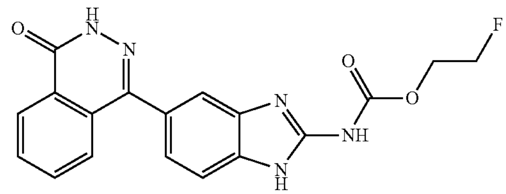 [SMILES: O=C(Nc1nc2cc(-c3n[nH]c(=O)c4ccccc34)ccc2[nH]1)OCCF] | 2-Fluoroethyl (5-(4-oxo-3,4-dihydrophthalazin-1-yl)-1H-benzimidazol-2-yl)carbamate |
| 60. | 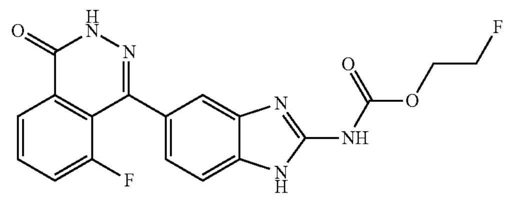 [SMILES: O=C(Nc1nc2cc(-c3n[nH]c(=O)c4cccc(F)c34)ccc2[nH]1)OCCF] | 2-Fluoroethyl (5-(8-fluoro-4-oxo-3,4-dihydrophthalazin-1-yl)-1H-benzimidazol-2-yl)carbamate |
| 61. | 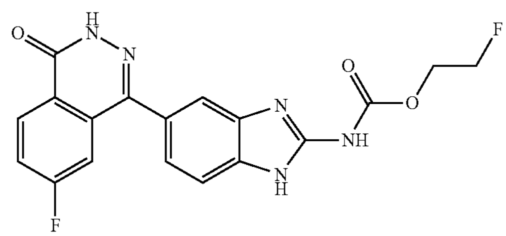 [SMILES: O=C(Nc1nc2cc(-c3n[nH]c(=O)c4ccc(F)cc34)ccc2[nH]1)OCCF] | 2-Fluoroethyl (5-(7-fluoro-4-oxo-3,4-dihydrophthalazin-1-yl)-1H-benzimidazol-2-yl)carbamate |
| 62. | 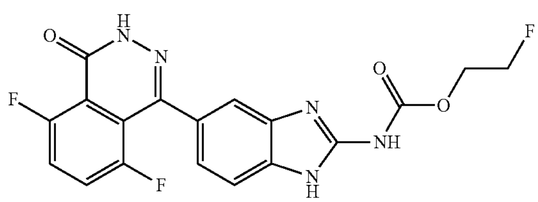 [SMILES: O=C(Nc1nc2cc(-c3n[nH]c(=O)c4c(F)ccc(F)c34)ccc2[nH]1)OCCF] | 2-Fluoroethyl (5-(5,8-difluoro-4-oxo-3,4-dihydrophthalazin-1-yl)-1H-benzimidazol-2-yl)carbamate |
| 63. | 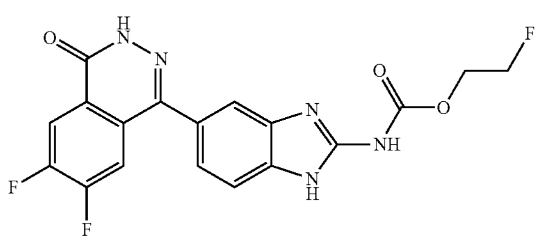 [SMILES: O=C(Nc1nc2cc(-c3n[nH]c(=O)c4cc(F)c(F)cc34)ccc2[nH]1)OCCF] | 2-Fluoroethyl (5-(6,7-difluoro-4-oxo-3,4-dihydrophthalazin-1-yl)-1H-benzimidazol-2-yl)carbamate |
| 64. | 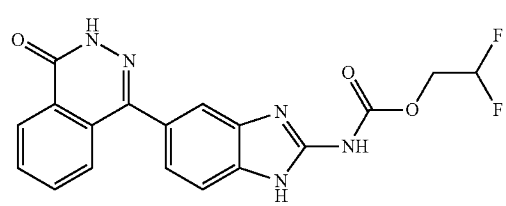 [SMILES: O=C(Nc1nc2cc(-c3n[nH]c(=O)c4ccccc34)ccc2[nH]1)OCC(F)F] | 2,2-Difluoroethyl (5-(4-oxo-3,4-dihydrophthalazin-1-yl)-1H-benzimidazol-2-yl)carbamate |
| 65. | 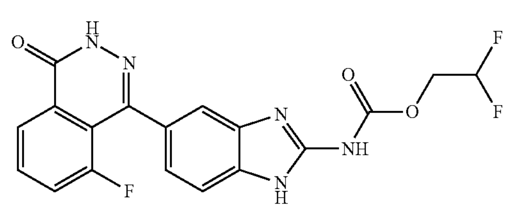 [SMILES: O=C(Nc1nc2cc(-c3n[nH]c(=O)c4cccc(F)c34)ccc2[nH]1)OCC(F)F] | 2,2-Difluoroethyl (5-(8-fluoro-4-oxo-3,4-dihydrophthalazin-1-yl)-1H-benzimidazol-2-yl)carbamate |

-continued

| Compound No. | Name |
|---|---|
| 66. | 2,2-Difluoroethyl (5-(7-fluoro-4-oxo-3,4-dihydrophthalazin-1-yl)-1H-benzimidazol-2-yl)carbamate |
| 67. | 2,2-Difluoroethyl (5-(5,8-difluoro-4-oxo-3,4-dihydrophthalazin-1-yl)-1H-benzimidazol-2-yl)carbamate |
| 68. | 2,2-Difluoroethyl (5-(6,7-difluoro-4-oxo-3,4-dihydrophthalazin-1-yl)-1H-benzimidazol-2-yl)carbamate |
| 69. | 2,2,2-Trifluoroethyl (5-(4-oxo-3,4-dihydrophthalazin-1-yl)-1H-benzimidazol-2-yl)carbamate |
| 70. | 2,2,2-Trifluoroethyl (5-(8-fluoro-4-oxo-3,4-dihydrophthalazin-1-yl)-1H-benzimidazol-2-yl)carbamate |
| 71. | 2,2,2-Trifluoroethyl (5-(7-fluoro-4-oxo-3,4-dihydrophthalazin-1-yl)-1H-benzimidazol-2-yl)carbamate |
| 72. | 2,2,2-Trifluoroethyl (5-(5,8-difluoro-4-oxo-3,4-dihydrophthalazin-1-yl)-1H-benzimidazol-2-yl)carbamate |

-continued

| Compound No. | Structure | Name |
|---|---|---|
| 73. | 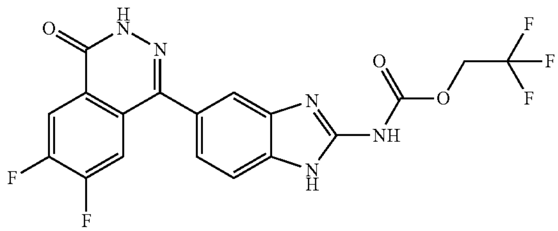 [SMILES: O=C(Nc1nc2cc(-c3n[nH]c(=O)c4cc(F)c(F)cc34)ccc2[nH]1)OCC(F)(F)F] | 2,2,2-Trifluoroethyl (5-(6,7-difluoro-4-oxo-3,4-dihydrophthalazin-1-yl)-1H-benzimidazol-2-yl)carbamate |
| 74. | 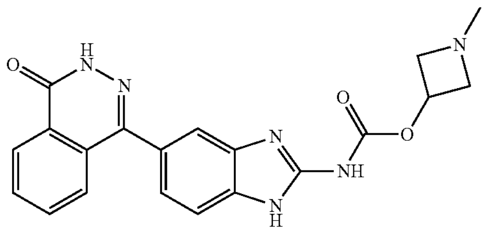 [SMILES: CN1CC(OC(=O)Nc2nc3cc(-c4n[nH]c(=O)c5ccccc45)ccc3[nH]2)C1] | 1-Methylazetidin-3-yl (5-(4-oxo-3,4-dihydrophthalazin-1-yl)-1H-benzimidazol-2-yl)carbamate |
| 75. | 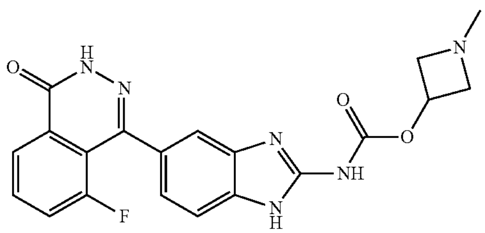 [SMILES: CN1CC(OC(=O)Nc2nc3cc(-c4n[nH]c(=O)c5cccc(F)c45)ccc3[nH]2)C1] | 1-Methylazetidin-3-yl (5-(8-fluoro-4-oxo-3,4-dihydrophthalazin-1-yl)-1H-benzimidazol-2-yl)carbamate |
| 76. | 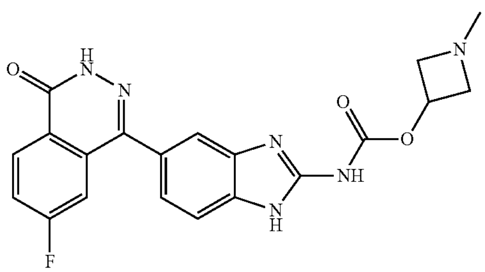 [SMILES: CN1CC(OC(=O)Nc2nc3cc(-c4n[nH]c(=O)c5ccc(F)cc45)ccc3[nH]2)C1] | 1-Methylazetidin-3-yl (5-(7-fluoro-4-oxo-3,4-dihydrophthalazin-1-yl)-1H-benzimidazol-2-yl)carbamate |
| 77. | 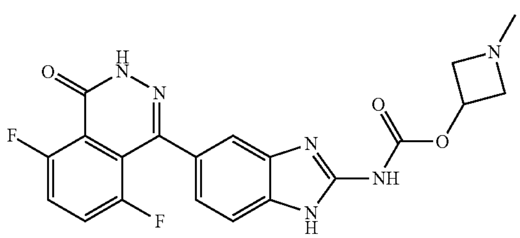 [SMILES: CN1CC(OC(=O)Nc2nc3cc(-c4n[nH]c(=O)c5c(F)ccc(F)c45)ccc3[nH]2)C1] | 1-Methylazetidin-3-yl (5-(5,8-difluoro-4-oxo-3,4-dihydrophthalazin-1-yl)-1H-benzimidazol-2-yl)carbamate |
| 78. | 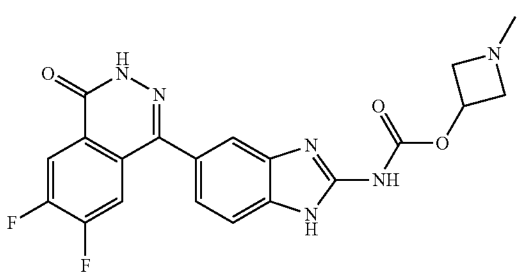 [SMILES: CN1CC(OC(=O)Nc2nc3cc(-c4n[nH]c(=O)c5cc(F)c(F)cc45)ccc3[nH]2)C1] | 1-Methylazetidin-3-yl (5-(6,7-difluoro-4-oxo-3,4-dihydrophthalazin-1-yl)-1H-benzimidazol-2-yl)carbamate |

| Compound No. | Structure | Name |
|---|---|---|
| 79. | 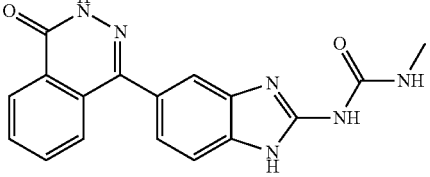 | 1-Methyl-3-(5-(4-oxo-3,4-dihydrophthalazin-1-yl)-1H-benzimidazol-2-yl)urea |
| 80. | 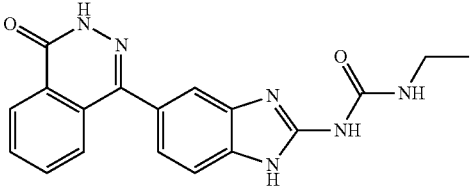 [SMILES: CCNC(=O)Nc1nc2cc(-c3n[nH]c(=O)c4ccccc34)ccc2[nH]1] | 1-Ethyl-3-(5-(4-oxo-3,4-dihydrophthalazin-1-yl)-1H-benzimidazol-2-yl)urea |
| 81. | 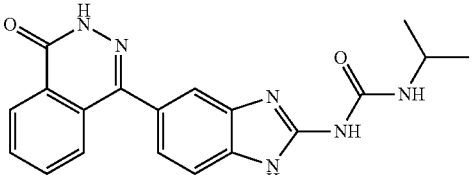 | 1-Isopropyl-3-(5-(4-oxo-3,4-dihydrophthalazin-1-yl)-1H-benzimidazol-2-yl)urea |
| 82. | 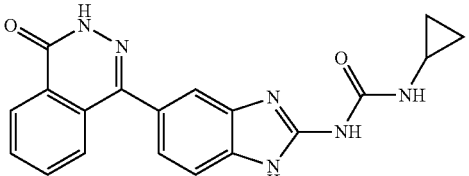 | 1-Cyclopropyl-3-(5-(4-oxo-3,4-dihydrophthalazin-1-yl)-1H-benzimidazol-2-yl)urea |
| 83. | 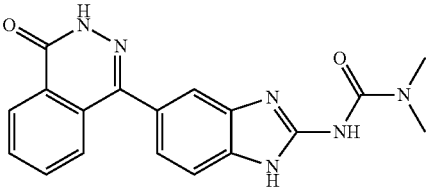 [SMILES: CN(C)C(=O)Nc1nc2cc(-c3n[nH]c(=O)c4ccccc34)ccc2[nH]1] | 1,1-Dimethyl-3-(5-(4-oxo-3,4-dihydrophthalazin-1-yl)-1H-benzimidazol-2-yl)urea |
| 84. | 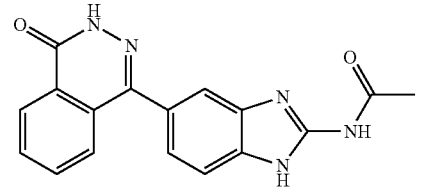 [SMILES: CC(=O)Nc1nc2cc(-c3n[nH]c(=O)c4ccccc34)ccc2[nH]1] | N-(5-(4-oxo-3,4-dihydrophthalazin-1-yl)-1H-benzimidazol-2-yl)acetamide |
| 85. | 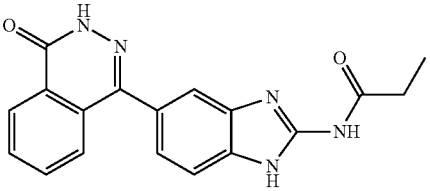 [SMILES: CCC(=O)Nc1nc2cc(-c3n[nH]c(=O)c4ccccc34)ccc2[nH]1] | N-(5-(4-oxo-3,4-dihydrophthalazin-1-yl)-1H-benzimidazol-2-yl)propionamide |

-continued

| Compound No. | Structure | Name |
|---|---|---|
| 86. | 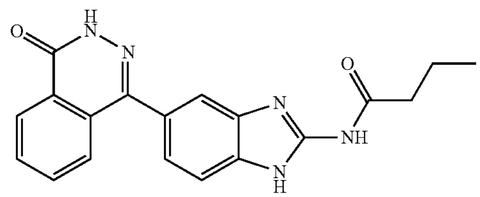 [SMILES: CCCC(=O)Nc1nc2cc(-c3n[nH]c(=O)c4ccccc34)ccc2[nH]1] | N-(5-(4-oxo-3,4-dihydrophthalazin-1-yl)-1H-benzimidazol-2-yl)butyramide |
| 87. | 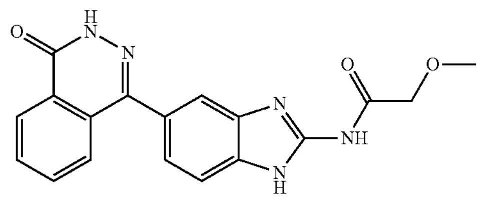 [SMILES: COCC(=O)Nc1nc2cc(-c3n[nH]c(=O)c4ccccc34)ccc2[nH]1] | 2-Methoxy-N-(5-(4-oxo-3,4-dihydrophthalazin-1-yl)-1H-benzimidazol-2-yl)acetamide |
| 88. | 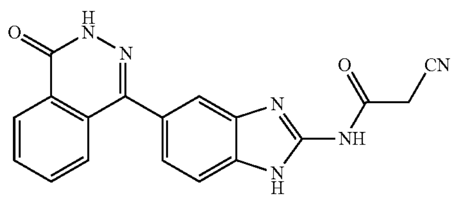 [SMILES: N#CCC(=O)Nc1nc2cc(-c3n[nH]c(=O)c4ccccc34)ccc2[nH]1] | 2-Cyano-(5-(4-oxo-3,4-dihydrophthalazin-1-yl)-1H-benzimidazol-2-yl)acetamide |
| 89. | 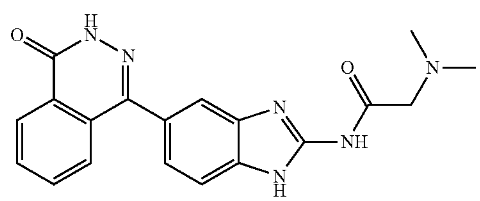 [SMILES: CN(C)CC(=O)Nc1nc2cc(-c3n[nH]c(=O)c4ccccc34)ccc2[nH]1] | 2-(Dimethylamino)-N-(5-(4-oxo-3,4-dihydrophthalazin-1-yl)-1H-benzimidazol-2-yl)acetamide |
| 90. | 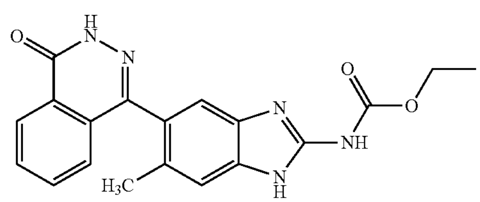 [SMILES: CCOC(=O)Nc1nc2cc(-c3n[nH]c(=O)c4ccccc34)c(C)cc2[nH]1] | Ethyl (6-methyl-5-(4-oxo-3,4-dihydrophthalazin-1-yl)-1H-benzimidazol-2-yl)carbamate |
| 91. | 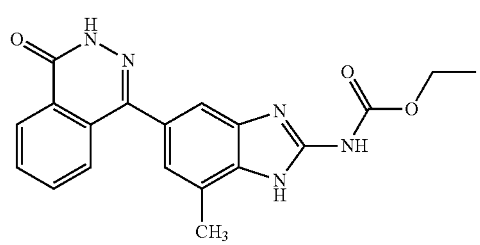 | Ethyl (7-methyl-5-(4-oxo-3,4-dihydrophthalazin-1-yl)-1H-benzimidazol-2-yl)carbamate |
| 92. | 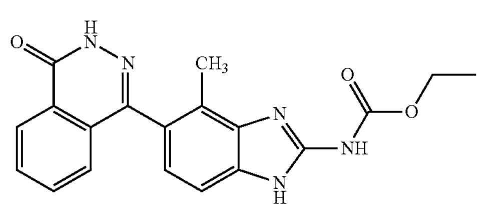 [SMILES: CCOC(=O)Nc1nc2c(C)c(-c3n[nH]c(=O)c4ccccc34)ccc2[nH]1] | Ethyl (4-methyl-5-(4-oxo-3,4-dihydrophthalazin-1-yl)-1H-benzimidazol-2-yl)carbamate |

| Compound No. | Structure | Name |
|---|---|---|
| 93. | 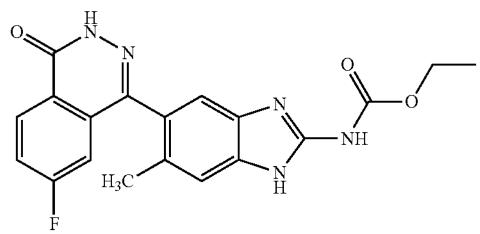 [SMILES: CCOC(=O)Nc1nc2cc(-c3n[nH]c(=O)c4ccc(F)cc34)c(C)cc2[nH]1] | Ethyl (5-(7-fluoro-4-oxo-3,4-dihydrophthalazin-1-yl)-6-methyl-1H-benzimidazol-2-yl)carbamate |
| 94. | 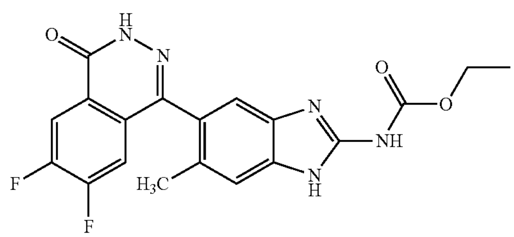 [SMILES: CCOC(=O)Nc1nc2cc(-c3n[nH]c(=O)c4cc(F)c(F)cc34)c(C)cc2[nH]1] | Ethyl (5-(6,7-difluoro-4-oxo-3,4-dihydrophthalazin-1-yl)-6-methyl-1H-benzimidazol-2-yl)carbamate |
| 95. | 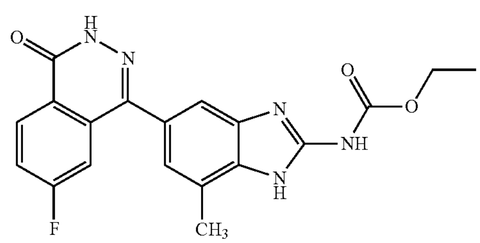 [SMILES: CCOC(=O)Nc1nc2cc(-c3n[nH]c(=O)c4ccc(F)cc34)cc(C)c2[nH]1] | Ethyl (5-(7-fluoro-4-oxo-3,4-dihydrophthalazin-1-yl)-7-methyl-1H-benzimidazol-2-yl)carbamate |
| 96. | 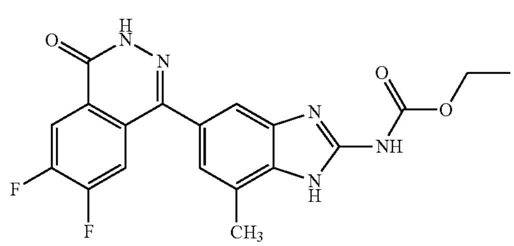 [SMILES: CCOC(=O)Nc1nc2cc(-c3n[nH]c(=O)c4cc(F)c(F)cc34)cc(C)c2[nH]1] | Ethyl (5-(6,7-difluoro-4-oxo-3,4-dihydrophthalazin-1-yl)-7-methyl-1H-benzimidazol-2-yl)carbamate |
| 97. | 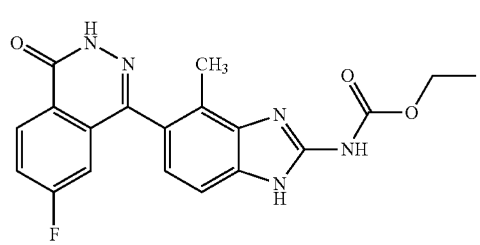 [SMILES: CCOC(=O)Nc1nc2c(C)c(-c3n[nH]c(=O)c4ccc(F)cc34)ccc2[nH]1] | Ethyl (5-(7-fluoro-4-oxo-3,4-dihydrophthalazin-1-yl)-4-methyl-1H-benzimidazol-2-yl)carbamate |
| 98. | 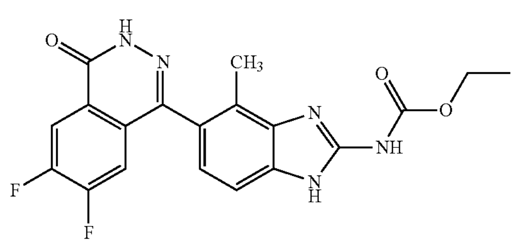 [SMILES: CCOC(=O)Nc1nc2c(C)c(-c3n[nH]c(=O)c4cc(F)c(F)cc34)ccc2[nH]1] | Ethyl (5-(6,7-difluoro-4-oxo-3,4-dihydrophthalazin-1-yl)-4-methyl-1H-benzimidazol-2-yl)carbamate |

-continued

| Compound No. | Structure | Name |
|---|---|---|
| 99. | 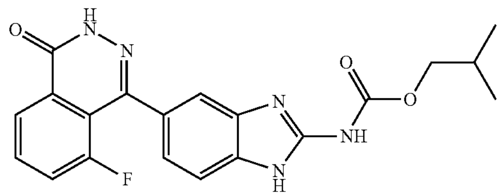 [SMILES: CC(C)COC(=O)Nc1nc2cc(-c3n[nH]c(=O)c4cccc(F)c34)ccc2[nH]1] | Isobutyl (5-(8-fluoro-4-oxo-3,4-dihydrophthalazin-1-yl)-1H-benzimidazol-2-yl)carbamate |
| 100. | 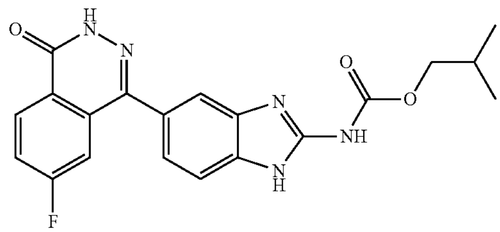 [SMILES: CC(C)COC(=O)Nc1nc2cc(-c3n[nH]c(=O)c4ccc(F)cc34)ccc2[nH]1] | Isobutyl (5-(7-fluoro-4-oxo-3,4-dihydrophthalazin-1-yl)-1H-benzimidazol-2-yl)carbamate |
| 101. | 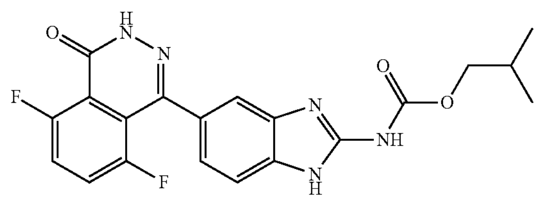 [SMILES: CC(C)COC(=O)Nc1nc2cc(-c3n[nH]c(=O)c4c(F)ccc(F)c34)ccc2[nH]1] | Isobutyl (5-(5,8-difluoro-4-oxo-3,4-dihydrophthalazin-1-yl)-1H-benzimidazol-2-yl)carbamate |
| 102. | 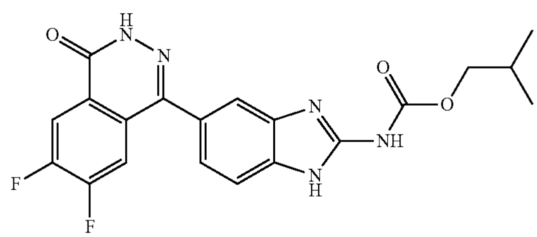 [SMILES: CC(C)COC(=O)Nc1nc2cc(-c3n[nH]c(=O)c4cc(F)c(F)cc34)ccc2[nH]1] | Isobutyl (5-(6,7-difluoro-4-oxo-3,4-dihydrophthalazin-1-yl)-1H-benzimidazol-2-yl)carbamate |
| 103. | 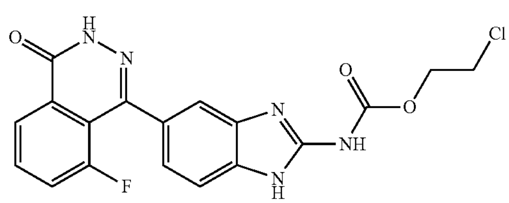 [SMILES: O=C(Nc1nc2cc(-c3n[nH]c(=O)c4cccc(F)c34)ccc2[nH]1)OCCCl] | 2-Chloroethyl (5-(8-fluoro-4-oxo-3,4-dihydrophthalazin-1-yl)-1H-benzimidazol-2-yl)carbamate |
| 104. | 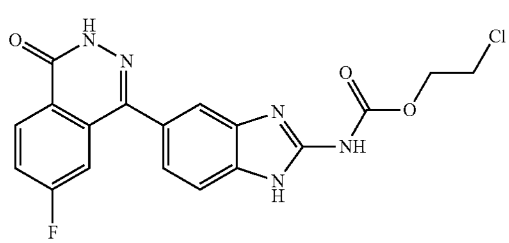 [SMILES: O=C(Nc1nc2cc(-c3n[nH]c(=O)c4ccc(F)cc34)ccc2[nH]1)OCCCl] | 2-Chloroethyl (5-(7-fluoro-4-oxo-3,4-dihydrophthalazin-1-yl)-1H-benzimidazol-2-yl)carbamate |
| 105. | 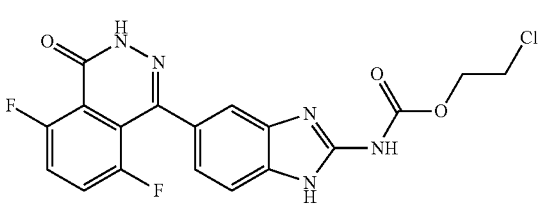 [SMILES: O=C(Nc1nc2cc(-c3n[nH]c(=O)c4c(F)ccc(F)c34)ccc2[nH]1)OCCCl] | 2-Chloroethyl (5-(5,8-difluoro-4-oxo-3,4-dihydrophthalazin-1-yl)-1H-benzimidazol-2-yl)carbamate |

-continued

| Compound No. | Structure | Name |
|---|---|---|
| 106. | 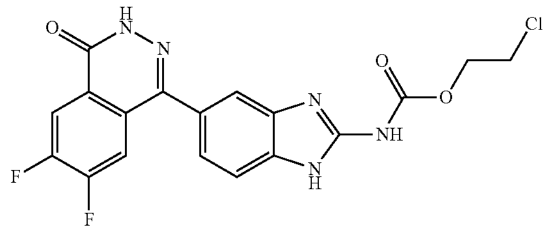 [SMILES: O=C(Nc1nc2cc(-c3n[nH]c(=O)c4cc(F)c(F)cc34)ccc2[nH]1)OCCCl] | 2-Chloroethyl (5-(6,7-difluoro-4-oxo-3,4-dihydrophthalazin-1-yl)-1H-benzimidazol-2-yl)carbamate |
| 107. | 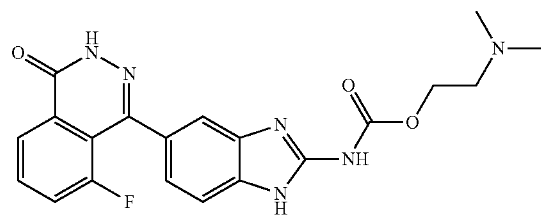 [SMILES: CN(C)CCOC(=O)Nc1nc2cc(-c3n[nH]c(=O)c4cccc(F)c34)ccc2[nH]1] | 2-(Dimethylamino)ethyl (5-(8-fluoro-4-oxo-3,4-dihydrophthalazin-1-yl)-1H-benzimidazol-2-yl)carbamate |
| 108. | 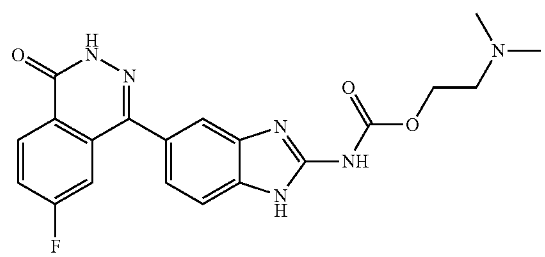 [SMILES: CN(C)CCOC(=O)Nc1nc2cc(-c3n[nH]c(=O)c4ccc(F)cc34)ccc2[nH]1] | 2-(Dimethylamino)ethyl (5-(7-fluoro-4-oxo-3,4-dihydrophthalazin-1-yl)-1H-benzimidazol-2-yl)carbamate |
| 109. | 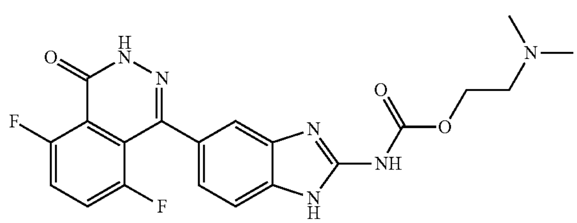 [SMILES: CN(C)CCOC(=O)Nc1nc2cc(-c3n[nH]c(=O)c4c(F)ccc(F)c34)ccc2[nH]1] | 2-(Dimethylamino)ethyl (5-(5,8-difluoro-4-oxo-3,4-dihydrophthalazin-1-yl)-1H-benzimidazol-2-yl)carbamate |
| 110. | 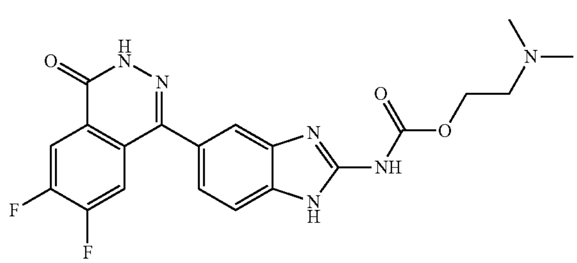 [SMILES: CN(C)CCOC(=O)Nc1nc2cc(-c3n[nH]c(=O)c4cc(F)c(F)cc34)ccc2[nH]1] | 2-(Dimethylamino)ethyl (5-(6,7-difluoro-4-oxo-3,4-dihydrophthalazin-1-yl)-1H-benzimidazol-2-yl)carbamate |
| 111. | 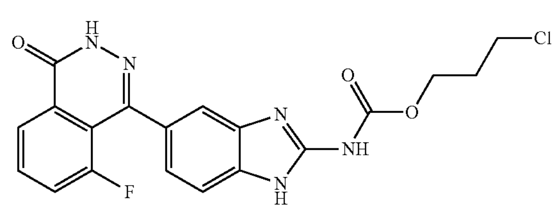 [SMILES: O=C(Nc1nc2cc(-c3n[nH]c(=O)c4cccc(F)c34)ccc2[nH]1)OCCCCl] | 3-Chlorpropyl (5-(8-fluoro-4-oxo-3,4-dihydrophthalazin-1-yl)-1H-benzimidazol-2-yl)carbamate |

-continued

| Compound No. | Structure | Name |
|---|---|---|
| 112. | 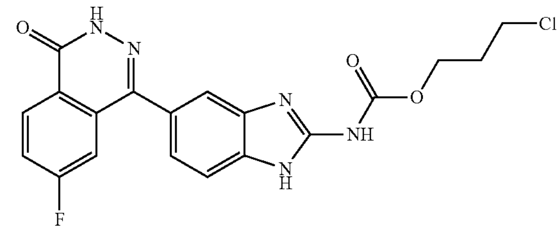 [SMILES: O=C(Nc1nc2cc(-c3n[nH]c(=O)c4ccc(F)cc34)ccc2[nH]1)OCCCCl] | 3-Chlorpropyl (5-(7-fluoro-4-oxo-3,4-dihydrophthalazin-1-yl)-1H-benzimidazol-2-yl)carbamate |
| 113. | 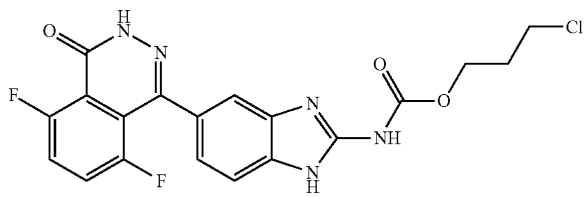 [SMILES: O=C(Nc1nc2cc(-c3n[nH]c(=O)c4c(F)ccc(F)c34)ccc2[nH]1)OCCCCl] | 3-Chlorpropyl (5-(5,8-difluoro-4-oxo-3,4-dihydrophthalazin-1-yl)-1H-benzimidazol-2-yl)carbamate |
| 114. | 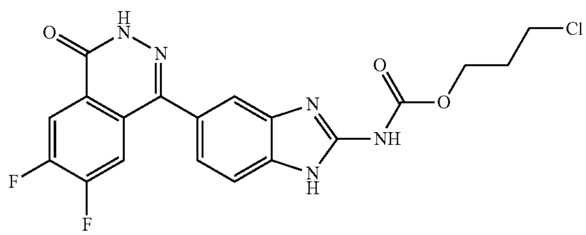 [SMILES: O=C(Nc1nc2cc(-c3n[nH]c(=O)c4cc(F)c(F)cc34)ccc2[nH]1)OCCCCl] | 3-Chlorpropyl (5-(6,7-difluoro-4-oxo-3,4-dihydrophthalazin-1-yl)-1H-benzimidazol-2-yl)carbamate |
| 115. | 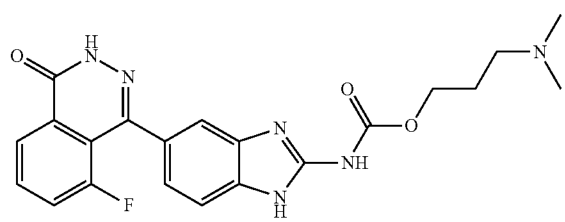 [SMILES: CN(C)CCCOC(=O)Nc1nc2cc(-c3n[nH]c(=O)c4cccc(F)c34)ccc2[nH]1] | 3-(Dimethylamino)propyl (5-(8-fluoro-4-oxo-3,4-dihydrophthalazin-1-yl)-1H-benzimidazol-2-yl)carbamate |
| 116. | 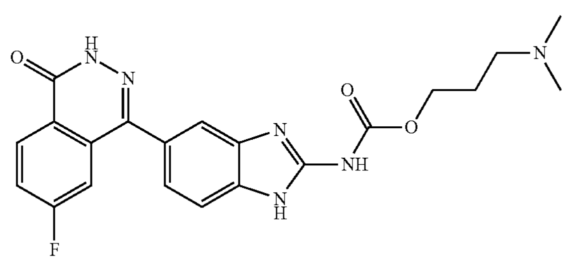 [SMILES: CN(C)CCCOC(=O)Nc1nc2cc(-c3n[nH]c(=O)c4ccc(F)cc34)ccc2[nH]1] | 3-(dimethylamino)propyl (5-(7-fluoro-4-oxo-3,4-dihydrophthalazin-1-yl)-1H-benzimidazol-2-yl)carbamate |
| 117. | 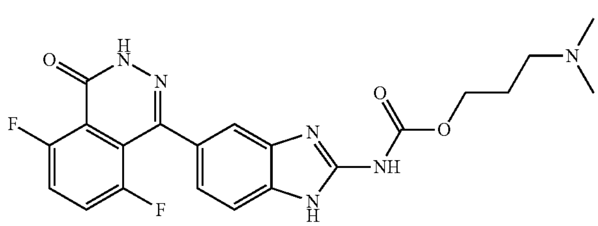 [SMILES: CN(C)CCCOC(=O)Nc1nc2cc(-c3n[nH]c(=O)c4c(F)ccc(F)c34)ccc2[nH]1] | 3-(dimethylamino)propyl (5-(5,8-difluoro-4-oxo-3,4-dihydrophthalazin-1-yl)-1H-benzimidazol-2-yl)carbamate |

| Compound No. | Structure | Name |
|---|---|---|
| 118. | 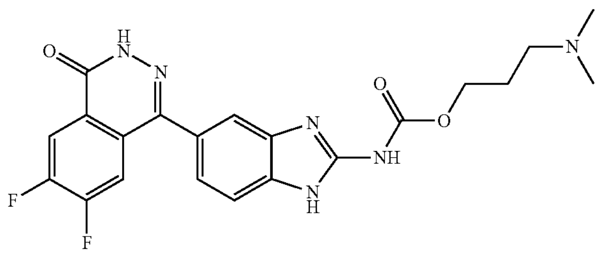 [SMILES: CN(C)CCCOC(=O)Nc1nc2cc(-c3n[nH]c(=O)c4cc(F)c(F)cc34)ccc2[nH]1] | 3-(dimethylamino)propyl (5-(6,7-difluoro-4-oxo-3,4-dihydrophthalazin-1-yl)-1H-benzimidazol-2-yl)carbamate |
| 119. | 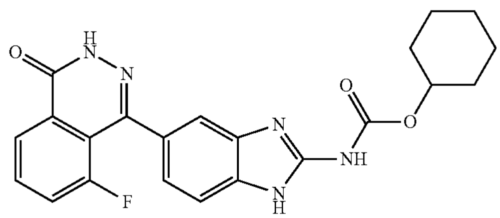 [SMILES: O=C(Nc1nc2cc(-c3n[nH]c(=O)c4cccc(F)c34)ccc2[nH]1)OC1CCCCC1] | Cyclohexyl (5-(8-fluoro-4-oxo-3,4-dihydrophthalazin-1-yl)-1H-benzimidazol-2-yl)carbamate |
| 120. | 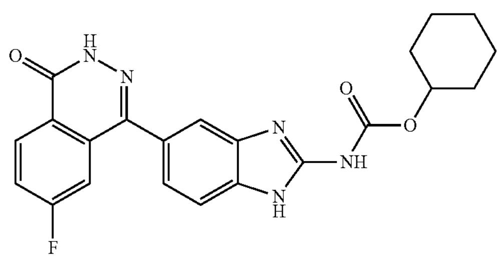 [SMILES: O=C(Nc1nc2cc(-c3n[nH]c(=O)c4ccc(F)cc34)ccc2[nH]1)OC1CCCCC1] | Cyclohexyl (5-(7-fluoro-4-oxo-3,4-dihydrophthalazin-1-yl)-1H-benzimidazol-2-yl)carbamate |
| 121. | 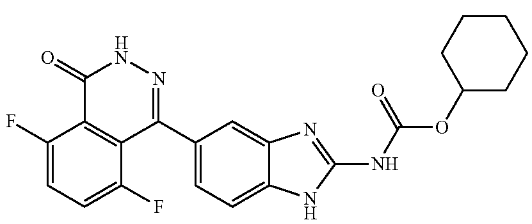 [SMILES: O=C(Nc1nc2cc(-c3n[nH]c(=O)c4c(F)ccc(F)c34)ccc2[nH]1)OC1CCCCC1] | Cyclohexyl (5-(5,8-difluoro-4-oxo-3,4-dihydrophthalazin-1-yl)-1H-benzimidazol-2-yl)carbamate |
| 122. | 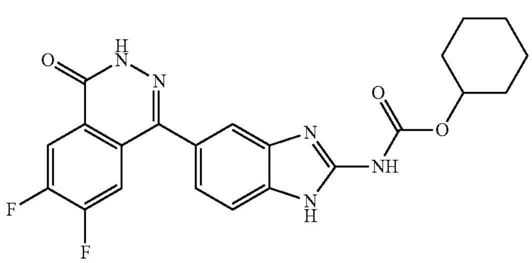 [SMILES: O=C(Nc1nc2cc(-c3n[nH]c(=O)c4cc(F)c(F)cc34)ccc2[nH]1)OC1CCCCC1] | Cyclohexyl (5-(6,7-difluoro-4-oxo-3,4-dihydrophthalazin-1-yl)-1H-benzimidazol-2-yl)carbamate |
| 123. | 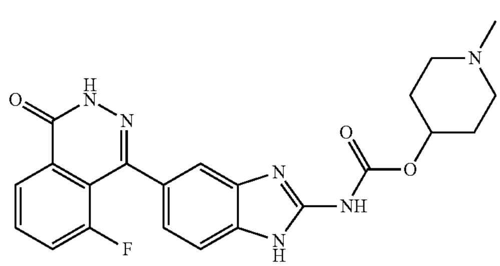 [SMILES: CN1CCC(OC(=O)Nc2nc3cc(-c4n[nH]c(=O)c5cccc(F)c45)ccc3[nH]2)CC1] | 1-Methylpiperidin-4-yl (5-(8-fluoro-4-oxo-3,4-dihydrophthalazin-1-yl)-1H-benzimidazol-2-yl)carbamate |

| Compound No. | Structure | Name |
|---|---|---|
| 124. | 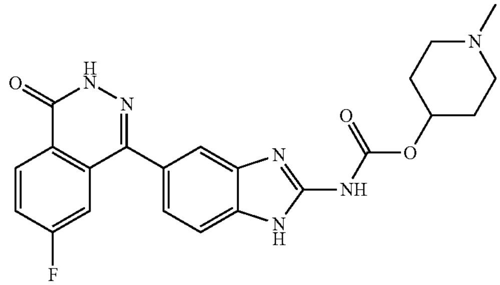 [SMILES: CN1CCC(OC(=O)Nc2nc3cc(-c4n[nH]c(=O)c5ccc(F)cc45)ccc3[nH]2)CC1] | 1-Methylpiperidin-4-yl (5-(7-fluoro-4-oxo-3,4-dihydrophthalazin-1-yl)-1H-benzimidazol-2-yl)carbamate |
| 125. | 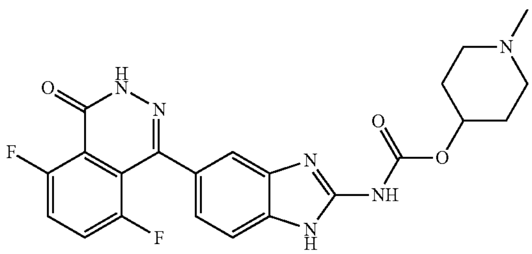 [SMILES: CN1CCC(OC(=O)Nc2nc3cc(-c4n[nH]c(=O)c5c(F)ccc(F)c45)ccc3[nH]2)CC1] | 1-Methylpiperidin-4-yl (5-(5,8-difluoro-4-oxo-3,4-dihydrophthalazin-1-yl)-1H-benzimidazol-2-yl)carbamate |
| 126. | 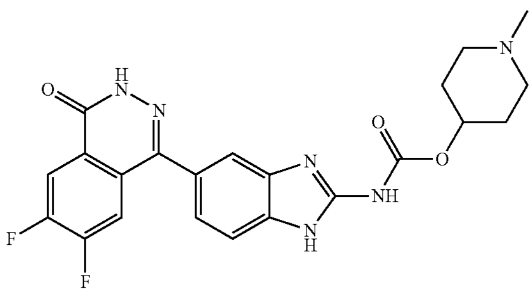 [SMILES: CN1CCC(OC(=O)Nc2nc3cc(-c4n[nH]c(=O)c5cc(F)c(F)cc45)ccc3[nH]2)CC1] | 1-Methylpiperidin-4-yl (5-(6,7-difluoro-4-oxo-3,4-dihydrophthalazin-1-yl)-1H-benzimidazol-2-yl)carbamate |
| 127. | 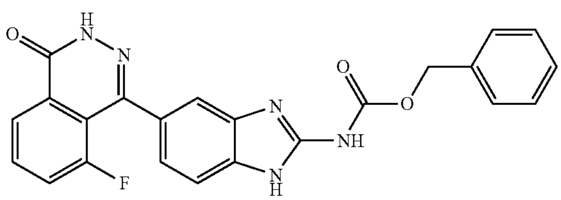 [SMILES: O=C(Nc1nc2cc(-c3n[nH]c(=O)c4cccc(F)c34)ccc2[nH]1)OCc1ccccc1] | Benzyl (5-(8-fluoro-4-oxo-3,4-dihydrophthalazin-1-yl)-1H-benzimidazol-2-yl)carbamate |
| 128. | 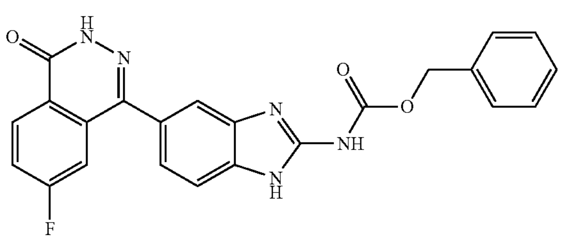 [SMILES: O=C(Nc1nc2cc(-c3n[nH]c(=O)c4ccc(F)cc34)ccc2[nH]1)OCc1ccccc1] | Benzyl (5-(7-fluoro-4-oxo-3,4-dihydrophthalazin-1-yl)-1H-benzimidazol-2-yl)carbamate |
| 129. | 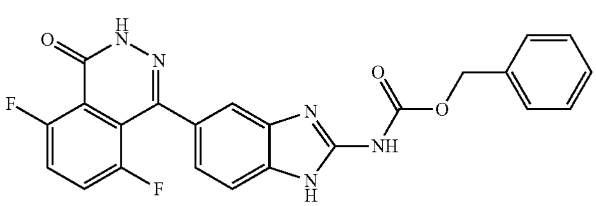 [SMILES: O=C(Nc1nc2cc(-c3n[nH]c(=O)c4c(F)ccc(F)c34)ccc2[nH]1)OCc1ccccc1] | Benzyl (5-(5,8-difluoro-4-oxo-3,4-dihydrophthalazin-1-yl)-1H-benzimidazol-2-yl)carbamate |

| Compound No. | Structure | Name |
|---|---|---|
| 130. | 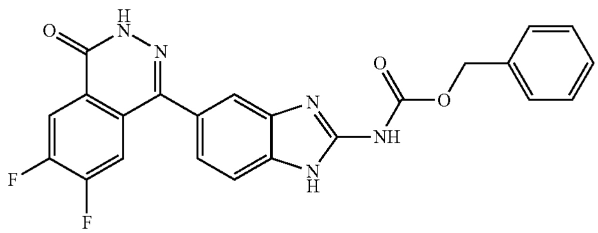 [SMILES: O=C(Nc1nc2cc(-c3n[nH]c(=O)c4cc(F)c(F)cc34)ccc2[nH]1)OCc1ccccc1] | Benzyl (5-(6,7-difluoro-4-oxo-3,4-dihydrophthalazin-1-yl)-1H-benzimidazol-2-yl)carbamate |
| 131. | 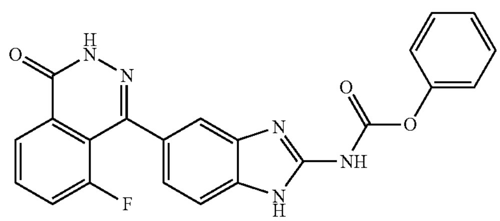 [SMILES: O=C(Nc1nc2cc(-c3n[nH]c(=O)c4cccc(F)c34)ccc2[nH]1)Oc1ccccc1] | Phenyl (5-(8-fluoro-4-oxo-3,4-dihydrophthalazin-1-yl)-1H-benzimidazol-2-yl)carbamate |
| 132. | 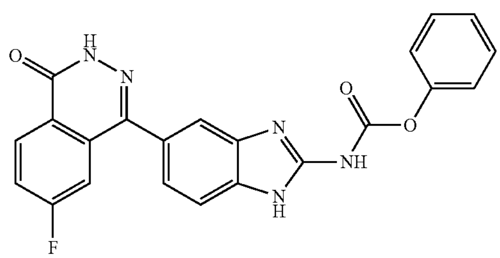 [SMILES: O=C(Nc1nc2cc(-c3n[nH]c(=O)c4ccc(F)cc34)ccc2[nH]1)Oc1ccccc1] | Phenyl (5-(7-fluoro-4-oxo-3,4-dihydrophthalazin-1-yl)-1H-benzimidazol-2-yl)carbamate |
| 133. | 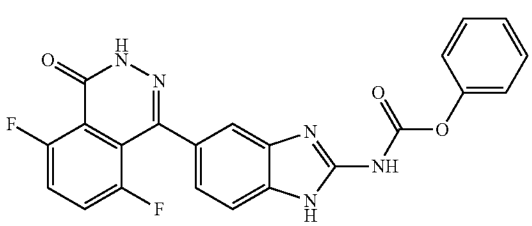 [SMILES: O=C(Nc1nc2cc(-c3n[nH]c(=O)c4c(F)ccc(F)c34)ccc2[nH]1)Oc1ccccc1] | Phenyl (5-(5,8-difluoro-4-oxo-3,4-dihydrophthalazin-1-yl)-1H-benzimidazol-2-yl)carbamate |
| 134. | 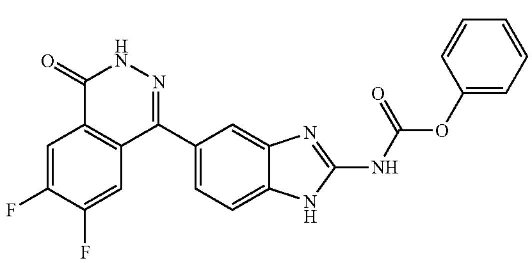 [SMILES: O=C(Nc1nc2cc(-c3n[nH]c(=O)c4cc(F)c(F)cc34)ccc2[nH]1)Oc1ccccc1] | Phenyl (5-(6,7-difluoro-4-oxo-3,4-dihydrophthalazin-1-yl)-1H-benzimidazol-2-yl)carbamate |
| 135. | 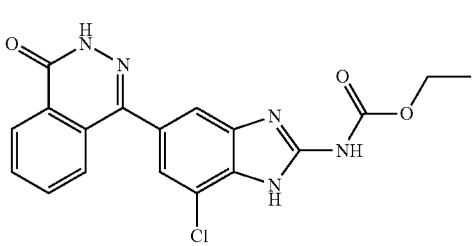 [SMILES: CCOC(=O)Nc1nc2cc(-c3n[nH]c(=O)c4ccccc34)cc(Cl)c2[nH]1] | Ethyl (7-chloro-5-(4-oxo-3,4-dihydrophthalazin-1-yl)-1H-benzimidazol-2-yl)carbamate |

| Compound No. | Structure | Name |
|---|---|---|
| 136. | 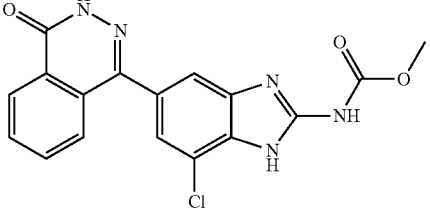 | Methyl (7-chloro-5-(4-oxo-3,4-dihydrophthalazin-1-yl)-1H-benzimidazol-2-yl)carbamate |
| 137. | 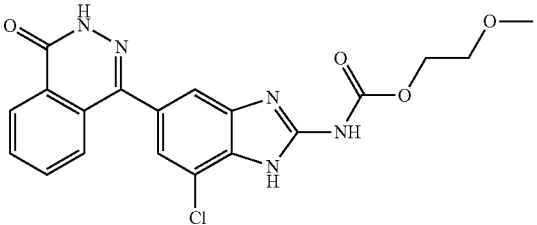 [SMILES: COCCOC(=O)Nc1nc2cc(-c3n[nH]c(=O)c4ccccc34)cc(Cl)c2[nH]1] | 2-Methoxyethyl (7-chloro-5-(4-oxo-3,4-dihydrophthalazin-1-yl)-1H-benzimidazol-2-yl)carbamate |
| 138. | 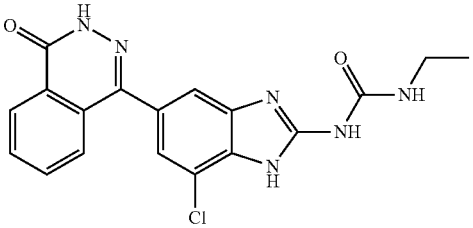 [SMILES: CCNC(=O)Nc1nc2cc(-c3n[nH]c(=O)c4ccccc34)cc(Cl)c2[nH]1] | 1-Ethyl-3-(7-chloro-5-(4-oxo-3,4-dihydrophthalazin-1-yl)-1H-benzimidazol-2-yl)urea |
| 139. | 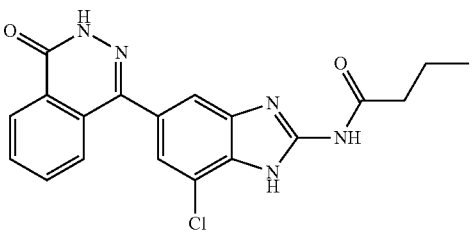 [SMILES: CCCC(=O)Nc1nc2cc(-c3n[nH]c(=O)c4ccccc34)cc(Cl)c2[nH]1] | N-(5-(7-chloro-4-oxo-3,4-dihydrophthalazin-1-yl)-1H-benzimidazol-2-yl)butyramide |
| 140. | 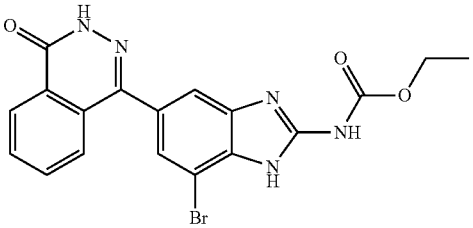 [SMILES: CCOC(=O)Nc1nc2cc(-c3n[nH]c(=O)c4ccccc34)cc(Br)c2[nH]1] | Ethyl (7-bromo-5-(4-oxo-3,4-dihydrophthalazin-1-yl)-1H-benzimidazol-2-yl)carbamate |
| 141. | 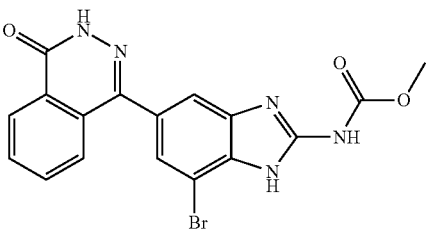 [SMILES: COC(=O)Nc1nc2cc(-c3n[nH]c(=O)c4ccccc34)cc(Br)c2[nH]1] | Methyl (7-bromo-5-(4-oxo-3,4-dihydrophthalazin-1-yl)-1H-benzimidazol-2-yl)carbamate |

-continued

| Compound No. | Structure | Name |
|---|---|---|
| 142. | 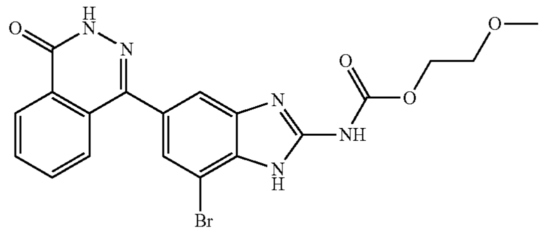 [SMILES: COCCOC(=O)Nc1nc2cc(-c3n[nH]c(=O)c4ccccc34)cc(Br)c2[nH]1] | 2-Methoxyethyl (7-bromo-5-(4-oxo-3,4-dihydrophthalazin-1-yl)-1H-benzimidazol-2-yl)carbamate |
| 143. | 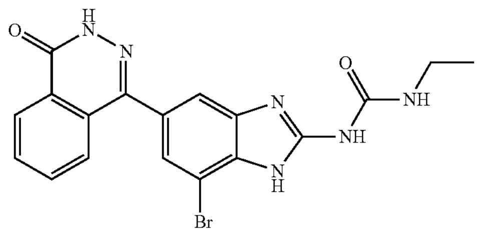 [SMILES: CCNC(=O)Nc1nc2cc(-c3n[nH]c(=O)c4ccccc34)cc(Br)c2[nH]1] | 1-Ethyl-3-(7-bromo-5-(4-oxo-3,4-dihydrophthalazin-1-yl)-1H-benzimidazol-2-yl)urea |
| 144. | 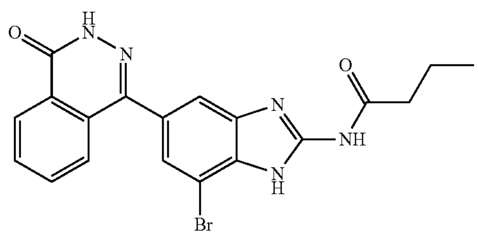 [SMILES: CCCC(=O)Nc1nc2cc(-c3n[nH]c(=O)c4ccccc34)cc(Br)c2[nH]1] | N-(5-(7-bromo-4-oxo-3,4-dihydrophthalazin-1-yl)-1H-benzimidazol-2-yl)butyramide |
| 145. | 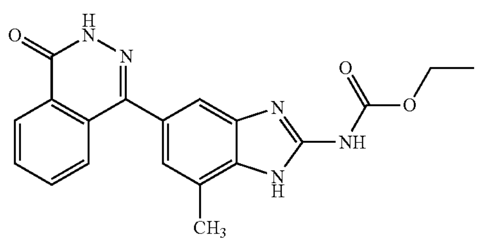 [SMILES: CCOC(=O)Nc1nc2cc(-c3n[nH]c(=O)c4ccccc34)cc(C)c2[nH]1] | Ethyl (7-methyl-5-(4-oxo-3,4-dihydrophthalazin-1-yl)-1H-benzimidazol-2-yl)carbamate |
| 146. | 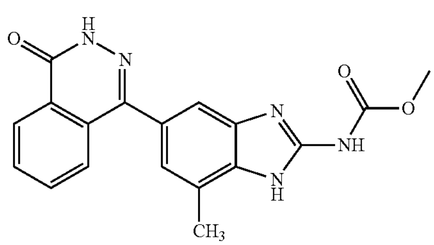 [SMILES: COC(=O)Nc1nc2cc(-c3n[nH]c(=O)c4ccccc34)cc(C)c2[nH]1] | Methyl (7-methyl-5-(4-oxo-3,4-dihydrophthalazin-1-yl)-1H-benzimidazol-2-yl)carbamate |
| 147. | 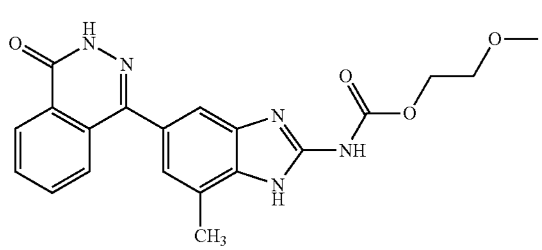 [SMILES: COCCOC(=O)Nc1nc2cc(-c3n[nH]c(=O)c4ccccc34)cc(C)c2[nH]1] | 2-Methoxyethyl (7-methyl-5-(4-oxo-3,4-dihydrophthalazin-1-yl)-1H-benzimidazol-2-yl)carbamate |

-continued

| Compound No. | Structure | Name |
| --- | --- | --- |
| 148. | 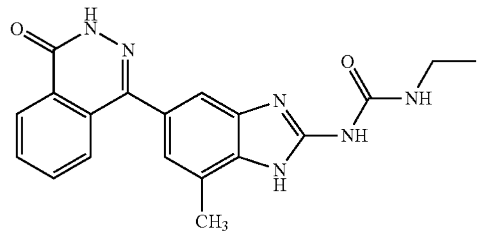 [SMILES: CCNC(=O)Nc1nc2cc(-c3n[nH]c(=O)c4ccccc34)cc(C)c2[nH]1] | 1-Ethyl-3-(7-methyl-5-(4-oxo-3,4-dihydrophthalazin-1-yl)-1H-benzimidazol-2-yl)urea |
| 149. | 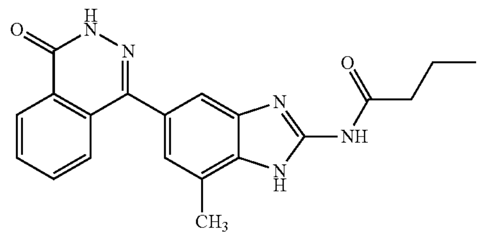 | N-(5-(7-methyl-4-oxo-3,4-dihydrophthalazin-1-yl)-1H-benzimidazol-2-yl)butyramide |

Example 2

PARP Enzymatic Activity Inhibition: Determination of IC50 Values for Selected Compounds (Data in FIG. 1)

The half maximal inhibitory concentration (IC50) with respect to PARP inhibition was determined for each test compound by using Trevigen's HT Universal PARP Assay Kit, according to the manufacturer's protocol (Cat#4677-096-K, Gaithersburg, Md.). This assay measures the incorporation of biotinylated poly(ADP-ribose) onto histone proteins in a 96-well strip well format. This assay is ideal for the determination of IC50 values of known or suspected PARP inhibitors. Briefly, stock solutions of each test compound were prepared in DMSO. Histone strip wells were incubated for 30 minutes at room temperature with 50 µl/well of 1×PARP Buffer to rehydrate the histones. Serial dilutions of either test compound were added to appropriate wells. Diluted PARP enzyme (0.5 Unit/well) was then added to the wells containing compounds, and incubated for 10 minutes at room temperature. Subsequently, 25 µl of 1×PARP Cocktail, containing activated DNA, was distributed into each well. Three types of control wells were also analyzed; i. A negative control without PARP was prepared to determine background absorbance. ii. An activity control for PARP Inhibitor Study: 0.5 Unit/well PARP-HSA without inhibitors. These wells provided the 100% activity reference point. iii. And a PARP Standard Curve: Serial dilution of the PARP-HAS standard were prepared in cold microtubes with 1×PARP Buffer such that the total activity is 1 Unit/25 µl, 0.5 Units/25 µl, 0.25 Units/25 µl, 0.1 Units/25 µl, 0.05 Units/25 µl, 0.025 Units/25 µl, and 0.01 Units/25 µl, 25 µl of each standard was added to triplicate wells. Following a 60 minutes incubation at room temperature, the strip wells were washed twice with 1×PBS+0.1% Triton X-100, and twice with 1×PBS. For activity detection, 50 µl per well of diluted Strep-HRP was added, and then incubated at room temperature for 60 minutes. Subsequently, 50 µl per well of pre-warmed TACS-Sapphire™ colorimetric substrate was added followed by a 15 minutes incubation, in the dark, at room temperature. The reactions were then stopped by adding 50 µl per well of 0.2M HCl or 5% Phosphoric Acid and read the absorbance at 450 nm.

The IC50 values were determined by performing non-linear regression analysis fitting velocities and the logarithm of inhibitor concentrations to a sigmoidal dose response with a variable slope model using the GraphPad Prism 6.0 software.

ABL Kinase Assays (Data in FIG. 1)

The direct inhibitory effect of the test compounds on the the ABL kinases activity was assessed using the Z'-LYTE biochemical kinase profiling assays (SelectScreen Kinase Profiling assays, Life Technologies). The Z'-LYTE biochemical assay employs a fluorescence-based, coupled-enzyme format and is based on the differential sensitivity of phosphorylated and non-phosphorylated peptides to proteolytic cleavage. The peptide substrate is labeled with two fluorophores (one at each end) that make up a FRET pair. In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor and acceptor fluorophores on the FRET-peptide, whereas uncleaved, phosphorylated FRET-peptides maintain FRET. The extent of phosphorylation of the FRET-peptide can be calculated from the Emission Ratio between cleaved and uncleaved FRET-peptides. The Emission Ratio will remain low if the FRET-peptide is phosphorylated (i.e., no kinase inhibition) and will be high if the FRET-peptide is non-phosphorylated (i.e., kinase inhibition).

Using the above described assay, The Test Compounds were screened in 1% DMSO (final) in the well. 10 point titrations, 3-fold serial dilutions were conducted. Briefly, in a black 384-well plate serial dilutions of test compound or 100 nL 100× were mixed with kinase buffer peptide/Kinase Mixture and ATP Solution (10 µM final). After one hour Kinase Reaction incubation at room temperature, the development Reagent Solution was added. Subsequently, the fluorescence signals were measured using a fluorescence plate reader. Data were analyzed and the IC50 were calculated with XLfit graphing software using the sigmoidal dose-response model.

The following controls were made for each individual kinase and are located on the same plate as the kinase:
0% Phosphorylation Control (100% Inhibition Control)

The maximum Emission Ratio is established by the 0% Phosphorylation Control (100% Inhibition Control), which contains no ATP and therefore exhibits no kinase activity. This control yields 100% cleaved peptide in the Development Reaction.
100% Phosphorylation Control The 100% Phosphorylation Control, which consists of a synthetically phosphorylated peptide of the same sequence as the peptide substrate, is designed to allow for the calculation of percent phosphorylation. This control yields a very low percentage of cleaved peptide in the Development Reaction.

The 0% Phosphorylation and 100% Phosphorylation Controls allow one to calculate the percent Phosphorylation achieved in a specific reaction well. Control wells do not include any kinase inhibitors.
0% Inhibition Control The minimum Emission Ratio in a screen is established by the 0% Inhibition Control, which contains active kinase. This control is designed to produce a 10-50% phosphorylated peptide in the Kinase Reaction.
Histone H2AX Pharmacodynamic Assay (Trevigen Gaithersburg Cat #4418-096-K) (Data in FIG. 1)

Histone H2AX is a 14 kDa ubiquitous member of the H2A histone family that becomes rapidly phosphorylated at Serine 139 by ATM and ATR kinases to yield a form known as gamma-H2AX in response to double-strand DNA damage and apoptosis. gamma-H2AX is an ideal Pharmacodynamic (PD) surrogate marker to measure molecular responses to a large number of drugs; The high throughput ELISA assay measures gamma-H2AX levels in cellular extracts and phosphorylation of H2AX in response to therapeutic intervention. This assay documents differences of gamma-H2AX in cells and tissue.

MDA-MB-436 breast cell lines were treated with either test compound (1 μM) Oliparib (1 μM), or DMSO control and lysed according to assay protocol and L-H2AX levels were measured by gamma-H2AX ELISA assay. Briefly, this assay uses 96-well plates pre-coated with a highly purified gamma-H2AX antibody. gamma-H2AX from testing sample lysate extracted from cells was captured by the antibody coated on the plate, followed by the addition of anti H2AX mouse IgM which binds to the captured targets on the plate. Next a secondary Goat anti mouse IgM HRP was used to further detect the target complex. Finally, a chemiluminescent substrate was added to each well and yielded relative light units (RLU) that directly correlate with the amount of gamma-H2AX in the testing sample.

Using GraphPad Prism 6.0 software, the changes in the amount of gamma-H2x in compounds treated cells were calculated as a percentage of increase versus its amounts in DMSO treated control cells.
Tubulin Polymerization Assay (Data in FIG. 1)

The high-throughput screening-tubulin polymerization assay kit (Cytoskeleton, Cat. # BK011P) is an economical one step procedure for determining the effects of drugs or proteins on tubulin polymerization. Polymerization is followed by fluorescence enhancement due to the incorporation of a fluorescent reporter into microtubules as polymerization occurs. The standard assay tubulin generates a polymerization curve representing the three phases of microtubule formation, namely nucleation, growth, and steady state equilibrium. Compounds that interact with tubulin will often alter one or more of the characteristic phases of polymerization. For example, the anti-mitotic drug paclitaxel eliminates the nucleation phase and enhances the Vmax of the growth phase. Similarly, the microtubule destabilizing drug, vinblastine (also antimitotic) causes a decrease in Vmax and a reduction in final polymer mass. Thus, one application of this assay is the identification of novel anti-mitotics.

The direct effects of the test compounds on tubulin polymerization were investigated using the abovementioned Tubulin polymerization assay kit (Cytoskeleton, Cat. # BK011P), as indicated by the manufacturer protocol. Briefly, bovine brain tubulin (400 μg/sample) in the presence of either 0.5% DMSO treated (control), 4 μM test compounds, 3 μM paclitaxel (Cytoskeleton), or 3 μM vinblastine (Cytoskeleton) was incubated in PEM buffer [80 mm PIPES, 1 mm EGTA, 1 mm MgCl2 (pH 6.8)] containing 1.0 mm GTP (G-PEM) and 15% glycerol, at 37 C. All samples (wells) contained 15% glycerol. The degree of polymerization over time was measured in a spectrophotometer (Biotek synergy HT plate reader) at 350 nm. All time points were plotted and analyzed using GraphPad Prism 6.0 software.

The results show the percentage of tubulin polymerization inhibition at 60 minutes, as compared to control (DMSO). Of note, at 60 min the steady state equilibrium was reached for the polymerization curve generated with DMSO control treatment. DMSO control was set as 0% inhibition. Positive values depict the percentage of decrease in Vmax and final polymer mass, as compared to control. Negative values are inversely correlated to degree of nucleation phase elimination and the percentage of increase of the Vmax, as compared to control.

| | Activity | | | | | |
|---|---|---|---|---|---|---|
| | PARP1 | PARP2 | ABL1 | Tubulin Polymerization Inhibition | A549 | OVCAR8 |
| Compound No. 1. | D | A | A | Y | A | A |
| Compound No. 2. | E | NT | B | X | C | C |
| Compound No. 3. | D | NT | B | Y | C | C |
| Compound No. 9. | E | NT | A | NT | A | A |
| Compound No. 11. | E | NT | A | NT | A | A |
| Compound No. 20. | E | NT | B | NT | C | B |
| Compound No. 21. | E | NT | A | NT | B | B |
| Compound No. 23. | C | NT | A | NT | B | A |
| Compound No. 80. | E | NT | A | NT | C | C |
| Compound No. 86. | D | NT | A | NT | A | A |
| Compound No. 135. | C | NT | A | NT | A | A |
| Compound No. 139 | NT | NT | A | NT | A | A |
| Compound No. 140. | D | NT | A | NT | A | A |
| Compound No. 145. | E | NT | D | NT | A | A |

A = IC50 <0.5 μM
B = IC50 0.5 μM to 1 μM
C = IC50 1 μM to 5 μM
D = IC50 5 μM to 10 μM
E = IC50 >10 μM
X = (% Inhibition versus control) <20%. Results with a compound concentration of 4 μM
Y = (% Inhibition versus control) ≤20%. Results with a compound concentration of 4 μM
NT = Not Tested Cell Viability Assay in Solid Tumors Cell Lines (Data in FIG. 2)

Human cancer cell lines (lung, ovarian, breast pancreatic and mesothelioma) were purchased from the ATCC. The cell lines were cultured in RPMI 1640 (Life Technologies, Carlsbad, Calif.) supplemented with 10% fetal bovine serum (FBS) and antibiotics. 2000 cells were seeded in 96 well costar plate one day before treatment with test compounds, Olaparib (Selleck Chemicals), Imatnib Mesylate (Selleck Chemicals) or ponatinib at different concentrations for 72 hours, with vehicle (DMSO) as controls. At the end of treatment, cell proliferation was determined by an intracellular adenosine triphosphate monitoring system (Cell-Titer Glo-Promega).

Inhibitory activity was evaluated comparing treated versus control data using the GraphPad Prism 6.0 software. The dose inhibiting 50% (IC50) of cell viability was calculated using non-linear regression curve. Results show the mean IC50 value from three different experiments.

Cell Viability Assay in Solid Multiple Myeloma Cell Lines (Data in FIG. 3)

Multiple myeloma (MM) Cells were obtained from the Center for Myeloma Therapeutics at UCSF. MM cells were cultured in RPMI-1640 supplemented with 20% FBS, penicillin/streptomycin and L-Glutamine. Cells at a density of 15×103 cells/well (100 ul/well) were dispensed into 96-well plates One day before treatment with serial dilutions of aforementioned compounds for 72 h. At the end of treatment, cell proliferation and IC50 were determined as mentioned above for solid tumors cell lines.

Tumor Xenografts Studies (Data in FIGS. 4-7)

8 million cells (either OVCAR-8 or MSTO-211H) were mixed with 50% matrigel (BD Biosciences, Bedford, Mass.) and inoculated by Subcutaneously into the flank of 6-8 week old female NOD/SCID (NSG). There were five mice in each of the control groups and five mice in each of the treatment groups. When tumors reached a volume of 150-250 mm3, the mice were randomized into groups (5 per group) and treated daily by oral gavage with Test compound (at the indicated dosage) or diluent (aqueous 25 mmol/L citrate buffer, pH=2.75) alone as a control. All mice were monitored daily for signs of morbidity and mortality. Mice weight and tumor volume were monitored every 3-4 days for the duration of the study.

Single-Dose Pharmacokinetic Study after Oral Gavage Administration (Data in FIG. 8)

To determine the bioavailability of the test compound, we have performed a single-dose concentration curve study, after oral gavage administration. A single oral dose (10 mg/kg) was administered to 6-8 weeks old NSG mice. Subsequently, blood samples were collected from each mouse, at the various time points (0, 0.5, 1, 3, 8, and 24 hours). Next, plasmas were prepared and drug concentrations in the plasma were determined and graphed against time. For each time point, drug concentrations were evaluated in three different plasma samples.

Evaluation of In Vitro Combination Therapy (Data in FIG. 9)

Cancer cell lines were seeded at 1000 cells per well in 96 well costar plate one day before treatment with serial concentrations of test compound alone, a chemotherapeutic agent alone (cisplatin or paclitaxel: (Selleck Chemicals)), or 2 drug combination of test compound with either chemotherapeutic agents. Vehicle (DMSO) was used as control treatment. Subsequently, the treated cells were incubated at 37° C. for 72 hours. At the end of treatment, cell proliferation was determined by an intracellular adenosine triphosphate monitoring system (Cell-Titer Glo-Promega), and the chemiluminescece signals were read using GoMax 96 microplate luminometer.

The inhibitory activity was evaluated by comparing treated versus control data using the GraphPad Prism 6.0 software. The dose inhibiting 50% (IC50) of cell viability, for each drug alone or 2 drugs combination treatments, was calculated using non-linear regression curve.

For combination drug analysis, the Combination Indices (C.I.) were calculated based on the equation of Chou-Talalay (Adv Enzyme Regul 1984; 22:27-55) for mutually nonexclusive drugs, where a C.I. of <1.3 and >0.9 indicates an additive effect: C.I. of >1.3 antagonism; CI of <0.9 synergism.

$$CI=[A]_c/[A]_a+[B]_c/[B]_a+[A]_cX[B]_c/[A]_aX[B]_a.$$ Chou-Talalay equation:

$[A]_c$ and $[B]_c$ are the concentrations for compound A and compound B in combination to inhibit x % of cell viability, and $[A]_a$ and $[B]_a$ are the concentration for compound A and B along to inhibit x % of cell viability.

Chemotherapeutic Agents Classification

Cisplatin is classified as an alkylating agent. Alkylating agents are most active in the resting phase of the cell. These drugs are cell cycle non-specific. There are several types of alkylating agents.

Mustard gas derivatives: Mechlorethamine, Cyclophosphamide, Chlorambucil, Melphalan, and Ifosfamide.

Ethylenimines: Thiotepa and Hexamethylmelamine.

Alkylsulfonates: Busulfan.

Hydrazines and Triazines: Procarbazine, Dacarbazine and Temozolomide.

Nitrosureas: Carmustine, Lomustine and Streptozocin. Nitrosureas are unique because, unlike most chemotherapy, they can cross the blood-brain barrier. They can be useful in treating brain tumors.

Metal salts: Carboplatin, Cisplatin, and Oxaliplatin.

Paclitaxel belongs to a class of chemotherapy drugs called plant alkaloids. Plant alkaloids are made from plants. The vinca alkaloids are made from the periwinkle plant (catharanthus rosea). The taxanes are made from the bark of the Pacific Yew tree (taxus). The vinca alkaloids and taxanes are also known as antimicrotubule agents. The podophyllotoxins are derived from the May Apple plant. Camptothecan analogs are derived from the Asian "Happy Tree" (Camptotheca acuminata). Podophyllotoxins and camptothecan analogs are also known as topoisomerase inhibitors. The plant alkaloids are cell-cycle specific. This means they attack the cells during various phases of division.

Vinca alkaloids: Vincristine, Vinblastine and Vinorelbine.

Taxanes: Paclitaxel and Docetaxel.

Podophyllotoxins: Etoposide and Tenisopide.

Camptothecan analogs: Irinotecan and Topotecan.

Antimicrotubule agents (such as Paclitaxel), inhibit the microtubule structures within the cell. Microtubules are part of the cell's apparatus for dividing and replicating itself. Inhibition of these structures ultimately results in cell death.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a salt or a hydrate or a solvate thereof, having a structure according to formula (I):

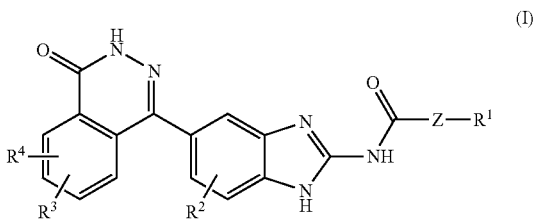

wherein Z is —O— or —CH$_2$— or —NH— or —N(CH$_2$R$^5$)— wherein R$^5$ is hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl; R$^1$ is hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ heteroalkyl or substituted or unsubstituted C$_3$ or C$_4$ or C$_5$ or C$_6$ cycloalkyl or unsubstituted phenyl or substituted or unsubstituted piperidinyl or substituted or unsubstituted azetidinyl; R$^2$ is hydrogen or methyl or ethyl or propyl or isopropyl or halogen; R$^3$ is hydrogen or fluoro or chloro or methyl or ethyl or propyl or isopropyl; R$^4$ is hydrogen or fluoro or chloro or methyl or ethyl or propyl or isopropyl with the proviso that the compound is not according to formula (XV):

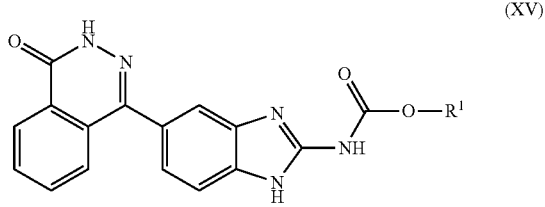

wherein R$^1$ is methyl or ethyl or unsubstituted C$_3$ alkyl.

2. The compound of claim 1, or a salt or a hydrate or a solvate thereof, wherein R$^2$ is H; R$^3$ is H; and R$^4$ is H.

3. The compound of claim 1, or a salt or a hydrate or a solvate thereof, wherein Z is O.

4. The compound of claim 1, or a salt or a hydrate or a solvate thereof, wherein R$^1$ is methyl.

5. The compound of claim 1, or a salt or a hydrate or a solvate thereof, wherein R$^1$ is ethyl.

6. The compound of claim 1, or a salt or a hydrate or a solvate thereof, wherein R$^1$ is C$_1$ or C$_2$ or C$_3$ or C$_4$ or C$_5$ or C$_6$ or C$_7$ or C$_8$ or C$_9$ or C$_{10}$ alkyl, substituted with unsubstituted C$_1$ or C$_2$ or C$_3$ or C$_4$ or C$_5$ or C$_6$ alkoxy.

7. The compound of claim 1, or a salt or a hydrate or a solvate thereof, wherein R$^1$ is C$_2$ alkyl, substituted with methoxy.

8. A pharmaceutical formulation comprising:
a) the compound, or a salt or a hydrate or a solvate thereof, of claim 1; and claim; and
b) a pharmaceutically acceptable excipient.

9. The pharmaceutical formulation of claim 8, wherein the pharmaceutical formulation is a unit dosage form.

10. The pharmaceutical formulation of claim 8 wherein the salt of the compound of is a pharmaceutically acceptable salt.

11. A method of inhibiting PARP1 and/or ABL1 and/or ABL2 and/or tubulin, comprising: contacting said PARP1 and/or ABL1 and/or ABL2 and/or tubulin with an effective amount of the compound of claim 1, thereby inhibiting said PARP1 and/or ABL1 and/or ABL2 and/or tubulin.

12. A method of treating cancer in an animal, comprising: administering to an animal suffering from said cancer a therapeutically effective amount of the compound of claim 1, wherein said cancer is multiple myeloma, lung cancer, ovarian cancer, pancreatic cancer, breast cancer, or mesothelioma, thereby treating the cancer.

13. The method of claim 12, wherein the cancer is multiple myeloma.

14. The method of claim 12, wherein the animal is a human.

15. The compound of claim 1, or a salt or a hydrate or a solvate thereof, wherein Z is —NH—.

16. The compound of claim 1, or a salt or a hydrate or a solvate thereof, wherein R$^2$ is methyl.

17. The compound of claim 1, or a salt or a hydrate or a solvate thereof, wherein R$^2$ is halogen.

18. The compound of claim 1, or a salt or a hydrate or a solvate thereof, wherein R$^2$ is chlorine.

19. The compound of claim 1, or a salt or a hydrate or a solvate thereof, wherein
R$^3$ is fluorine and R$^4$ is fluorine; or
R$^3$ is chlorine and R$^4$ is chlorine.

20. The compound of claim 1, or a salt or a hydrate or a solvate thereof, having a structure according to formula (II):

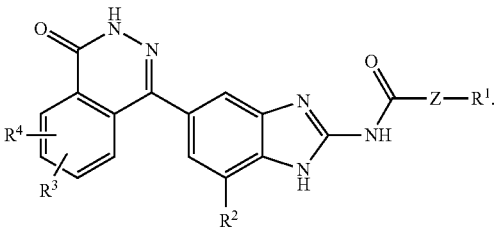

21. The compound of claim 1, or a salt or a hydrate or a solvate thereof, having a structure according to formula (III):

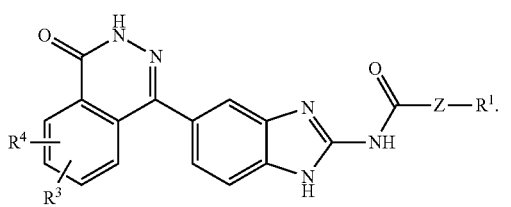

22. The compound of claim 1, or a salt or a hydrate or a solvate thereof, having a structure according to formula (IV):

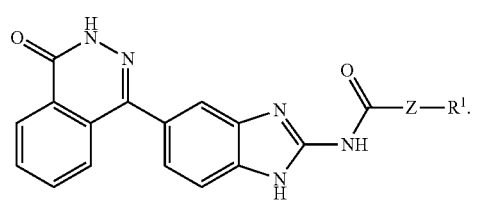

23. The compound of claim 1, or a salt or a hydrate or a solvate thereof, having a structure according to formula (V):

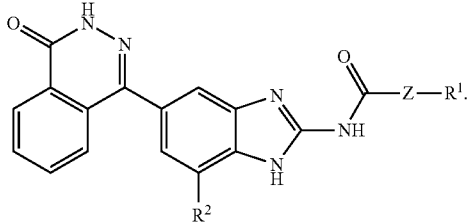

24. The compound of claim 23, or a salt or a hydrate or a solvate thereof, wherein $R^2$ is methyl or halogen.

25. The compound of claim 1, or a salt or a hydrate or a solvate thereof, having a structure according to formula (XIII):

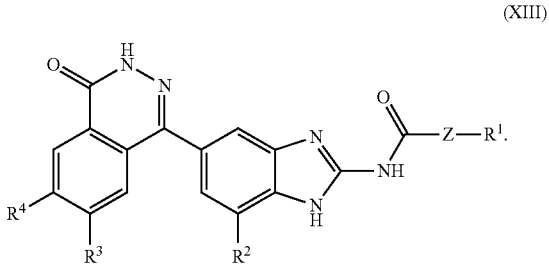

26. The compound of claim 25, or a salt or a hydrate or a solvate thereof, wherein $R^2$ is methyl or halogen.

27. The compound of claim 25, or a salt or a hydrate or a solvate thereof, wherein
$R^3$ is fluorine and $R^4$ is fluorine; or
$R^3$ is chlorine and $R^4$ is chlorine.

28. The compound of claim 1, or a salt or a hydrate or a solvate thereof, having a structure according to formula (XIV):

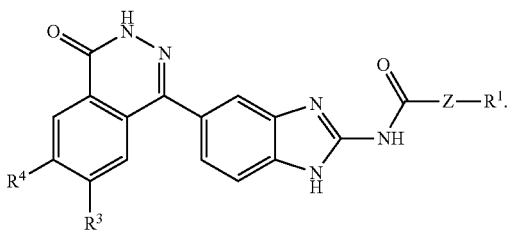

29. The compound of claim 28, or a salt or a hydrate or a solvate thereof, wherein
$R^3$ is fluorine and $R^4$ is fluorine; or
$R^3$ is chlorine and $R^4$ is chlorine.

30. The compound of claim 1, or a salt or a hydrate or a solvate thereof, which is 2-methoxyethyl (5-(4-oxo-3,4-dihydrophthalazin-1-yl)-1H-b enzimidazol-2-yl)carbamate or ethyl (5-(6,7-difluoro-4-oxo-3,4-dihydrophthalazin-1-yl)-1H-benzimidazol-2-yl)carbamate or 2-methoxyethyl (5-(6,7-difluoro-4-oxo-3,4-dihydrophthalazin-1-yl)-1H-benzimidazol-2-yl)carbamate or ethyl (5-(6,7-dichloro-4-oxo-3,4-dihydrophthalazin-1-yl)-1H-benzimidazol-2-yl)carbamate or 2-methoxyethyl (5-(6,7-dichloro-4-oxo-3,4-dihydrophthalazin-1-yl)-1H-benzimidazol-2-yl)carbamate or 1-ethyl-3-(5-(4-oxo-3,4-dihydrophthalazin-l-yl)-1H-benzimidazol-2-yl)urea or 1-cyclopropyl-3-(5-(4-oxo-3,4-dihydrophthalazin-1-yl)-1H-benzimidazol-2-yl)urea or ethyl (7-methyl-5-(4-oxo-3,4-dihydrophthalazin-1-yl)-1H-benzimidazol-2-yl)carbamate or ethyl (5-(6,7-difluoro-4-oxo-3,4-dihydrophthalazin-1-yl)-7-methyl-1H-benzimidazol-2-yl)carbamate or ethyl (7-chloro-5-(4-oxo-3,4-dihydrophthalazin-1-yl)-1H-benzimidazol-2-yl)carbamate or 2-methoxyethyl (7-chloro-5-(4-oxo-3,4-dihydrophthalazin-1-yl)-1H-benzimidazol-2-yl)carbamate or 1-ethyl-3-(7-chloro-5-(4-oxo-3,4-dihydrophthalazin-1-yl)-1H-benzimidazol-2-yl)urea or 2-methoxyethyl(7-methyl-5-(4-oxo-3,4-dihydrophthalazin-1-yl)-1H-benzimidazol-2-yl)carbamate or 1-ethyl-3-(7-methyl-5-(4-oxo-3,4-dihydrophthalazin-1-yl)-1H-benzimidazol-2-yl)urea.

31. The compound of claim 1, or a salt or a hydrate or a solvate thereof, wherein $R^1$ is substituted or unsubstituted $C_3$ or $C_4$ cycloalkyl.

32. The compound of claim 1, or a salt or a hydrate or a solvate thereof, wherein $R^1$ is substituted or unsubstituted $C_1$ or $C_2$ or $C_3$ alkyl.

33. The compound of claim 1, or a salt or a hydrate or a solvate thereof, wherein $R^1$ is $C_1$ or $C_2$ or $C_3$ alkyl, substituted with unsubstituted $C_1$ or $C_2$ or $C_3$ alkoxy.

34. The compound of claim 1, or a salt or a hydrate or a solvate thereof, wherein $R^1$ is $C_1$ or $C_2$ or $C_3$, substituted with unsubstituted dimethylamino.

35. The compound of claim 1, or a salt or a hydrate or a solvate thereof, wherein $R^1$ is $C_1$ or $C_2$ or $C_3$ or $C_4$ or $C_5$ alkyl, substituted with fluorine.

36. The compound of claim 1, or a salt or a hydrate or a solvate thereof, wherein $R^1$ is $C_1$ or $C_2$ or $C_3$ or $C_4$ or $C_5$ alkyl, substituted with one fluorine.

37. The compound of claim 1, or a salt or a hydrate or a solvate thereof, wherein $R^1$ is $C_1$ or $C_2$ or $C_3$ or $C_4$ or $C_5$ alkyl, substituted with two fluorines.

38. The compound of claim 1, or a salt or a hydrate or a solvate thereof, wherein $R^1$ is $C_1$ or $C_2$ or $C_3$ or $C_4$ or $C_5$ alkyl, substituted with three fluorines.

39. The compound of claim 1, or a salt or a hydrate or a solvate thereof, wherein $R^1$ is $C_1$ or $C_2$ alkyl, substituted with three fluorines.

* * * * *